United States Patent
Christensen et al.

(10) Patent No.: US 12,371,707 B2
(45) Date of Patent: Jul. 29, 2025

(54) MAIZE EVENT DP-915635-4 AND METHODS FOR DETECTION THEREOF

(71) Applicant: PIONEER HI-BRED INTERNATIONAL, INC., Johnston, IA (US)

(72) Inventors: Heather Marie Christensen, Ankeny, IA (US); Bin Cong, Johnston, IA (US); Virginia Crane, Des Moines, IA (US); Matthew Curtis Harmon, Urbandale, IA (US); Luciano M Jaureguy, Clive, IA (US); Jeffrey Klever, Grimes, IA (US); Albert L Lu, West Des Moines, IA (US); Kristen Denise Rinehart Krebs, Ankeny, IA (US); Margit C Ross, Johnston, IA (US)

(73) Assignee: PIONEER HI-BRED INTERNATIONAL, INC., Johnston, IA (US)

(*) Notice: Subject to any disclaimer, the term of this patent is extended or adjusted under 35 U.S.C. 154(b) by 892 days.

(21) Appl. No.: 17/332,245

(22) Filed: May 27, 2021

(65) Prior Publication Data
US 2021/0381000 A1 Dec. 9, 2021

Related U.S. Application Data

(60) Provisional application No. 63/116,192, filed on Nov. 20, 2020, provisional application No. 63/033,994, filed on Jun. 3, 2020.

(51) Int. Cl.
| | | |
|---|---|---|
| *C12N 15/82* | (2006.01) | |
| *A01H 1/00* | (2006.01) | |
| *A01H 5/10* | (2018.01) | |
| *A01H 6/46* | (2018.01) | |
| *C12Q 1/6895* | (2018.01) | |

(52) U.S. Cl.
CPC ......... *C12N 15/8286* (2013.01); *A01H 1/127* (2021.01); *A01H 5/10* (2013.01); *A01H 6/4684* (2018.05); *C12Q 1/6895* (2013.01); *C12Q 2600/13* (2013.01)

(58) Field of Classification Search
None
See application file for complete search history.

(56) References Cited

U.S. PATENT DOCUMENTS

| | | | |
|---|---|---|---|
| 9,775,316 B1 | 10/2017 | Chandler et al. | |
| 2003/0191077 A1* | 10/2003 | Fosnaugh | C12N 15/113 435/375 |
| 2004/0175441 A1* | 9/2004 | Bootland | C12N 15/8257 424/725 |
| 2012/0210462 A1 | 8/2012 | Bermudez et al. | |
| 2015/0361446 A1* | 12/2015 | Beatty | C07K 14/325 435/6.12 |
| 2016/0208271 A1* | 7/2016 | Cigan | C12N 15/8247 |
| 2016/0348131 A1 | 12/2016 | Anderson et al. | |
| 2018/0222947 A1 | 8/2018 | Allen et al. | |
| 2023/0210079 A1 | 7/2023 | Christensen | |

FOREIGN PATENT DOCUMENTS

| | | |
|---|---|---|
| WO | 2014116854 A1 | 7/2014 |
| WO | 2016109157 A1 | 7/2016 |
| WO | 2017222821 A2 | 12/2017 |
| WO | 2018102131 A1 | 6/2018 |
| WO | 2019209700 A1 | 10/2019 |
| WO | 2019217358 A1 | 11/2019 |

OTHER PUBLICATIONS

"Enzymatic Assay of ?-Glucosidase, Sigma Quality Control Test Procedure," Sigma Product Information, Sep. 8, 1996, 3 Pages.
International Preliminary Report on Patentability for International Application No. PCT/US2021/031718, mailed Dec. 15, 2022, 11 Pages.
International Search Report and Written Opinion for International Application No. PCT/US2021/031718, mailed Nov. 4, 2021, 19 Pages.
"TSA: Artemisia Annua Strain Artemis Contig7324.Aml mRNA Sequence," Nucleotide, GenBank Database Accession No. EZ193767, Aug. 11, 2010, URL: ncbi, XP055883580.
"Zea mays Mu Transposon Insertion mu1022756 Flanking Sequence," GenBank Database Accession No. HQ134002, Nucleotide, Oct. 17, 2010, URL: ncbi, XP055883591.
Extended European Search Report for European Application No. EP218179752, mailed May 13, 2024, Pages.

* cited by examiner

*Primary Examiner* — Charles Logsdon

(57) ABSTRACT

Embodiments disclosed herein relate to the field of plant molecular biology, specifically to DNA constructs for conferring insect resistance to a plant. Embodiments disclosed herein relate to insect resistant corn plant containing event DP-915635-4, and to assays for detecting the presence of event DP-915635-4 in samples and compositions thereof.

51 Claims, 6 Drawing Sheets

Specification includes a Sequence Listing.

FIG. 5

| EVENT | EARHT | | | MST | | | RS_PLTHT | | | YIELD | | |
|---|---|---|---|---|---|---|---|---|---|---|---|---|
| | Number of plots with trait data | Predicted value (in.) | Standard error | Number of plots with trait data | Predicted value (%) | Standard error | Number of plots with trait data | Predicted value (in.) | Standard error | Number of plots with trait data | Predicted value (bu/acre) | Standard error |
| DP-915635-4 | 17 | 54.12 | 3.31 | 20 | 18.76 | 0.94 | 19 | 106.46 | 4.46 | 19 | 212.01 | 7.93 |
| WT | 70 | 54.61 | 3.30 | 84 | 18.73 | 0.93 | 82 | 107.78 | 4.45 | 68 | 207.05 | 7.76 |

FIG. 6

| EVENT | EARHT | | | GDUSHD | | | PHTYLD | | | PLTHT_1 | | |
|---|---|---|---|---|---|---|---|---|---|---|---|---|
| | Number of plots with trait data | Predicted value (inches) | Standard error | Number of plots with trait data | Predicted value (GDU) | Standard error | Number of plots with trait data | Predicted value (bu/acre) | Standard error | Number of plots with trait data | Predicted value (inches) | Standard error |
| DP-915635-4 | 9 | 38.08 | 1.14 | 10 | 149.10 | 2.88 | 14 | 112.32 | 8.00 | 9 | 86.80 | 2.01 |
| WT | 38 | 42.82 | 1.03 | 39 | 150.81 | 2.86 | 55 | 129.66 | 7.61 | 37 | 91.83 | 1.94 |

```
                        SEQUENCE LISTING

<160> NUMBER OF SEQ ID NOS: 32

<210> SEQ ID NO 1
<211> LENGTH: 74997
<212> TYPE: DNA
<213> ORGANISM: Artificial Sequence
<220> FEATURE:
<223> OTHER INFORMATION: Synthetic

<400> SEQUENCE: 1
ccgctgtcgt cgatgacggc gtaatcgtgg gcaagaacgg cagctttatg gctgcctggc      60
tgtacaaggg cgatgacaac gcaagcagca ccgaccagca gcgcgaagta gtgtccgccc     120
gcatcaacca ggccctcgcg ggcctgggaa gtgggtggat gatccatgtg gacgccgtgc     180
ggcgtcctgc tccgaactac gcggagcggg gcctgtcggc gttccctgac cgtctgacgg     240
cagcgattga agaagagcgc tcggtcttgc cttgctcgtc ggtgatgtac ttcaccagct     300
ccgcgaagtc gctcttcttg atggagcgca tggggacgtg cttggcaatc acgcgcaccc     360
cccggccgtt ttagcggcta aaaaagtcat ggctctgccc tcgggcggac cacgcccatc     420
atgaccttgc caagctcgtc ctgcttctct tcgatcttcg ccagcagggc gaggatcgtg     480
gcatcaccga accgcgccgt gcgcgggtcg tcggtgagcg agagtttcag caggccgccc     540
aggcggccca ggtcgccatt gatgcgggcc agctcgcgga cgtgctcata gtccacgacg     600
cccgtgattt tgtagccctg gccgacggcc agcaggtagg ccgacaggct catgccggcc     660
gccgccgcct tttcctcaat cgctcttcgt tcgtctggaa ggcagtacac cttgataggt     720
gggctgccct tcctggttgg cttggtttca tcagccatcc gcttgccctc atctgttacg     780
ccggcggtag ccggccagcc tcgcagagca ggattcccgt tgagcaccgc caggtgcgaa     840
```

```
taagggacag tgaagaagga acacccgctc gcgggtgggc ctacttcacc tatcctgccc    900
ggctgacgcc gttggataca ccaaggaaag tctacacgaa cccctttggca aaatcctgta    960 tatcgtgcga aaaaggatgg atataccgaa aaaatcgcta taatgacccc gaagcagggt   1020
tatgcagcgg aaaagcgctg cttccctgct gttttgtgga atatctaccg actggaaaca   1080
ggcaaatgca ggaaattact gaactgaggg gacaggcgag agacgatgcc aaagagctac   1140
accgacgagc tggccgagtg ggttgaatcc cgcgcggcca agaagcgccg cgtgatgag    1200 gctgcggttg cgttcctggc ggtgagggcg gatgtcgagg cggcgttagc gtccggctat   1260
gcgctcgtca ccatttggga gcacatgcgg gaaacgggga aggtcaagtt ctcctacgag   1320
acgttccgct cgcacgccag gcggcacatc aaggccaagc ccgccgatgt gcccgcaccg   1380
caggccaagg ctgcggaacc cgcgccggca cccaagacgc cggagccacg gcggccgaag   1440
caggggggca aggctgaaaa gccggccccc gctgcggccc cgaccggctt caccttcaac   1500
ccaacaccgg acaaaaagga tctactgtaa tggcgaaaat tcacatggtt ttgcagggca   1560
agggcggggt cggcaagtcg gccatcgccg cgatcattgc gcagtacaag atggacaagg   1620
ggcagacacc cttgtgcatc gacaccgacc cggtgaacgc gacgttcgag ggctacaagg   1680
ccctgaacgt ccgccggctg aacatcatgg ccggcgacga aattaactcg cgcaacttcg   1740
acaccctggt cgagctgatt gcgccgacca aggatgacgt ggtgatcgac aacggtgcca   1800
gctcgttcgt gcctctgtcg cattacctca tcagcaacca ggtgccggct ctgctgcaag   1860
aaatggggca tgagctggtc atccataccg tcgtcaccgg cggccaggct ctcctggaca   1920
cggtgagcgg cttcgcccag ctcgccagcc agttcccggc cgaagcgctt ttcgtggtct   1980
ggctgaaccc gtattggggg cctatcgagc atgagggcaa gagctttgag cagatgaagg   2040
cgtacacggc caacaaggcc cgcgtgtcgt ccatcatcca gattccggcc tcaaggaag    2100 aaacctacgg ccgcgatttc agcgacatgc tgcaagagcg gctgacgttc gaccaggcgc   2160
tggccgatga atcgctcacg atcatgacgc ggcaacgcct caagatcgtg cggcgcggcc   2220
tgtttgaaca gctcgacgcg gcggccgtgc tatgagcgac cagattgaag agctgatccg   2280
ggagattgcg gccaagcacg gcatcgccgt cggccgcgac gacccggtgc tgatcctgca   2340
taccatcaac gcccggctca tggccgacag tgcggccaag caagaggaaa tccttgccgc   2400
gttcaaggaa gagctggaag ggatcgccca tcgttgggc gaggacgcca aggccaaagc    2460
ggagcggatg ctgaacgcgg ccctggcggc cagcaaggac gcaatggcga aggtaatgaa   2520
ggacagcgcc gcgcaggcgg ccgaagcgat ccgcagggaa atcgacacg gccttggccg     2580 ccagctcgcg gccaaggtcg cggacgcgcg gcgcgtggcg atgatgaaca tgatcgccgg   2640
cggcatggtt ttgttcgcgg ccgccctggt ggtgtgggcc tcgttatgaa tcgcagaggc   2700
gcagatgaaa aagcccggcg ttgccgggct ttgtttttgc gttagctggg cttgtttgac   2760
aggcccaagc tctgactgcg cccgcgctcg cgctcctggg cctgtttctt ctcctgctcc   2820
tgcttgcgca tcagggcctg gtgccgtcgg gctgcttcac gcatcgaatc ccagtcgccg   2880
gccagctcgg gatgctccgc gcgcatcttg cgcgtcgcca gttcctcgat cttgggcgcg   2940
tgaatgccca tgccttcctt gatttcgcgc accatgtcca gccgcgtgtg cagggtctgc   3000
aagcgggctt gctgttgggc ctgctgctgc tgccaggcgg cctttgtacg cggcagggac   3060
agcaagccgg gggcattgga ctgtagctgc tgcaaacgcg cctgctgacg gtctacgagc   3120
tgttctaggc ggtcctcgat gcgctccacc tggtcatgct ttgcctgcac gtagagcgca   3180
agggtctgct ggtaggtctg ctcgatgggc gcggattcta agagggcctg ctgttccgtc   3240
```

```
tcggcctcct gggccgcctg tagcaaatcc tcgccgctgt tgccgctgga ctgctttact    3300
gccggggact gctgttgccc tgctcgcgcc gtcgtcgcag ttcggcttgc ccccactcga    3360
ttgactgctt catttcgagc cgcagcgatg cgatctcgga ttgcgtcaac ggacggggca    3420
gcgcggaggt gtccggcttc tccttgggtg agtcggtcga tgccatagcc aaaggtttcc    3480
ttccaaaatg cgtccattgc tggaccgtgt ttctcattga tgcccgcaag catcttcggc    3540
ttgaccgcca ggtcaagcgc gccttcatgg gcggtcatga cggacgccgc catgaccttg    3600
ccgccgttgt tctcgatgta gccgcgtaat gaggcaatgg tgccgcccat cgtcagcgtg    3660
tcatcgacaa cgatgtactt ctggccgggg atcacctccc cctcgaaagt cgggttgaac    3720
gccaggcgat gatctgaacc ggctccggtt cgggcgacct tctcccgctg cacaatgtcc    3780
gtttcgacct caaggccaag gcggtcggcc agaacgaccg ccatcatggc cggaatcttg    3840
ttgttccccg ccgcctcgac ggcgaggact ggaacgatgc ggggcttgtc gtcgccgatc    3900
agcgtcttga gctgggcaac agtgtcgtcc gaaatcaggc gctcgaccaa attaagcgcc    3960
gcttccgcgt cgccctgctt cgcagcctgg tattcaggct cgttggtcaa agaaccaagg    4020
tcgccgttgc gaaccacctt cgggaagtct ccccacggtg cgcgctcggc tctgctgtag    4080
ctgctcaaga cgcctcccct tttagccgct aaaactctaa cgagtgcgcc cgcgactcaa    4140
cttgacgctt tcggcactta cctgtgcctt gccacttgcg tcataggtga tgcttttcgc    4200
actcccgatt tcaggtactt tatcgaaatc tgaccgggcg tgcattacaa agttcttccc    4260
cacctgttgg taaatgctgc cgctatctgc gtggacgatg ctgccgtcgt ggcgctgcga    4320
cttatcggcc ttttgggcca tatagatgtt gtaaatgcca ggtttcaggg ccccggcttt    4380
atctaccttc tggttcgtcc atgcgccttg gttctcggtc tggacaattc tttgcccatt    4440
catgaccagg aggcggtgtt tcattgggtg actcctgacg gttgcctctg tgttaaacg     4500
tgtcctggtc gcttgccggc taaaaaaaag ccgacctcgg cagttcgagg ccggcttttcc    4560
ctagagccgg gcgcgtcaag gttgttccat ctatttagt gaactgcgtt cgatttatca    4620
gttactttcc tcccgctttg tgtttcctcc cactcgtttc cgcgtctagc cgacccctca    4680
acatagcggc ctcttcttgg gctgcctttg cctcttgccg cgcttcgtca cgctcggctt    4740
gcaccgtcgt aaagcgctcg gcctgcctgg ccgcctcttg cgccgccaac ttcctttgct    4800
cctggtgggc ctcggcgtcg gcctgcgcct tcgctttcac cgctgccaac tccgtgcgca    4860
aactctccgc ttcgcgcctg gtggcgtcgc gctcgccgcg aagcgcctgc atttcctggt    4920
tggccgcgtc cagggtcttg cggctctctt ctttgaatgc gcgggcgtcc tggtgagcgt    4980
agtccagctc ggcgcgcagc tcctgcgctc gacgctccac ctcgtcggcc gctgcgtcg     5040
ccagcgcggc ccgctgctcg gctcctgcca gggcggtgcg tgcttcggcc agggcttgcc    5100
gctggcgtgc ggccagctcg gccgcctcgg cggcctgctg ctctagcaat gtaacgcgcg    5160
cctgggcttc ttccagctcg cgggcctgcg cctcgaaggc gtcggccagc tcccgcgca    5220
cggcttccaa ctcgttgcgc tcacgatccc agccggcttg cgctgcctgc aacgattcat    5280
tgcaagggc ctgggcggct tgccagaggg cggccacggc ctggttgccg gcctgctgca    5340
ccgcgtccgg cacctggact gccagcgggg cggcctgcgc cgtgcgctgg cgtcgccatt    5400
cgcgcatgcc ggcgctggcg tcgttcatgt tgacgcgggc ggccttacgc actgcatcca    5460
cggtcgggaa gttctcccgg tcgccttgct cgaacagctc gtccgcagcc gcaaaaatgc    5520
ggtcgcgcgt ctctttgttc agttccatgt tggctccggt aattggtaag aataataata    5580
```

-continued

```
ctcttaccta cottatcagc gcaagagttt agctgaacag ttctcgactt aacggcaggt    5640
tttttagcgg ctgaagggca ggcaaaaaaa gccccgcacg gtcggcgggg gcaaagggtc    5700
agcgggaagg ggattagcgg gcgtcgggct tcttcatgcg tcgggccgc gcttcttggg     5760 atggagcacg acgaagcgcg cacgcgcatc gtcctcggcc ctatcggccc gcgtcgcggt    5820
caggaacttg tcgcgcgcta ggtcctccct ggtgggcacc aggggcatga actcggcctg    5880
ctcgatgtag gtccactcca tgaccgcatc gcagtcgagg ccgcgttcct tcaccgtctc    5940
ttgcaggtcg cggtacgccc gctcgttgag cggctggtaa cgggccaatt ggtcgtaaat    6000
ggctgtcggc catgagcggc cttcctgtt gagccagcag ccgacgacga agccggcaat    6060
gcaggcccct ggcacaacca ggccgacgcc ggggcaggg gatggcagca gctcgccaac    6120 caggaaccc gccgcgatga tgccgatgcc ggtcaaccag cccttgaaac tatccggccc    6180
cgaaacaccc ctgcgcattg cctggatgct gcgccggata gcttgcaaca tcaggagccg    6240
tttcttttgt tcgtcagtca tggtccgccc tcaccagttg ttcgtatcgg tgtcggacga    6300
actgaaatcg caagagctgc cggtatcggt ccagccgctg tccgtgtcgc tgctgccgaa    6360
gcacggcgag gggtccgcga acgccgcaga cggcgtatcc ggccgcagcg catcgcccag    6420 catgccccg gtcagcgagc cgccggccag gtagcccagc atggtgctgt tggtcgcccc    6480
ggccaccagg gccgacgtga cgaaatcgcc gtcattccct ctggattgtt cgctgctcgg    6540
cggggcagtg cgccgcgccg gggcgtcgt ggatggctcg ggttggctgg cctgcgacgg    6600
ccggcgaaag gtgcgcagca gctcgttatc gaccggctgc ggcgtcgggg ccgccgcctt    6660
gcgctgcggt cggtgttcct tcttcggctc gcgcagcttg aacagcatga tcgcggaaac    6720
cagcagcaac gccgcgccta cgcctcccgc gatgtagaac agcatcggat tcattcttcg    6780
gtcctccttg tagcggaacc gttgtctgtg cggcgcgggt ggcccgcgcc gctgtctttg    6840
gggatcagcc ctcgatgagc gcgaccagtt tcacgtcggc aaggttcgcc tcgaactcct    6900
ggccgtcgtc ctcgtacttc aaccaggcat agccttccgc cggcggccga cggttgagga    6960
taaggcgggc agggcgctcg tcgtgctcga cctggacgat ggcctttttc agcttgtccg    7020
ggtccggctc cttcgcgccc ttttccttgg cgtccttacc gtcctggtcg ccgtcctcgc    7080
cgtcctggcc gtcgccggcc tccgcgtcac gctcggcatc agtctggccg ttgaaggcat    7140
cgacggtgtt gggatcgcgg cccttctcgt ccaggaactc gcgcagcagc ttgaccgtgc    7200
cgcgcgtgat ttcctgggtg tcgtcgtcaa gccacgcctc gacttcctcc gggcgcttct    7260
tgaaggccgt caccagctcg ttcaccacgg tcacgtcgcg cacgcggccg gtgttgaacg    7320
catcggcgat cttctccggc aggtccagca gcgtgacgtg ctgggtgatg aacgccggcg    7380
acttgccgat ttccttggcg atatcgcctt tcttcttgcc cttcgccagc tcgcggccaa    7440
tgaagtcggc aatttcgcgc ggggtcagct cgttgcgttg caggttctcg ataacctggt    7500
cggcttcgtt gtagtcgttg tcgatgaacg ccgggatgga cttcttgccg gcccacttcg    7560
agccacggta gcggcgggcg ccgtgattga tgatatagcg gcccggctgc tcctggttct    7620
cgcgcaccga aatgggtgac ttcaccccgc gctctttgat cgtggcaccg atttccgcga    7680
tgctctccgg ggaaaagccg gggttgtcgg ccgtccgcgg ctgatgcgga tcttcgtcga    7740
tcaggtccag gtccagctcg atagggccgg aaccgccctg agacgccgca ggagcgtcca    7800
ggaggctcga caggtcgccg atgctatcca accccaggcc ggacggctgc ccgcgcctg    7860 cggcttcctg agcggccgca gcggtgtttt tcttggtggt cttggcttga gccgcagtca    7920
ttgggaaatc tccatcttcg tgaacacgta atcagccagg gcgcgaacct ctttcgatgc    7980
```

```
cttgcgcgcg gccgttttct tgatcttcca gaccggcaca ccggatgcga gggcatcggc    8040
gatgctgctg cgcaggccaa cggtggccgg aatcatcatc ttggggtacg cggccagcag    8100
ctcggcttgg tggcgcgcgt ggcgcggatt ccgcgcatcg accttgctgg gcaccatgcc    8160
aaggaattgc agcttggcgt tcttctggcg cacgttcgca atggtcgtga ccatcttctt    8220
gatgccctgg atgctgtacg cctcaagctc gatggggac agcacatagt cggccgcgaa     8280
gagggcggcc gccaggccga cgccaagggt cggggccgtg tcgatcaggc acacgtcgaa    8340
gccttggttc gccagggcct tgatgttcgc cccgaacagc tcgcgggcgt cgtccagcga    8400
cagccgttcg gcgttcgcca gtaccgggtt ggactcgatg agggcgaggc gcgcggcctg    8460
gccgtcgccg gctgcgggtg cggtttcggt ccagccgccg gcaggacag cgccgaacag     8520 cttgcttgca tgcaggccgg tagcaaagtc cttgagcgtg taggacgcat tgccctgggg    8580
gtccaggtcg atcacggcaa cccgcaagcc gcgctcgaaa aagtcgaagg caagatgcac    8640
aagggtcgaa gtcttgccga cgccgccttt ctggttggcc gtgaccaaag ttttcatcgt    8700
ttggtttcct gttttttctt ggcgtccgct tcccacttcc ggacgatgta cgcctgatgt    8760
tccggcagaa ccgccgttac ccgcgcgtac ccctcgggca agttcttgtc ctcgaacgcg    8820
gcccacacgc gatgcaccgc ttgcgacact gcgccctgg tcagtcccag cgacgttgcg     8880
aacgtcgcct gtggcttccc atcgactaag acgcccgcg ctatctcgat ggtctgctgc     8940
cccacttcca gccccgtgat cgcctcctgg aactggcttt cggtaagccg tttcttcatg    9000
gataacaccc ataatttgct ccgcgccttg gttgaacata gcggtgacag ccgccagcac    9060
atgagagaag tttagctaaa catttctcgc acgtcaacac ctttagccgc taaaactcgt    9120
ccttggcgta acaaaacaaa agcccggaaa ccgggctttc gtctcttgcc gcttatggct    9180
ctgcacccgg ctccatcacc aacaggtcgc gcacgcgctt cactcggttg cggatcgaca    9240
ctgccagccc aacaaagccg gttgccgccg ccgccaggat cgcgccgatg atgccggcca    9300
caccggccat cgcccaccag gtcgccgcct tccggttcca ttcctgctgg tactgcttcg    9360
caatgctgga cctcggctca ccataggctg accgctcgat ggcgtatgcc gcttctcccc    9420
ttggcgtaaa acccagcgcc gcaggcggca ttgccatgct gcccgccgct ttcccgacca    9480
cgacgcgcgc accaggcttg cggtccagac cttcggccac ggcgagctgc gcaaggacat    9540
aatcagccgc cgacttggct ccacgcgcct cgatcagctc ttgcactcgc gcgaaatcct    9600
tggcctccac ggccgccatg aatcgcgcac gcggcgaagg ctccgcaggg ccggcgtcgt    9660
gatcgccgcc gagaatgccc ttcaccaagt tcgacgcac gaaaatcatg ctgacggcta     9720
tcaccatcat gcagacggat cgcacgaacc cgctgaattg aacacgagca cggcacccgc    9780
gaccactatg ccaagaatgc ccaaggtaaa aattgccggc cccgccatga agtccgtgaa    9840
tgccccgacg gccgaagtga agggcaggcc gccacccagg ccgccgccct cactgcccgg    9900
cacctggtcg ctgaatgtcg atgccagcac ctgcggcacg tcaatgcttc cgggcgtcgc    9960
gctcgggctg atcgcccatc ccgttactgc cccgatcccg gcaatggcaa ggactgccag   10020
cgctgccatt tttggggtga ggccgttcgc ggccgagggg cgcagcccct gggggggatgg   10080 gaggcccgcg ttagcgggcc gggagggttc gagaaggggg ggcaccccccc ttcggcgtgc   10140 gcggtcacgc gcacagggcg cagccctggt taaaaacaag gtttataaat attggtttaa   10200
aagcaggtta aaagacaggt tagcggtggc cgaaaaacgg gcggaaaccc ttgcaaatgc   10260 tggatttct gcctgtggac agcccctcaa atgtcaatag gtgcgcccct catctgtcag    10320
```

-continued

```
cactctgccc ctcaagtgtc aaggatcgcg ccactcatct gtcagtagtc gcgcccctca   10380
agtgtcaata ccgcagggca cttatcccca ggcttgtcca catcatctgt gggaaactcg   10440
cgtaaaatca ggcgttttcg ccgatttgcg aggctggcca gctccacgtc gccggccgaa   10500
atcgagcctg cccctcatct gtcaacgccg cgccgggtga gtcggcccct caagtgtcaa   10560
cgtccgcccc tcatctgtca gtgagggcca agttttccgc gaggtatcca caacgccggc   10620
ggccgcggtg tctcgcacac ggcttcgacg gcgtttctgg cgcgtttgca gggccataga   10680
cggccgccag cccagcggcg agggcaacca gcccggtgag cgtcggaaag gcgctggaag   10740
ccccgtagcg acgcggagag gggcgagaca agccaagggc gcaggctcga tgcgcagcac   10800
gacatagccg gttctcgcaa ggacgagaat ttccctgcgg tgcccctcaa gtgtcaatga   10860
aagtttccaa cgcgagccat cgcgagagc cttgagtcca cgctagatga gagctttgtt   10920
gtaggtggac cagttggtga ttttgaactt ttgctttgcc acggaacggt ctgcgttgtc   10980
gggaagatgc gtgatctgat ccttcaactc agcaaaagtt cgatttattc aacaaagcca   11040
cgttgtgtct caaaatctct gatgttacat tgcacaagat aaaatatat catcatgaac   11100
aataaaactg tctgcttaca taaacagtaa tacaaggggt gttatgagcc atattcaacg   11160
ggaacgtct tgctcgactc tagagctcgt tcctcgaggc ctcgaggcct cgaggaacgg   11220
tacctgcggg gaagcttaca ataatgtgtg ttgttaagtc ttgttgcctg tcatcgtctg   11280
actgactttc gtcataaatc ccggcctccg taacccagct ttgggcaagc tcacggattt   11340
gatccggcgg aacgggaata tcgagatgcc gggctgaacg ctgcagttcc agctttccct   11400
ttcgggacag gtactccagc tgattgatta tctgctgaag gtcttggtt ccacctcctg   11460
gcacaatgcg aatgattact tgagcgcgat cgggcatcca attttctccc gtcaggtgcg   11520
tggtcaagtg ctacaaggca cctttcagta acgagcgacc gtcgatccgt cgccgggata   11580
cggacaaaat ggagcgcagt agtccatcga gggcggcgaa agcctcgcca aaagcaatac   11640
gttcatctcg cacagcctcc agatccgatc gagggtcttc ggcgtaggca gatagaagca   11700
tggatacatt gcttgagagt attccgatgg actgaagtat ggcttccatc ttttctcgtg   11760
tgtctgcatc tatttcgaga aagccccga tgccgcgcac cgcaacgcga attgccatac   11820
tatccgaaag tcccagcagg cgcgcttgat aggaaaaggt ttcatactcg gccgatcgca   11880
gacgggcact cacgaccttg aacccttcaa cttttcaggga tcgatgctgg ttgatggtag   11940
tctcactcga cgtggctctg gtgtgttttg acatagcttc ctccaaagaa agcggaaggt   12000
ctggatactc cagcacgaaa tgtgcccggg tagacggatg gaagtctagc cctgctcaat   12060
atgaaatcaa cagtacattt acagtcaata ctgaatatac ttgctacatt tgcaattgtc   12120
ttataacgaa tgtgaaataa aaatagtgta acaacgcttt tactcatcga taatcacaaa   12180
aacatttata cgaacaaaaa tacaaatgca ctccggtttc acaggatagg cgggatcaga   12240
atatgcaact tttgacgttt tgttctttca aaggggtgc tggcaaaacc accgcactca   12300
tgggcctttg cgctgctttg gcaaatgacg gtaaacgagt ggccctcttt gatgccgacg   12360
aaaaccggcc tctgacgcga tggagagaaa acgccttaca aagcagtact gggatcctcg   12420
ctgtgaagtc tattccgccg acgaaatgcc ccttcttgaa gcagcctatg aaaatgccga   12480
gctcgaagga tttgattatg cgttggccga tacgcgtggc ggctcgagcg agctcaacaa   12540
cacaatcatc gctagctcaa acctgcttct gatcccacc atgctaacgc cgctcgacat   12600
cgatgaggca ctatctacct accgctacgt catcgagctg ctgttgagtg aaaatttggc   12660
aattcctaca gctgttttgc gccaacgcgt cccggtcggc cgattgacaa catcgcaacg   12720
```

```
caggatgtca gagacgctag agagccttcc agttgtaccg tctcccatgc atgaaagaga   12780
tgcatttgcc gcgatgaaag aacgcggcat gttgcatctt acattactaa acacgggaac   12840
tgatccgacg atgcgcctca tagagaggaa tcttcggatt gcgatggagg aagtcgtggt   12900
catttcgaaa ctgatcagca aaatcttgga ggcttgaaga tggcaattcg caagcccgca   12960
ttgtcggtcg gcgaagcacg gcggcttgct ggtgctcgac ccgagatcca ccatcccaac   13020
ccgacacttg ttccccagaa gctggacctc cagcacttgc ctgaaaaagc cgacgagaaa   13080
gaccagcaac gtgagcctct cgtcgccgat cacatttaca gtcccgatcg acaacttaag   13140
ctaactgtgg atgcccttag tccacctccg tccccgaaaa agctccaggt ttttcttttca   13200 gcgcgaccgc ccgcgcctca agtgtcgaaa acatatgaca acctcgttcg gcaatacagt   13260
ccctcgaagt cgctacaaat gattttaagg cgcgcgttgg acgatttcga aagcatgctg   13320
gcagatggat catttcgcgt ggccccgaaa agttatccga tcccttcaac tacagaaaaa   13380
tccgttctcg ttcagacctc acgcatgttc ccggttgcgt tgctcgaggt cgctcgaagt   13440
cattttgatc cgttggggtt ggagaccgct cgagctttcg gccacaagct ggctaccgcc   13500
gcgctcgcgt cattctttgc tggagagaag ccatcgagca attggtgaag agggacctat   13560
cggaacccct caccaaatat tgagtgtagg tttgaggccg ctggccgcgt cctcagtcac   13620
cttttgagcc agataattaa gagccaaatg caattggctc aggctgccat cgtcccccccg   13680 tgcgaaacct gcacgtccgc gtcaaagaaa taaccggcac ctcttgctgt ttttatcagt   13740
tgagggcttg acggatccgc ctcaagtttg cggcgcagcc gcaaaatgag aacatctata   13800
ctcctgtcgt aaacctcctc gtcgcgtact cgactggcaa tgagaagttg ctcgcgcgat   13860
agaacgtcgc ggggtttctc taaaaacgcg aggagaagat tgaactcacc tgccgtaagt   13920
ttcacctcac cgccagcttc ggacatcaag cgacgttgcc tgagattaag tgtccagtca   13980
gtaaaacaaa aagaccgtcg gtctttggag cggacaacgt tggggcgcac gcgcaaggca   14040
acccgaatgc gtgcaagaaa ctctctcgta ctaaacggct tagcgataaa atcacttgct   14100
cctagctcga gtgcaacaac tttatccgtc tcctcaaggc ggtcgccact gataattatg   14160
attggaatat cagactttgc cgccagattt cgaacgatct caagcccatc ttcacgacct   14220
aaatttagat caacaaccac gacatcgacc gtcgcggaag agagtactct agtgaactgg   14280
gtgctgtcgg ctaccgcggt cactttgaag gcgtggatcg taaggtattc gataataaga   14340
tgccgcatag cgacatcgtc atcgataaga agaacgtgtt tcaacggctc acctttcaat   14400
ctaaaatctg aacccttgtt cacagcgctt gagaaatttt cacgtgaagg atgtacaatc   14460
atctccagct aaatgggcag ttcgtcagaa ttgcggctga ccgcggatga cgaaaatgcg   14520
aaccaagtat ttcaattta tgacaaaagt tctcaatcgt tgttacaagt gaaacgcttc   14580
gaggttacag ctactattga ttaaggagat cgcctatggt ctcgccccgg cgtcgtgcgt   14640
ccgccgcgag ccagatctcg cctacttcat aaacgtcctc ataggcacgg aatgaaatga   14700
tgacatcgat cgccgtagag agcatgtcaa tcagtgtgcg atcttccaag ctagcacctt   14760
gggcgctact tttgacaagg gaaaacagtt tcttgaatcc ttggattgga ttcgcgccgt   14820
gtattgttga aatcgatccc ggatgtcccg agacgacttc actcagataa gcccatgctg   14880
catcgtcgcg catctcgcca agcaatatcc ggtccggccg catacgcaga cttgcttgga   14940
gcaagtgctc ggcgctcaca gcacccagcc cagcaccgtt cttggagtag agtagtctaa   15000
catgattatc gtgtggaatg acgagttcga gcgtatcttc tatggtgatt agccttttcct   15060
```

```
ggggggggat ggcgctgatc aaggtcttgc tcattgttgt cttgccgctt ccggtagggc   15120
cacatagcaa catcgtcagt cggctgacga cgcatgcgtg cagaaacgct tccaaatccc   15180
cgttgtcaaa atgctgaagg atagcttcat catcctgatt ttggcgtttc cttcgtgtct   15240
gccactggtt ccacctcgaa gcatcataac gggaggagac ttctttaaga ccagaaacac   15300
gcgagcttgg ccgtcgaatg gtcaagctga cggtgcccga gggaacggtc ggcggcagac   15360
agatttgtag tcgttcacca ccaggaagtt cagtggcgca gagggggtta cgtggtccga   15420
catcctgctt tctcagcgcg cccgctaaaa tagcgatatc ttcaagatca tcataagaga   15480
cgggcaaagg catcttggta aaatgccgg cttggcgcac aaatgcctct ccaggtcgat   15540
tgatcgcaat ttcttcagtc ttcgggtcat cgagccattc caaaatcggc ttcagaagaa   15600
agcgtagttg cggatccact tccatttaca atgtatccta tctctaagcg gaaatttgaa   15660
ttcattaaga gcggcggttc ctcccccgcg tggcgccgcc agtcaggcgg agctggtaaa   15720
caccaaagaa atcgaggtcc cgtgctacga aaatggaaac ggtgtcaccc tgattcttct   15780
tcagggttgg cggtatgttg atggttgcct taagggctgt ctcagttgtc tgctcaccgt   15840
tattttgaaa gctgttgaag ctcatcccgc cacccgagct gccggcgtag gtgctagctg   15900
cctggaaggc gccttgaaca acactcaaga gcatagctcc gctaaaacgc tgccagaagt   15960
ggctgtcgac cgagcccggc aatcctgagc gaccgagttc gtccgcgctt ggcgatgtta   16020
acgagatcat cgcatggtca ggtgtctcgg cgcgatccca caacacaaaa acgcgcccat   16080
ctccctgttg caagccacgc tgtatttcgc caacaacggt ggtgccacga tcaagaagca   16140
cgatattgtt cgttgttcca cgaatatcct gaggcaagac acactttaca tagcctgcca   16200
aatttgtgtc gattgcggtt tgcaagatgc acggaattat tgtcccttgc gttaccataa   16260
aatcggggtg cggcaagagc gtggcgctgc tgggctgcag ctcggtgggt ttcatacgta   16320
tcgacaaatc gttctcgccg gacacttcgc cattcggcaa ggagttgtcg tcacgcttgc   16380
cttcttgtct tcggcccgtg tcgccctgaa tggcgcgttt gctgacccct tgatcgccgc   16440
tgctatatgc aaaaatcggt gtttcttccg gccgtggctc atgccgctcc ggttcgcccc   16500
tcggcggtag aggagcagca ggctgaacag cctcttgaac cgctggagga tccggcggca   16560
cctcaatcgg agctggatga aatggcttgg tgtttgttgc gatcaaagtt gacggcgatg   16620
cgttctcatt caccttcttt tggcgcccac ctagccaaat gaggcttaat gataacgcga   16680
gaacgacacc tccgacgatc aatttctgag accccgaaag acgccggcga tgtttgtcgg   16740
agaccaggga tccagatgca tcaacctcat gtgccgcttg ctgactatcg ttattcatcc   16800
cttcgccccc ttcaggacgc gtttcacatc gggcctcacc gtgcccgttt gcggcctttg   16860
gccaacggga tcgtaagcgg tgttccagat acatagtact gtgtggccat ccctcagacg   16920
ccaacctcgg gaaaccgaag aaatctcgac atcgctccct ttaactgaat agttggcaac   16980
agcttccttg ccatcaggat tgatggtgta gatggagggt atgcgtacat tgcccggaaa   17040
gtggaatacc gtcgtaaatc cattgtcgaa gacttcgagt ggcaacagcg aacgatcgcc   17100
ttgggcgacg tagtgccaat tactgtccgc cgcaccaagg gctgtgacag gctgatccaa   17160
taaattctca gctttccgtt gatattgtgc ttccgcgtgt agtctgtcca caacagcctt   17220
ctgttgtgcc tcccttcgcc gagccgccgc atcgtcggcg gggtaggcga attggacgct   17280
gtaatagaga tcgggctgct ctttatcgag gtgggacaga gtcttggaac ttatactgaa   17340
aacataacgg cgcatcccgg agtcgcttgc ggttagcacg attactggct gaggcgtgag   17400
gacctggctt gccttgaaaa atagataatt tccccgcggt agggctgcta gatctttgct   17460
```

```
atttgaaacg gcaaccgctg tcaccgtttc gttcgtggcg aatgttacga ccaaagtagc   17520
tccaaccgcc gtcgagaggc gcaccacttg atcgggattg taagccaaat aacgcatgcg   17580
cggatctagc ttgcccgcca ttggagtgtc ttcagcctcc gcaccagtcg cagcggcaaa   17640
taaacatgct aaaatgaaaa gtgctttcct gatcatggtt cgctgtggcc tacgtttgaa   17700
acggtatctt ccgatgtctg ataggaggtg acaaccagac ctgccgggtt ggttagtctc   17760
aatctgccgg gcaagctggt caccttttcg tagcgaactg tcgcggtcca cgtactcacc   17820
acaggcattt tgccgtcaac gacgagggtc cttttatagc gaatttgctg cgtgcttgga   17880
gttacatcat ttgaagcgat gtgctcgacc tccaccctgc cgcgtttgcc aagaatgact   17940
tgaggcgaac tgggattggg atagttgaag aattgctggt aatcctggcg cactgttggg   18000
gcactgaagt tcgataccag gtcgtaggcg tactgagcgg tgtcggcatc ataactctcg   18060
cgcaggcgaa cgtactccca caatgaggcg ttaacgacgg cctcctcttg agttgcaggc   18120
aatcgcgaga cagacacctc gctgtcaacg gtgccgtccg gccgtatcca tagatatacg   18180
ggcacaagcc tgctcaacgg caccattgtg gctatagcga acgcttgagc aacatttccc   18240
aaaatcgcga tagctgcgac agctgcaatg agtttggaga gacgtcgcgc cgatttcgct   18300
cgcgcggttt gaaaggcttc tacttcctta tagtgctcgg caaggctttc gcgcgccact   18360
agcatggcat attcaggccc cgtcatagcg tccacccgaa ttgccgagct gaagatctga   18420
cggagtaggc tgccatcgcc ccacattcag cgggaagatc gggcctttgc agctcgctaa   18480
tgtgtcgttt gtctggcagc cgctcaaagc gacaactagg cacagcaggc aatacttcat   18540
agaattctcc attgaggcga atttttgcgc gacctagcct cgctcaacct gagcgaagcg   18600
acggtacaag ctgctggcag attgggttgc gccgctccag taactgcctc caatgttgcc   18660
ggcgatcgcc ggcaaagcga caatgagcgc atccctgtc agaaaaaaca tatcgagttc   18720
gtaaagacca atgatcttgg ccgcggtcgt accggcgaag gtgattacac caagcataag   18780
ggtgagcgca gtcgcttcgg ttaggatgac gatcgttgcc acgagtttta agaggagaag   18840
caagagaccg taggtgataa gttgcccgat ccactagct gcgatgtccc gcgtgcgatc   18900
aaaaatatat ccgacgagga tcagaggccc gatcgcgaga agcactttcg tgagaattcc   18960
aacggcgtcg taaactccga aggcagacca gagcgtgccg taaaggaccc actgtgcccc   19020
ttggaaagca aggatgtcct ggtcgttcat cggaccgatt tcggatgcga tttttctgaaa   19080 aacggcctgg gtcacggcga acattgtatc caactgtgcc ggaacagtct gcagaggcaa   19140
gccggttaca ctaaactgct gaacaaagtt tgggaccgtc ttttcgaaga tggaaaccac   19200
atagtcttgg tagttagcct gcccaacaat tagagcaaca acgatggtga ccgtgatcac   19260
ccgagtgata ccgctacggg tatcgacttc gccgcgtatg actaaaatac cctgaacaat   19320
aatccaaaga gtgacacagg cgatcaatgg cgcactcacc gcctcctgga tagtctcaag   19380
catcgagtcc aagcctgtcg tgaaggctac atcgaagatc gtatgaatgg ccgtaaacgg   19440
cgccggaatc gtgaaattca tcgattggac ctgaacttga ctggtttgtc gcataatgtt   19500
ggataaaatg agctcgcatt cggcgaggat gcggcggat gaacaaatcg cccagcctta   19560
ggggagggca ccaaagatga cagcggtctt ttgatgctcc ttgcgttgag cggccgcctc   19620
ttccgcctcg tgaaggccgg cctgcgcggt agtcatcgtt aataggcttg tcgcctgtac   19680
attttgaatc attgcgtcat ggatctgctt gagaagcaaa ccattggtca cggttgcctg   19740
catgatattg cgagatcggg aaagctgagc agacgtatca gcattcgccg tcaagcgttt   19800
```

```
gtccatcgtt tccagattgt cagccgcaat gccagcgctg tttgcggaac cggtgatctg   19860
cgatcgcaac aggtccgctt cagcatcact acccacgact gcacgatctg tatcgctggt   19920
gatcgcacgt gccgtggtcg acattggcat tcgcggcgaa acatttcat tgtctaggtc    19980 cttcgtcgaa ggatactgat ttttctggtt gagcgaagtc agtagtccag taacgccgta   20040
ggccgacgtc aacatcgtaa ccatcgctat agtctgagtg agattctccg cagtcgcgag   20100
cgcagtcgcg agcgtctcag cctccgttgc cgggtcgcta acaacaaact gcgcccgcgc   20160
gggctgaata tatagaaagc tgcaggtcaa aactgttgca ataagttgcg tcgtcttcat   20220
cgtttcctac cttatcaatc ttctgcctcg tggtgacggg ccatgaattc gctgagccag   20280
ccagatgagt tgccttcttg tgcctcgcgt agtcgagttg caaagcgcac cgtgttggca   20340
cgccccgaaa gcacggcgac atattcacgc atatcccgca gatcaaattc gcagatgacg   20400
cttccacttt ctcgtttaag aagaaactta cggctgccga ccgtcatgtc ttcacggatc   20460
gcctgaaatt ccttttcggt acatttcagt ccatcgacat aagccgatcg atctgcggtt   20520
ggtgatggat agaaaatctt cgtcatacat tgcgcaacca agctggctcc tagcggcgat   20580
tccagaacat gctctggttg ctgcgttgcc agtattagca tcccgttgtt ttttcgaacg   20640
gtcaggagga atttgtcgac gacagtcgaa aatttagggt ttaacaaata ggcgcgaaac   20700
tcatcgcagc tcatcacaaa acggcggccg tcgatcatgg ctccaatccg atgcaggaga   20760
tatgctgcag cgggagcgca tacttcctcg tattcgagaa gatgcgtcat gtcgaagccg   20820
gtaatcgacg gatctaactt tacttcgtca acttcgccgt caaatgccca gccaagcgca   20880
tggccccggc accagcgttg gagccgcgct cctgcgcctt cggcgggccc atgcaacaaa   20940
aattcacgta accccgcgat tgaacgcatt tgtggatcaa acgagagctg acgatggata   21000
ccacggacca gacggcggtt ctcttccgga gaaatcccac cccgaccatc actctcgatg   21060
agagccacga tccattcgcg cagaaaatcg tgtgaggctg ctgtgttttc taggccacgc   21120
aacgcgccca cccgctgggt gtgcctctg tgaagtgcca aatatgttcc tcctgtggcg    21180
cgaaccagca attcgccacc ccggtccttg tcaaagaaca cgaccgtacc tgcacggtcg   21240
accatgctct gttcgagcat ggctagaaca aacatcatga gcgtcgtctt acccctcccg   21300
ataggcccga atattgccgt catgccaaca tcgtgctcat gcgggatata gtcgaaaggc   21360
gttccgccat tggtacgaaa tcgggcaatc gcgttgcccc agtggcctga gctggcgccc   21420
tctggaaagt tttcgaaaga gacaaaccct gcgaaattgc gtgaagtgat tgcgccaggg   21480
cgtgtgcgcc acttaaaatt ccccggcaat tgggaccaat aggccgcttc cataccaata   21540
ccttcttgga caaccacggc acctgcatcc gccattcgtg tccgagcccg cgcgcccctg   21600
tccccaagac tattgagatc gtctgcatag acgcaaaggc tcaaatgatg tgagcccata   21660
acgaattcgt tgctcgcaag tgcgtcctca gcctcggata atttgccgat ttgagtcacg   21720
gctttatcgc cggaactcag catctcggctc gatttgaggc taagtttcgc gtgcgcttgc   21780
gggcgagtca ggaacgaaaa actctgcgtg agaacaagtg gaaaatcgag ggatagcagc   21840
gcgttgagca tgcccggccg tgttttgca gggtattcgc gaaacgaata gatggatcca    21900
acgtaactgt cttttggcgt tctgatctcg agtcctcgct tgccgcaaat gactctgtcg   21960
gtataaatcg aagcgccgag tgagccgctg acgaccggaa ccggtgtgaa ccgaccagtc   22020
atgatcaacc gtagcgcttc gccaatttcg gtgaagagca cccctgctt ctcgcggatg    22080 ccaagacgat gcaggccata cgctttaaga gagccagcga caacatgcca aagatcttcc   22140
atgttcctga tctggcccgt gagatcgttt tccctttttc cgcttagctt ggtgaacctc   22200
```

```
ctctttacct tccctaaagc cgcctgtggg tagacaatca acgtaaggaa gtgttcattg   22260
cggaggagtt ggccggagag cacgcgctgt tcaaaagctt cgttcaggct agcggcgaaa   22320
acactacgga agtgtcgcgg cgccgatgat ggcacgtcgg catgacgtac gaggtgagca   22380
tatattgaca catgatcatc agcgatattg cgcaacagcg tgttgaacgc acgacaacgc   22440
gcattgcgca tttcagtttc ctcaagctcg aatgcaacgc catcaattct cgcaatggtc   22500
atgatcgatc cgtcttcaag aaggacgata tggtcgctga ggtggccaat ataagggaga   22560
tagatctcac cggatctttc ggtcgttcca ctcgcgccga gcatcacacc attcctctcc   22620
ctcgtggggg aaccctaatt ggatttgggc taacagtagc gccccccaa actgcactat    22680 caatgcttct tcccgcggtc cgcaaaaata gcaggacgac gctcgccgca ttgtagtctc   22740
gctccacgat gagccgggct gcaaaccata acggcacgag aacgacttcg tagagcgggt   22800
tctgaacgat aacgatgaca aagccggcga acatcatgaa taaccctgcc aatgtcagtg   22860
gcaccccaag aaacaatgcg ggccgtgtgg ctgcgaggta aagggtcgat tcttccaaac   22920
gatcagccat caactaccgc cagtgagcgt ttggccgagg aagctcgccc caaacatgat   22980
aacaatgccg ccgacgacgc cggcaaccag cccaagcgaa gccgcccga acatccagga    23040 gatcccgata gcgacaatgc cgagaacagc gagtgactgg ccgaacggac caaggataaa   23100
cgtgcatata ttgttaacca ttgtggcggg gtcagtgccg ccacccgcag attgcgctgc   23160
ggcgggtccg gatgaggaaa tgctccatgc aattgcaccg cacaagcttg ggcgcagct    23220 cgatatcacg cgcatcatcg cattcgagag cgagaggcga tttagatgta acggtatct    23280 ctcaaagcat cgcatcaatg cgcacctcct tagtataagt cgaataagac ttgattgtcg   23340
tctgcggatt tgccgttgtc ctggtgtggc ggtggcggag cgattaaacc gccagcgcca   23400
tcctcctgcg agcggcgctg atatgacccc caaacatccc acgtctcttc ggattttagc   23460
gcctcgtgat cgtcttttgg aggctcgatt aacgcgggca ccagcgattg agcagctgtt   23520
tcaacttttc gcacgtagcc gtttgcaaaa ccgccgatga aattaccggt gttgtaagcg   23580
gagatcgccc gacgaagcgc aaattgcttc tcgtcaatcg tttcgccgcc tgcataacga   23640
cttttcagca tgtttgcagc ggcagataat gatgtgcacg cctggagcgc accgtcaggt   23700
gtcagaccga gcatagaaaa atttcgagag tttatttgca tgaggccaac atccagcgaa   23760
tgccgtgcat cgagacggtg cctgacgact tgggttgctt ggctgtgatc ttgccagtga   23820
agcgtttcgc cggtcgtgtt gtcatgaatc gctaaaggat caaagcgact ctccacctta   23880
gctatcgccc caagcgtaga tgtcgcaact gatgggcac acttgcgagc aacatggtca    23940
aactcagcag atgagagtgg cgtggcaagg ctcgacgaac agaaggagac catcaaggca   24000
agagaaagcg accccgatct cttaagcata ccttatctcc ttagctcgca actaacaccg   24060
cctctcccgt tggaagaagt gcgttgtttt atgttgaaga ttatcgggag ggtcggttac   24120
tcgaaaattt tcaattgctt ctttatgatt tcaattgaag cgagaaacct cgcccggcgt   24180
cttggaacgc aacatggacc gagaaccgcg catccatgac taagcaaccg gatcgaccta   24240
ttcaggccgc agttggtcag gtcaggctca gaacgaaaat gctcggcgag gttacgctgt   24300
ctgtaaaccc attcgatgaa cgggaagctt ccttccgatt gctcttggca ggaatattgg   24360
cccatgcctg cttgcgcttt gcaaatgctc ttatcgcgtt ggtatcatat gccttgtccg   24420
ccagcagaaa cgcactctaa gcgattattt gtaaaaatgt ttcggtcatg cggcggtcat   24480
gggcttgacc cgctgtcagc gcaagacgga tcggtcaacc gtcggcatcg acaacagcgt   24540
```

```
gaatcttggt ggtcaaaccg ccacgggaac gtcccataca gccatcgtct tgatcccgct    24600
gtttcccgtc gccgcatgtt ggtggacgcg gacacaggaa ctgtcaatca tgacgacatt    24660
ctatcgaaag ccttggaaat cacactcaga atatgatccc agacgtctgc ctcacgccat    24720
cgtacaaagc gattgtagca ggttgtacag gaaccgtatc gatcaggaac gtctgcccag    24780
ggcgggcccg tccggaagcg ccacaagatg acattgatca cccgcgtcaa cgcgcggcac    24840
gcgacgcggc ttatttggga acaaaggact gaacaacagt ccattcgaaa tcggtgacat    24900
caaagcgggg acgggttatc agtggcctcc aagtcaagcc tcaatgaatc aaaatcagac    24960
cgatttgcaa acctgattta tgagtgtgcg gcctaaatga tgaaatcgtc cttctagatc    25020
gcctccgtgg tgtagcaaca cctcgcagta tcgccgtgct gaccttggcc agggaattga    25080
ctggcaaggg tgcttttcaca tgaccgctct tttggccgcg atagatgatt tcgttgctgc    25140
tttgggcacg tagaaggaga gaagtcatat cggagaaatt cctcctggcg cgagagcctg    25200
ctctatcgcg acggcatccc actgtcggga acagaccgga tcattcacga ggcgaaagtc    25260
gtcaacacat gcgttatagg catcttccct tgaaggatga tcttgttgct gccaatctgg    25320
aggtgcggca gccgcaggca gatgcgatct cagcgcaact tgcggcaaaa catctcactc    25380
acctgaaaac cactagcgag tctcgcgatc agacgaaggc cttttactta acgacacaat    25440
atccgatgtc tgcatcacag gcgtcgctat cccagtcaat actaaagcgg tgcaggaact    25500
aaagattact gatgacttag gcgtgccacg aggcctgaga cgacgcgcgt agacagtttt    25560
ttgaaatcat tatcaaagtg atggcctccg ctgaagccta tcacctctgc gccggtctgt    25620
cggagagatg ggcaagcatt attacggtct tcgcgcccgt acatgcattg gacgattgca    25680
gggtcaatgg atctgagatc atccagagga ttgccgccct taccttccgt ttcgagttgg    25740
agccagcccc taaatgagac gacatagtcg acttgatgtg acaatgccaa gagagagatt    25800
tgcttaaccc gatttttttg ctcaagcgta agcctattga agcttgccgg catgacgtcc    25860
gcgccgaaag aatatcctac aagtaaaaca ttctgcacac cgaaatgctt ggtgtagaca    25920
tcgattatgt gaccaagatc cttagcagtt tcgcttgggg accgctccga ccagaaatac    25980
cgaagtgaac tgacgccaat gacaggaatc ccttccgtct gcagataggt accatcgata    26040
gatctgctgc ctcgcgcgtt tcggtgatga cggtgaaaac ctctgacaca tgcagctccc    26100
ggagacggtc acagcttgtc tgtaagcgga tgccgggagc agacaagccc gtcagggcgc    26160
gtcagcgggt gttggcgggt gtcggggcgc agccatgacc cagtcacgta gcgatagcgg    26220
agtgtatact ggcttaacta tgcggcatca gagcagattg tactgagagt gcaccatatg    26280
cggtgtgaaa taccgcacag atgcgtaagg agaaaatacc gcatcaggcg ctcttccgct    26340
tcctcgctca ctgactcgct gcgctcggtc gttcggctgc ggcgagcggt atcagctcac    26400
tcaaaggcgg taatacggtt atccacagaa tcaggggata acgcaggaaa gaacatgtga    26460
gcaaaaggcc agcaaaaggc caggaaccgt aaaaaggccg cgttgctggc gttttccat     26520 aggctccgcc cccctgacga gcatcacaaa aatcgacgct caagtcagag gtggcgaaac    26580
ccgacaggac tataaagata ccaggcgttt ccccctggaa gctccctcgt gcgctctcct    26640
gttccgaccc tgccgcttac cggatacctg tccgcctttc tcccttcggg aagcgtggcg    26700
ctttctcata gctcacgctg taggtatctc agttcggtgt aggtcgttcg ctccaagctg    26760
ggctgtgtgc acgaacccccc cgttcagccc gaccgctgcg ccttatccgg taactatcgt    26820
cttgagtcca acccggtaag acacgactta tcgccactgg cagcagccac tggtaacagg    26880
attagcagag cgaggtatgt aggcggtgct acagagttct tgaagtggtg gcctaactac    26940
```

```
ggctacacta aaggacagt atttggtatc tgcgctctgc tgaagccagt taccttcgga    27000
aaaagagttg gtagctcttg atccggcaaa caaaccaccg ctggtagcgg tggttttttt    27060
gtttgcaagc agcagattac gcgcagaaaa aaggatctc  aagaagatcc tttgatcttt    27120
tctacggggt ctgacgctca gtggaacgaa aactcacgtt aagggatttt ggtcatgaga    27180
ttatcaaaaa ggatcttcac ctagatcctt taaattaaa  aatgaagttt aaatcaatc     27240
taaagtatat atgagtaaac ttggtctgac agttaccaat gcttaatcag tgaggcacct    27300
atctcagcga tctgtctatt tcgttcatcc atagttgcct gactccccgt cgtgtagata    27360
actacgatac gggagggctt accatctggc cccagtgctg caatgatacc gcgagaccca    27420
cgctcaccgg ctccagattt atcagcaata aaccagccag ccggaagggc cgagcgcaga    27480
agtggtcctg caactttatc cgcctccatc cagtctatta attgttgccg ggaagctaga    27540
gtaagtagtt cgccagttaa tagtttgcgc aacgttgttg ccattgctgc aggggggggg    27600
ggggggggggt tccattgttc attccacgga caaaaacaga gaaggaaac  gacagaggcc    27660
aaaaagctcg ctttcagcac ctgtcgtttc ctttcttttc agagggtatt ttaaataaaa    27720
acattaagtt atgacgaaga agaacggaaa cgccttaaac cggaaaattt tcataaatag    27780
cgaaaacccg cgaggtcgcc gccccgtaac ctgtcggatc accggaaagg accgtaaag    27840
tgataatgat tatcatctac atatcacaac gtgcgtggag gccatcaaac cacgtcaaat    27900
aatcaattat gacgcaggta tcgtattaat tgatctgcat caactcaacg taaaaacaac    27960
ttcagacaat acaaatcagc gacactgaat acggggcaac ctcatgtccc ccccccccc    28020
cccctgcag  gcatcgcggt gtcacgctcg tcgtttggta tggcttcatt cagctccggt    28080
tcccaacgat caaggcgagt tacatgatcc cccatgttgt gcaaaaaagc ggttagctcc    28140
ttcggtcctc cgatcgttgt cagaagtaag ttggccgcag tgttatcact catggttatg    28200
gcagcactgc ataattctct tactgtcatg ccatccgtaa gatgcttttc tgtgactggt    28260
gagtactcaa ccaagtcatt ctgagaatag tgtatgcggc gaccgagttg ctcttgcccg    28320
gcgtcaacac gggataatac cgcgccacat agcagaactt taaaagtgct catcattgga    28380
aaacgttctt cggggcgaaa actctcaagg atcttaccgc tgttgagatc cagttcgatg    28440
taacccactc gtgcacccaa ctgatcttca gcatctttta ctttcaccag cgtttctggg    28500
tgagcaaaaa caggaaggca aaatgccgca aaaagggaa  taagggcgac acggaaatgt    28560
tgaatactca tactcttcct ttttcaatat tattgaagca tttatcaggg ttattgtctc    28620
gtgagcggat acatatttga atgtatttag aaaataaac  aataggggt  tccgcgcaca    28680
tttccccgaa aagtgccacc tgacgtctaa gaaaccatta ttatcatgac attaacctat    28740
aaaaataggc gtatcacgag gccctttcgt cttcaagaat tggtcgacga tcttgctgcg    28800
ttcggatatt ttcgtggagt tcccgccaca gacccggatt gaaggcgaga tccagcaact    28860
cgcgccagat catcctgtga cggaactttg gcgcgtgatg actggccagg acgtcggccg    28920
aaagagcgac aagcagatca cgcttttcga cagcgtcgga tttgcgatcg aggattttc     28980
ggcgctgcgc tacgtccgcg accgcgttga gggatcaagc cacagcagcc cactcgacct    29040
tctagccgac ccagacgagc caagggatct ttttggaatg ctgctccgtc gtcaggcttt    29100
ccgacgtttg ggtggttgaa cagaagtcat tatcgcacgg aatgccaagc actcccgagg    29160
ggaaccctgt ggttggcatg cacatacaaa tggacgaacg gataaacctt ttcacgccct    29220
tttaaatatc cgttattcta ataaacgctc ttttctctta ggtttacccg ccaatatatc    29280
```

```
ctgtcaaaca ctgatagttt aaactgaagg cgggaaacga caatctgatc atgagcctag    29340
ttagttaggg gcagctaacg tcccctagct aactagttgc tattaacctt tagcctagtt    29400
tagtgcggtc gcgctagtga actagtctaa tgggtgccta gcttagatta gatccccgtt    29460
cggcttagac taggttagtc ggatagggct agtctagtgg cttagcttgg aactgttaag    29520
ctaggctgtt agtgcgggac ttctaggcta acctattgac ccctaacgcc tagaacctaa    29580
gaaacgctaa ggacacctag ctaactttgg cgacgtccag aggtccgatt ccggctaact    29640
aactagctta agcttgatat cgaattcctg cagcccatcc ctcagccgcc tttcactatc    29700
ttttttgccc gagtcattgt catgtgaacc ttggcatgta taatcggtga attgcgtcga    29760
ttttcctctt ataggtgggc caatgaatcc gtgtgatcgc gtctgattgg ctagagatat    29820
gtttcttcct tgttggatgt attttcatac ataatcatat gcatacaaat atttcattac    29880
actttataga aatggtcagt aataaaccct atcactatgt ctggtgtttc attttatttg    29940
cttttaaacg aaaattgact tcctgattca atatttaagg atcgtcaacg gtgtgcagtt    30000
actaaattct ggtttgtagg aactatagta aactattcaa gtcttcactt attgtgcact    30060
cacctctcgc cacatcacca cagatgttat tcacgtctta aatttgaact acacatcata    30120
ttgacacaat attttttta aataagcgat taaaacctag cctctatgtc aacaatggtg    30180
tacataacca gcgaagttta gggagtaaaa acatcgcct tacacaaagt tcgctttaaa    30240
aaataaagag taaattttac tttgaccac ccttcaacca atgtttcact ttagaacgag    30300 taatttatt attgtcactt tggaccaccc tcaaatcttt tttccatcta catccaattt    30360
atcatgtcaa agaatggtc tacatacagc taaggagatt tatcgacgaa tagtagctag    30420
catactcgag gtcattcata tgcttgagaa gagagtcggg atagtccaaa ataaacaaa    30480 ggtaagatta cctggtcaaa agtgaaaaca tcagttaaaa ggtggtataa agtaaaatat    30540
cggtaataaa aggtggccca aagtgaaatt tactcttttc tactattata aaaattgagg    30600
atgtttttgt cggtactttg atacgtcatt tttgtatgaa ttggttttta agtttattcg    30660
cttttggaaa tgcatatctg tatttgagtc gggttttaag ttcgtttgct tttgtaaata    30720
cagagggatt tgtataagaa atatctttaa aaaaacccat atgctaattt gacataattt    30780
ttgaaaaaaa tatatattca ggcgaattct cacaatgaac aataataaga ttaaaatagc    30840
tttcccccgt tgcagcgcat gggtatttt tctagtaaaa ataaagata aacttagact    30900 caaaacattt acaaaaacaa cccctaaagt tcctaaagcc caaagtgcta tccacgatcc    30960
atagcaagcc cagcccaacc caacccaacc caacccaccc cagtccagcc aactggacaa    31020
tagtctccac accccccac tatcaccgtg agttgtccgc acgcaccgca cgtctcgcag    31080
ccaaaaaaaa aaaagaaaag aaaaaaaaga aaagaaaaa acagcaggtg ggtccgggtc    31140 gtggggccg gaaacgcgag gaggatcgcg agccagcgac gaggccggcc ctccctccgc    31200
ttccaaagaa acgccccca tcgccactat atacataccc cccctctcc tcccatcccc    31260 ccaaccctac caccaccacc accaccacct ccacctcctc cccctcgct gccggacgac    31320 gagctcctcc cccctccccc tccgccgccg ccgcgccggt aaccacccg cccctctcct    31380 ctttcttct ccgttttttt tttccgtcac ggtctcgatc tttggccttg gtagtttggg    31440
tgggcgagag gcggcttcgt gcgcgcccag atcggtgcgc gggagggcg ggatctcgcg    31500 gctgggctc tcgccggcgt ggatcaggcc cggatctcgc ggggaatggg gctctcggat    31560
gtagatctgc gatccgccgt tgttggggga gatgatgggg ggtttaaaat ttccgccatg    31620
ctaaacaaga tcaggaagag gggaaaaggg cactatggtt tatattttta tatttctg    31680
```

```
ctgcttcgtc aggcttagat gtgctagatc tttctttctt cttttttgtgg gtagaatttg   31740 aatccctcag cattgttcat cggtagtttt tcttttcatg atttgtgaca aatgcagcct   31800
cgtgcggagc ttttttgtag gtagaaggat ccatggcggc caatgcgggc ggcggtggag   31860
cgggaggagg cagcggcagc ggcagcgtgg ctgcgccggc ggtgtgccgc cccagcggct   31920
cgcggtggac gccgacgccg gagcagatca ggatgctgaa ggagctctac tacggctgcg   31980
gcatccggtc gcccagctcg gagcagatcc agcgcatcac cgccatgctg cggcagcacg   32040
gcaagatcga gggcaagaac gtcttctact ggttccagaa ccacaaggcc cgcgagcgcc   32100
agaagcgccg cctcaccagc ctcgacgtca acgtgcccgc cgccggcgcg ccgacgcca   32160 ccaccagcca actcggcgtc ctctcgctgt cgtcgccgcc gccttcaggc gcggcgcctc   32220
cctcgcccac cctcggcttc tacgccgccg gcaatggcgg cggatcggct gtgctgctgg   32280
acacgagttc cgactggggc agcagcggcg ctgctatggc caccgagaca tgcttcctgc   32340
aggactacat gggcgtgacg gacacgggca gctcgtcgca gtggccacgc ttctcgtcgt   32400
cggacacgat aatggcggcg gccgcggcgc gggcggcgac gacgcgggcg cccgagacgc   32460
tccctctctt cccgacctgc ggcgacgacg gcggcagcgg tagcagcagc tacttgccgt   32520
tctggggtgc cgcgtccaca actgccggcg ccacttcttc cgttgcgatc caacagcaac   32580
accagctgca ggagcagtac agcttttaca gcaacagcaa cagcacccag ctggccggca   32640
ccggcaacca agacgtatcg gcaacagcag cagcagccgc cgccctggag ctgagcctca   32700
gctcatggtg ctccccttac cctgctgcag ggagtatgtg aacctagact tgtccatctt   32760
ctggattggc caacttaatt aatgtatgaa ataaaaggat gcacacatag tgacatgcta   32820
atcactataa tgtgggcatc aaagttgtgt gttatgtgta attactagtt atctgaataa   32880
aagagaaaga gatcatccat atttcttatc ctaaatgaat gtcacgtgtc tttataattc   32940
tttgatgaac cagatgcatt tcattaacca aatccatata catataaata ttaatcatat   33000
ataattaata tcaattgggt tagcaaaaca aatctagtct aggtgtgttt tgcggcgatc   33060
gcggtaccat ttaaattgcg cccgccacgg ccgtggaggt cgtattccgg tcagcttgca   33120
tccctgcagt gcagcgtgac ccggtcgtgc ccctctctag agataatgag cattgcatgt   33180
ctaagttata aaaaattacc acatattttt tttgtcacac ttgtttgaag tgcagtttat   33240 ctatcttat acatatattt aaactttact ctacgaataa tataatctat agtactacaa   33300
taatatcagt gttttagaga atcatataaa tgaacagtta gacatggtct aaaggacaat   33360
tgagtatttt gacaacagga ctctacagtt ttatcttttt agtgtgcatg tgttctcctt   33420 ttttttttgca aatagcttca cctatataat acttcatcca ttttattagt acatccattt   33480
agggtttagg gttaatggtt tttatagact aatttttta gtacatctat tttattctat   33540
tttagcctct aaattaagaa aactaaaact ctattttagt tttttttttt aataatttag   33600
atataaaata gaataaaata aagtgactaa aaattaaaca aataccctt aagaaattaa   33660 aaaaactaag gaaacatttt tcttgtttcg agtagataat gccagcctgt taaacgccgt   33720
cgacgagtct aacggacacc aaccagcgaa ccagcagcgt cgcgtcgggc caagcgaagc   33780
agacggcacg gcatctctgt cgctgcctct ggacccctct cgagagttcc gctccaccgt   33840
tggacttgct ccgctgtcgg catccagaaa ttgcgtggcg gagcggcaga cgtgagccgg   33900
cacggcaggc ggcctcctcc tcctctcacg gcaccggcag ctacggggga ttccttccc   33960 accgctcctt cgctttccct tcctcgcccg ccgtaataaa tagacacccc ctccacaccc   34020
```

```
tctttcccca acctcgtgtt gttcggagcg cacacacaca caaccagatc tcccccaaat   34080
ccacccgtcg gcacctccgc ttcaaggtac gccgctcgtc ctccccoccc ccctctctca   34140 ccttctctag atcggcgttc cggtccatgc atggttaggg cccggtagtt ctacttctgt   34200
tcatgtttgt gttagatccg tgtttgtgtt agatccgtgc tgctagcgtt cgtacacgga   34260
tgcgacctgt acgtcagaca cgttctgatt gctaacttgc cagtgtttct ctttggggaa   34320
tcctgggatg gctctagccg ttccgcagac gggatcgatt tcatgatttt ttttgtttcg   34380
ttgcataggg tttggtttgc ccttttcctt tatttcaata tatgccgtgc acttgtttgt   34440
cgggtcatct tttcatgctt tttttgtct tggttgtgat gatgtggtct ggttgggcgg    34500
tcgttctaga tcggagtaga attctgtttc aaactacctg gtggatttat taattttgga   34560
tctgtatgtg tgtgccatac atattcatag ttacgaattg aagatgatgg atggaaatat   34620
cgatctagga taggtataca tgttgatgcg ggttttactg atgcatatac agagatgctt   34680
tttgttcgct tggttgtgat gatgtggtgt ggttgggcgg tcgttcattc gttctagatc   34740
ggagtagaat actgtttcaa actacctggt gtatttatta attttggaac tgtatgtgtg   34800
tgtcatacat cttcatagtt acgagtttaa gatggatgga aatatcgatc taggataggt   34860
atacatgttg atgtgggttt tactgatgca tatacatgat ggcatatgca gcatctattc   34920
atatgctcta accttgagta cctatctatt ataataaaca agtatgtttt ataattattt   34980
tgatcttgat atacttggat gatggcatat gcagcagcta tatgtggatt tttttagccc   35040
tgccttcata cgctatttat ttgcttggta ctgtttcttt tgtcgatgct caccctgttg   35100
tttggtgtta cttctgcagg tcgactctag aggatccatg ccactgtga acaactggct    35160 cgctttctcc ctctccccgc aggagctgcc gccctcccag acgacggact ccacactcat   35220
ctcggccgcc accgccgacc atgtctccgg cgatgtctgc ttcaacatcc cccaagattg   35280
gagcatgagg ggatcagagc tttcggcgct cgtcgcggag ccgaagctgg aggacttcct   35340
cggcggcatc tccttctccg agcagcatca caaggccaac tgcaacatga tacccagcac   35400
tagcagcaca gtttgctacg cgagctcagg tgctagcacc ggctaccatc accagctgta   35460
ccaccagccc accagctcag cgctccactt cgcggactcc gtaatggtgg cttcctcggc   35520
cggtgtccac gacggcggtg ccatgctcag cgcggccgcc gctaacggtg tcgctggcgc   35580
tgccagtgcc aacggcggcg gcatcgggct gtccatgatt aagaactggc tgcggagcca   35640
accggcgccc atgcagccga gggtggcggc ggctgagggc gcgcaggggc tctctttgtc   35700
catgaacatg gcggggacga cccaaggcgc tgctggcatg ccacttctcg ctggagagcg   35760
cgcacgggcg cccgagagtg tatcgacgtc agcacagggt ggagccgtcg tcgtcacggc   35820
gccgaaggag gatagcggtg gcagcggtgt tgccggcgct ctagtagccg tgagcacgga   35880
cacgggtggc agcggcggcg cgtcggctga caacacggca aggaagacgg tggacacgtt   35940
cgggcagcgc acgtcgattt accgtggcgt gacaaggcat agatggactg ggagatatga   36000
ggcacatctt tgggataaca gttgcagaag ggaagggcaa actcgtaagg gtcgtcaagt   36060
ctatttaggt ggctatgata aagaggagaa agctgctagg gcttatgatc ttgctgctct   36120
gaagtactgg ggtgccacaa caacaacaaa ttttccagtg agtaactacg aaaaggagct   36180
cgaggacatg aagcacatga caaggcagga gtttgtagcg tctctgagaa ggaagagcag   36240
tggtttctcc agaggtgcat ccatttacag gggagtgact aggcatcacc aacatggaag   36300
atggcaagca cggattggac gagttgcagg gaacaaggat cttttacttgg gcaccttcag   36360 cacccaggag gaggcagcgg aggcgtacga catcgcggcg atcaagttcc gcggcctcaa   36420
```

```
cgccgtcacc aacttcgaca tgagccgcta cgacgtgaag agcatcctgg acagcagcgc    36480
cctccccatc ggcagcgccg ccaagcgcct caaggaggcc gaggccgcag cgtccgcgca    36540
gcaccaccac gccggcgtgg tgagctacga cgtcggccgc atcgcctcgc agctcggcga    36600
cggcggagcc ctggcggcgg cgtacggcgc gcactaccac ggcgccgcct ggccgaccat    36660
cgcgttccag ccgggcgccg ccagcacagg cctgtaccac ccgtacgcgc agcagccaat    36720
gcgcggcggc gggtggtgca agcaggagca ggaccacgcg tgatcgcgg ccgcgcacag    36780 cctgcaggac ctccaccacc tgaacctggg cgcggccggc gcgcacgact ttttctcggc    36840
agggcagcag gccgccgccg ctgcgatgca cggcctgggt agcatcgaca gtgcgtcgct    36900
cgagcacagc accggctcca actccgtcgt ctacaacggc ggggtcggcg acagcaacgg    36960
cgccagcgcc gtcggcggca gtggcggtgg ctacatgatg ccgatgagcg ctgccggagc    37020
aaccactaca tcggcaatgg tgagccacga gcaggtgcat gcacgggcct acgacgaagc    37080
caagcaggct gctcagatgg ggtacgagag ctacctggtg aacgcggaga caatggtgg    37140 cggaaggatg tctgcatggg ggactgtcgt gtctgcagcc gcggcggcag cagcaagcag    37200
caacgacaac atgccgccg acgtcgggca tggcggcgcg cagctcttca gtgtctggaa    37260
cgacacttaa ggcgtacgtg ccggcctggc tctccgaaag ggcgtattcc agcacactgg    37320
cggccgttac tagacccaac ctagacttgt ccatcttctg gattggccaa cttaattaat    37380
gtatgaaata aaaggatgca cacatagtga catgctaatc actataatgt gggcatcaaa    37440
gttgtgtgtt atgtgtaatt actagttatc tgaataaaag agaaagagat catccatatt    37500
tcttatccta aatgaatgtc acgtgtcttt ataattcttt gatgaaccag atgcatttca    37560
ttaaccaaat ccatatacat ataaatatta atcatatata attaatatca attgggttag    37620 caaacaaat ctagtctagg tgtgttttgc gaatgcggcc tccggattct tatgtgcttc    37680
tagtctccaa atgtggttga tagttatttt gctctaagat caacagtaat gaagtataaa    37740
tcatcgttgt ggtgtgctac tcggttaatt gagcattaac acacacaaac atgacgagga    37800
tggtataatc tccaaaaatg tgtactttgt taggtgggac cctatagcct tgattaatgt    37860
gctatgttag gcatgcctgg aaacgtgtga cgcatatgtt ttgtgaacct gttgatatta    37920
tatgtgcttt tatattacca tattttatta aaatactaat atttattact agtaagatat    37980
aacattctat ctagcttaaa aactaaccat aaatattcca taataactag atttaccaaa    38040
ctaatatact aaatatacat aataaataca aaattaacaa gacaataatc aatatttatg    38100
agcttaatat atttagacat tatggttggt cgacgataat catgctaact tttcgtaatt    38160
gcttgattga aatatgctta gaataatgcc tctttgttct acatggcaaa tagggaccat    38220
tatggtgtaa caccctggga accacaaaca ccccgaaatg ctactaaact acacaactaa    38280
ccttcatata taaaatttcg acagcatctc ctttgaaaat ttgcatagac gtggaagcaa    38340
cagagtataa acagatatca tgataagaaa acatactaga cattaataat ctgctagaaa    38400
tgggaagaat cacgcgtaag cttgcatgcc tgcagtgcag cgtgacccgg tcgtgcccct    38460
ctctagagat aatgagcatt gcatgtctaa gttataaaaa attaccacat atttttttg    38520 tcacacttgt ttgaagtgca gtttatctat ctttatacat atatttaaac tttactctac    38580
gaataatata atctatagta ctacaataat atcagtgttt tagagaatca tataaatgaa    38640
cagttagaca tggtctaaag gacaattgag tattttgaca acaggactct acagttttat    38700 cttttagtg tgcatgtgtt ctccttttt tttgcaaata gcttcaccta tataatactt    38760
```

```
catccatttt attagtacat ccatttaggg tttagggtta atggttttta tagactaatt   38820
tttttagtac atctatttta ttctatttta gcctctaaat taagaaaact aaaactctat   38880
tttagttttt ttatttaata atttagatat aaaatagaat aaaataaagt gactaaaaat   38940
taaacaaata ccctttaaga aattaaaaaa actaaggaaa cattttttctt gtttcgagta   39000
gataatgcca gcctgttaaa cgccgtcgac gagtctaacg gacaccaacc agcgaaccag   39060
cagcgtcgcg tcgggccaag cgaagcagac ggcacggcat ctctgtcgct gcctctggac   39120
ccctctcgag agttccgctc caccgttgga cttgctccgc tgtcggcatc cagaaattgc   39180
gtggcggagc ggcagacgtg agccggcacg gcaggcggcc tcctcctcct ctcacggcac   39240
cggcagctac gggggattcc tttcccaccg ctccttcgct ttcccttcct cgcccgccgt   39300
aataaataga cacccctcc acaccctctt tccccaacct cgtgttgttc ggagcgcaca   39360
cacacacaac cagatctccc ccaaatccac ccgtcggcac ctccgcttca aggtacgccg   39420
ctcgtcctcc ccccccccc tctctacctt ctctagatcg gcgttccggt ccatgcatgg   39480
ttagggcccg gtagttctac ttctgttcat gtttgtgtta gatccgtgtt tgtgttagat   39540
ccgtgctgct agcgttcgta cacggatgcg acctgtacgt cagacacgtt ctgattgcta   39600
acttgccagt gtttctcttt ggggaatcct gggatggctc tagccgttcc gcagacggga   39660
tcgatttcat gatttttttt gtttcgttgc atagggtttg gtttgccctt ttcctttatt   39720
tcaatatatg ccgtgcactt gtttgtcggg tcatctttttc atgctttttt ttgtcttggt   39780
tgtgatgatg tggtctggtt gggcggtcgt tctagatcgg agtagaattc tgtttcaaac   39840
tacctggtgg atttattaat tttggatctg tatgtgtgtg ccatacatat tcatagttac   39900
gaattgaaga tgatggatgg aaatatcgat ctaggatagg tatacatgtt gatgcgggtt   39960
ttactgatgc atatacagag atgcttttg ttcgcttggt tgtgatgatg tggtgtggtt   40020
gggcggtcgt tcattcgttc tagatcggag tagaatactg tttcaaacta cctggtgtat   40080
ttattaattt tggaactgta tgtgtgtgtc atacatcttc atagttacga gtttaagatg   40140
gatggaaata tcgatctagg ataggtatac atgttgatgt gggttttact gatgcatata   40200
catgatggca tatgcagcat ctattcatat gctctaacct tgagtaccta tctattataa   40260
taaacaagta tgtttttataa ttattttgat cttgatatac ttggatgatg gcatatgcag   40320
cagctatatg tggatttttt tagccctgcc ttcatacgct atttatttgc ttggtactgt   40380
ttcttttgtc gatgctcacc ctgttgtttg gtgttacttc tgcaggtcga ctttaactta   40440
gcctaggatc caacaatgcc ccagttcgac atcctctgca agacccccc caaggtgctc   40500
gtgaggcagt tcgtggagag gttcgagagg ccctccggcg agaagatcgc cctctgcgcc   40560
gccgagctca cctacctctg ctggatgatc acccacaacg gcaccgccat taagagggcc   40620
accttcatgt catacaacac catcatctcc aactccctct ccttcgacat cgtgaacaag   40680
tccctccagt tcaaatacaa gacccagaag gccaccatcc tcgaggcctc cctcaagaag   40740
ctcatccccg cctgggagtt caccatcatc ccctactacg ccagaagca ccagtccgac   40800
atcaccgaca tcgtgtcatc cctccagctt cagttcgagt cctccgagga ggctgacaag   40860
ggcaactccc actccaagaa gatgctgaag gccctcctct ccgagggcga gtccatctgg   40920
gagatcaccg agaagatcct caactccttc gagtacacct ccaggttcac taagaccaag   40980
accctctacc agttcctctt cctcgccacc ttcatcaact gcggcaggtt ctcagacatc   41040
aagaacgtgg accccaagtc cttcaagctc gtgcagaaca agtacctagg tttgtttctg   41100
cttctacctt tgatatatat ataataatta tcattaatta gtagtaatat aatatttcaa   41160
```

```
atatttttt caaaataaaa gaatgtagta tatagcaatt gcttttctgt agtttataag   41220
tgtgtatatt ttaatttata acttttctaa tatatgacca aaacatggtg atgcctaggt   41280
gtcatcatcc agtgcctcgt gaccgagacc aagacctccg tgtccaggca catctacttc   41340
ttctccgctc gcggcaggat cgaccccctc gtgtacctcg acgagttcct caggaactca   41400
gagcccgtgc tcaagagggt gaacaggacc ggcaactcct cctccaacaa gcaggagtac   41460
cagctcctca aggacaacct cgtgaggtcc tacaacaagg ccctcaagaa gaacgccccc   41520
tactccatct tcgccatcaa gaacggcccc aagtcccaca tcggtaggca cctcatgacc   41580
tccttcctct caatgaaggg cctcaccgag ctcaccaacg tggtgggcaa ctggtccgac   41640
aagagggcct ccgccgtggc caggaccacc tacacccacc agatcaccgc catccccgac   41700
cactacttcg ccctcgtgtc aaggtactac gcctacgacc ccatctccaa ggagatgatc   41760
gccctcaagg acgagactaa ccccatcgag gagtggcagc acatcgagca gctcaagggc   41820
tccgccgagg gctccatcag gtaccccgcc tggaacggca tcatctccca ggaggtgctc   41880
gactacctct cctcctacat caacaggagg atctgagtta acctagactt gtccatcttc   41940
tggattggcc aacttaatta atgtatgaaa taaaaggatg cacacatagt gacatgctaa   42000
tcactataat gtgggcatca aagttgtgtg ttatgtgtaa ttactagtta tctgaataaa   42060
agagaaagag atcatccata tttcttatcc taaatgaatg tcacgtgtct ttataattct   42120
ttgatgaacc agatgcattt cattaaccaa atccatatac atataaatat taatcatata   42180
taattaatat caattgggtt agcaaaacaa atcagtcta ggtgtgtttt gcggtcacac   42240
cggttaaaac caaaatccag tggcgagctc tcgagtcgat cgctatcaac tttgtataga   42300
aaagttgggc cgaattcgag ctcggtacgg ccagaatggc ccggaccggg ttaccgaatt   42360
cgagctcggt accctgggat cagcttcgct gaaatcacca gtctctctct acaaatctat   42420
ctctctctat aataatgtgt gagtagttcc cagataaggg aattagggtt cttatagggt   42480
ttcgctcatg tgttgagcat ataagaaacc cttagtatgt atttgtattt gtaaaatact   42540
tctatcaata aaatttctaa ttcctaaaac caaaatccag tggcgagctg ctagcgaagt   42600
tcctattccg aagttcctat tctctagaaa gtataggaac ttcagatcca ccgggatccc   42660
cgatcatgca aaaactcatt aactcagtgc aaaactatgc ctgggcagc aaaacggcgt   42720
tgactgaact ttatggtatg gaaaatccgt ccagccagcc gatggccgag ctgtggatgg   42780
gcgcacatcc gaaaagcagt tcacgagtgc agaatgccgc cggagatatc gtttcactgc   42840
gtgatgtgat tgagagtgat aaatcgactc tgctcggaga ggccgttgcc aaacgctttg   42900
gcgaactgcc tttcctgttc aaagtattat gcgcagcaca gccactctcc attcaggttc   42960
atccaaacaa acacaattct gaaatcggtt ttgccaaaga aaatgccgca ggtatcccga   43020
tggatgccgc cgagcgtaac tataaagatc ctaaccacaa gccggagctg ttttttgcgc   43080
tgacgccttt ccttgcgatg aacgcgtttc gtgaattttc cgagattgtc tccctactcc   43140
agccggtcgc aggtgcacat ccggcgattg ctcactttt acaacagcct gatgccgaac   43200
gtttaagcga actgttcgcc agcctgtga atatgcaggg tgaagaaaaa tcccgcgcgc   43260
tggcgatttt aaaatcggcc ctcgatagcc agcagggtga accgtggcaa acgattcgtt   43320
taatttctga attttacccg gaagacagcg gtctgttctc cccgctattg ctgaatgtgg   43380
tgaaattgaa ccctggcgaa gcgatgttcc tgttcgctga acaccgcac gcttacctgc   43440
aaggcgtggc gctggaagtg atggcaaact ccgataacgt gctgcgtgcg ggtctgacgc   43500
```

```
ctaaatacat tgatattccg gaactggttg ccaatgtgaa attcgaagcc aaaccggcta    43560
accagttgtt gacccagccg gtgaaacaag gtgcagaact ggacttcccg attccagtgg    43620
atgattttgc cttctcgctg catgacctta gtgataaaga aaccaccatt agccagcaga    43680
gtgccgccat tttgttctgc gtcgaaggcg atgcaacgtt gtggaaaggt tctcagcagt    43740
tacagcttaa accgggtgaa tcagcgttta ttgccgccaa cgaatcaccg gtgactgtca    43800
aaggccacgg ccgtttagcg cgtgtttaca acaagctgta agagcttact gaaaaaatta    43860
acatctcttg ctaagctggg ggtggaacct agacttgtcc atcttctgga ttggccaact    43920
taattaatgt atgaaataaa aggatgcaca catagtgaca tgctaatcac tataatgtgg    43980
gcatcaaagt tgtgtgttat gtgtaattac tagttatctg aataaaagag aaagagatca    44040
tccatatttc ttatcctaaa tgaatgtcac gtgtctttat aattctttga tgaaccagat    44100
gcatttcatt aaccaaatcc atatacatat aaatattaat catatataat taatatcaat    44160
tgggttagca aaacaaatct agtctaggtg tgttttgcga atgcgacctt cttatgtgct    44220
tctagtctcc aaatgtggtt gatagttatt ttgctctaag atcaacagta atgaagtata    44280
aatcatcgtt gtggtgtgct actcggttaa ttgagcatta acacacacaa acatgacgag    44340
gatggtataa tctccaaaaa tgtgtacttt gttaggtggg accctatagc cttgattaat    44400
gtgctatgtt aggcatgcct ggaaacgtgt gacgcatatg ttttgtgaac ctgttgatat    44460
tatatgtgct tttatattac catattttat taaaatacta atatttatta ctagtaagat    44520
ataacattct atctagctta aaaactaacc ataaatattc cataataact agatttacca    44580
aactaatata ctaaatatac ataataaata caaaattaac aagacaataa tcaatattta    44640
tgagcttaat atatttagac attatggttg gtcgacgata atcatgctaa cttttcgtaa    44700
ttgcttgatt gaaatatgct tagaataatg cctctttgtt ctacatggca aatagggacc    44760
attatggtgt aacaccctgg gaaccacaaa caccccgaaa tgctactaaa ctacacaact    44820
aaccttcata tataaaattt cgacagcatc tcctttgaaa atttgcatag acgtggaagc    44880
aacagagtat aaacagatat catgataaga aaacatacta gacattaata atctgctaga    44940
aatgggaaga atcctaactt gacgactgcg taactgacta gagtcacact tagctgaccc    45000
tagtcactta caactgactt cgtgtcctag gcttaggcta ctgctagtcc gcggtgtatc    45060
cgtgatcgag ttggcgccag acggaatctg ttctccatcg ctgacatcct cgagtagatc    45120
acattcaagc ttgatatcga attcctgcag cccatccctc agccgccttt cactatcttt    45180
tttgcccgag tcattgtcat gtgaaccttg gcatgtataa tcggtgaatt gcgtcgattt    45240
tcctcttata ggtgggccaa tgaatccgtg tgatcgcgtc tgattggcta gagatatgtt    45300
tcttccttgt tggatgtatt ttcatacata atcatatgca tacaaatatt tcattacact    45360
ttatagaaat ggtcagtaat aaaccctatc actatgtctg gtgtttcatt ttatttgctt    45420
ttaaacgaaa attgacttcc tgattcaata tttaaggatc gtcaacggtg tgcagttact    45480
aaattctggt ttgtaggaac tatagtaaac tattcaagtc ttcacttatt gtgcactcac    45540
ctctcgccac atcaccacag atgttattca cgtcttaaat ttgaactaca catcatattg    45600
acacaatatt ttttttaaat aagcgattaa aacctagcct ctatgtcaac aatggtgtac    45660
ataaccagcg aagtttaggg agtaaaaaac atcgccttac acaagttcg ctttaaaaaa    45720 taaagagtaa atttttacttt ggaccaccct tcaaccaatg tttcactta gaacgagtaa    45780 ttttattatt gtcactttgg accaccctca aatctttttt ccatctacat ccaatttatc    45840
atgtcaaaga aatggtctac atacagctaa ggagatttat cgacgaatag tagctagcat    45900
```

```
actcgaggtc attcatatgc ttgagaagag agtcgggata gtccaaaata aaacaaaggt    45960
aagattacct ggtcaaaagt gaaaacatca gttaaaggt ggtataaagt aaaatatcgg     46020
taataaaagg tggcccaaag tgaaatttac tcttttctac tattataaaa attgaggatg    46080
tttttgtcgg tactttgata cgtcattttt gtatgaattg gttttaagt ttattcgctt     46140 ttggaaatgc atatctgtat ttgagtcggg ttttaagttc gtttgctttt gtaaatacag    46200
agggatttgt ataagaaata tctttaaaaa aacccatatg ctaatttgac ataatttttg    46260
agaaaaatat atattcaggc gaattctcac aatgaacaat aataagatta aaatagcttt    46320
cccccgttgc agcgcatggg tattttttct agtaaaaata aaagataaac ttagactcaa    46380
aacatttaca aaaacaaccc ctaaagttcc taaagcccaa agtgctatcc acgatccata    46440
gcaagcccag cccaacccaa cccaacccaa cccaccccag tccagccaac tggacaaatag   46500 tctccacacc cccccactat caccgtgagt tgtccgcacg caccgcacgt ctcgcagcca    46560
aaaaaaaaaa aagaaagaaa aaaagaaaa agaaaaaaca gcaggtgggt ccgggtcgtg     46620
ggggccggaa acgcgaggag gatcgcgagc cagcgacgag gccggccctc cctccgcttc    46680
caaagaaacg ccccccatcg ccactatata catacccccc cctctcctcc catccccca     46740 accctaccac caccaccacc accacctcca cctcctcccc cctcgctgcc ggacgacgag    46800
ctcctccccc ctcccctcc gccgccgccg cgccggtaac caccccgccc ctctcctctt     46860
tctttctccg tttttttttt ccgtcacggt ctcgatcttt ggccttggta gtttgggtgg    46920
gcgagaggcg gcttcgtgcg cgcccagatc ggtgcgcggg aggggcggga tctcgcggct    46980
ggggctctcg ccggcgtgga tcaggcccgg atctcgcggg gaatgggct ctcggatgta     47040 gatctgcgat ccgccgttgt tgggggagat gatggggggt ttaaaatttc cgccatgcta    47100
aacaagatca ggaagagggg aaaagggcac tatggtttat attttatat atttctgctg     47160 cttcgtcagg cttagatgtg ctagatcttt ctttcttctt tttgtgggta gaatttgaat    47220
ccctcagcat tgttcatcgg tagttttct tttcatgatt tgtgacaaat gcagcctcgt     47280
gcggagcttt tttgtaggta gaaggatcca cacgacacca tgtcccccga gcgccgcccc    47340
gtcgagatcc gccggccac cgccgccgac atggccgccg tgtgcgacat cgtgaaccac    47400
tacatcgaga cctccaccgt gaacttccgc accgagccgc agaccccgca ggagtggatc    47460
gacgacctgg agcgcctcca ggaccgctac ccgtggctcg tggccgaggt ggagggcgtg    47520
gtggccggca tcgcctacgc cggcccgtgg aaggcccgca acgcctacga ctggaccgtg    47580
gagtccaccg tgtacgtgtc ccaccgccac cagcgcctcg gcctcggctc caccctctac    47640
acccacctcc tcaagagcat ggaggcccag ggcttcaagt ccgtggtggc cgtgatcggc    47700
ctcccgaacg acccgtccgt gcgcctccac gaggccctcg gctacaccgc ccgcggcacc    47760
ctgcgcgccg ccggctacaa gcacggcggc tggcacgacg tcggcttctg gcagcgcgac    47820
ttcgagctgc cggccccgcc gcgccggtg cgccggtga cgcagatctg agtcgacctg      47880
caggcatgcc gctgaaatca ccagtctctc tctacaaatc tatctctctc tataataatg    47940
tgtgagtagt tcccagataa gggaattagg gttcttatag ggtttcgctc atgtgttgag    48000
catataagaa acccttagta tgtatttgta tttgtaaaat acttctatca ataaatttc     48060 taattcctaa aaccaaaatc cagtggcgag ctaatgcggc ccgaataact tcgtatagca    48120
tacattatac gaagttatac ctggtggcgc cgctaggggc tgcaggaatt cctgcagccc    48180
gggggatcca ctagttctag agcggccgac ctcgacagat ctaagcttac tagtgccgtg    48240
```

| | | | | | |
|---|---|---|---|---|---|
| ggtcgtttaa | gctgccgctg | tacctgtgtc | gtctggtgcc | ttctggtgta | cctgggaggt | 48300 |
| tgtcgtctat | caagtatctg | tggttggtgt | catgagtcag | tgagtcccaa | tactgttcgt | 48360 |
| gtcctgtgtg | cattataccc | aaaactgtta | tgggcaaatc | atgaataagc | ttgatgttcg | 48420 |
| aacttaaaag | tctctgctca | atatggtatt | atggttgttt | ttgttcgtct | cctaatattt | 48480 |
| gcctgggatc | aaattttatt | ggctggtgtt | catttgacct | ccatgttctt | gctaggctcc | 48540 |
| attttttact | ctacagccat | aatatgtttg | attgttggt | ttgttctttg | ttgtacacct | 48600 |
| ggttctgtcg | agcttagttt | tcgacactgg | cttacagctt | aacatgttgc | tattttattg | 48660 |
| ggttctgatt | gctattttat | tgggttctga | ttgctagttt | ttgctgaatc | caaaaaccat | 48720 |
| gttatttatt | taagcgatcc | aggttattat | tatgatggtg | gctaagtttt | tttttttcca | 48780 |
| agggtaaatt | ttctggattc | tccagtgttt | ctgtggccga | attcactagt | gattcagatc | 48840 |
| tgatatcgat | gggcccacta | actatctata | ctgtaataat | gttgtatagc | cgccggatag | 48900 |
| ctagctagtt | tagtcattca | gcggcgatgg | gtaataataa | agtgtcatcc | atccatcacc | 48960 |
| atgggtggca | acgtgagcaa | tgacctgatt | gaacaaattg | aaatgaaaag | aagaaatatg | 49020 |
| ttatatgtca | acgagatttc | ctcataatgc | cactgacgac | gtgtgtccaa | gaaatgtatc | 49080 |
| agtgatacgt | atattcacaa | ttttttatg | acttatactc | acaatttgtt | tttttactac | 49140 |
| ttatactcac | aatttgttgt | gggtaccata | acaatttcga | tcgaatatat | atcagaaagt | 49200 |
| tgacgaaagt | aagctcactc | aaaaagttaa | atgggctgcg | gaagctgcgt | caggcccaag | 49260 |
| ttttggctat | tctatccggt | atccacgatt | ttgatggctg | agggacatat | gttcgcttaa | 49320 |
| gcttggtcac | ccggtccggg | cctagaaggc | cagcttcaag | tttgtacaaa | aaagcaggct | 49380 |
| ccggccagaa | tctcactgac | tagctaaaca | gcggccgctt | ttaagtatga | ccaattttta | 49440 |
| agtataaacc | cctcacgatt | ggttattttt | ttaagtataa | ccaattttta | agtataaacc | 49500 |
| cctcaccaat | ttttaagtat | aaacctagcg | actaataaac | acaacttctt | gccaaagtgt | 49560 |
| gagcatcacc | attggatctg | cgcccctcac | gaacagtctt | cgccggggta | aaattctcca | 49620 |
| aattaaagtc | atcttgatgt | ccttgatcac | ctgtccataa | ggcccaatcc | cagctccacg | 49680 |
| tatacttctg | ataagattga | catagtcact | tgcatgccag | tgtggaactc | tggatgccta | 49740 |
| ggtcagaggc | tagtgactgg | ccttcccggc | atgctagcat | gtagcatgcc | aaggatctgg | 49800 |
| ctgctccagg | tttgttatgc | ctgacatcac | cataggatg | agagcaagta | taataatagg | 49860 |
| ctgtaagctt | taaatgctca | ggtggagaaa | aaaggagag | gagaggagag | agaaaagtgg | 49920 |
| gctataagct | tatagctgtg | ttagacataa | gaatcagaaa | cttcgtatga | gagacaggtg | 49980 |
| agctatatat | taataacaaa | gagctaacta | ttatatgagt | gaaccgagag | aaggctgtaa | 50040 |
| aaaaacttac | acaatcaacg | atcgacatta | ttattaacct | tgctctgtct | tgcgagacct | 50100 |
| ctttgacaaa | gctacatcaa | tgccggccaa | gtgccttggg | atttgggaat | ggcttctttc | 50160 |
| ctcccttcct | cggttgtccc | ccaaggccta | ggcttgccac | gctgtattca | gtcgcagccg | 50220 |
| cctttacttt | tgccctttgt | ggaagttttg | taataaatgg | tctgattcta | tcttcggata | 50280 |
| gatgaagccg | gatgtttcat | ccattatcta | aaaaaagtt | ggttgctttg | ctgagctaag | 50340 |
| aaagtgtaat | ccagagtgcc | cgtaacgtat | tcatgtacat | aactattatc | taatataaat | 50400 |
| cttcttttgt | cgcaaaaaaa | ggtcggccca | tcagaacaaa | tgatcaatgt | aaggcccaaa | 50460 |
| atttgtgtct | caaatgtcat | ttacgtttcc | aagctaaaca | aaaacacagg | attcatataa | 50520 |
| ttttgctggt | ggcttaggct | tcgtccaata | gtgcttagtt | taatttgtat | atacctgcac | 50580 |
| catggtattc | gtctggcctt | ggatcttgcg | catcaattgc | ctatggacga | tgatcgcagc | 50640 |

```
cacgccacat tcatttttaa tcgccatttg cttgacaccc aatgcctctg caccacttgc    50700
gcacgctacg caccgtctga tacgccaaga tcccgagcta aaataacacc caatcatcag    50760
atgaaaacaa gcgcgagtgc gagccagccc atggcagcga tcttggccat ttgcggagcc    50820
aactgaaagc cgtgcacaaa atattcgaca ccgtataagg gaaaacacta gttatacgag    50880
gtgggcaata atccagatct cggactcttc ctaacccggt tcacatgcat agcatatatg    50940
atggccggcc ggggttcaca tgaacgccat cccgtgccct agtgcactga tttcttaatt    51000
tcgaatttta agtatgacca attttttaagt ataaacccct cacgattggt tatttttta    51060 agtataacca attttttaagt ataaacccct caccaatttt taagtataaa cctagcgact    51120
aataaacaca acttcttgcc aaagtgtgag catcaccatt ggatctgcgc ccctcacgaa    51180
cagtcttcgc cggggtaaaa ttctccaaat taaagtcatc ttgatgtcct tgatcacctg    51240
tccataaggc ccaatcccag ctccacgtat acttctgata agattgacat agtcacttgc    51300
atgccagtgt ggaactctgg atgcctaggt cagaggctag tgactggcct tcccggcatg    51360
ctagcatgta gcatgccaag gatctggctg ctccaggttt gttatgcctg acatcaccat    51420
agggatgaga gcaagtataa taataggctg taagctttaa atgctcaggt ggagaaaaaa    51480
aggagaggag aggagagaga aaagtgggct ataagcttat agctgtgtta gacataagaa    51540
tcagaaactt cgtatgagag acaggtgagc tatatattaa taacaaagag ctaactatta    51600
tatgagtgaa ccgagagaag gctgtaaaaa aacttacaca atcaacgatc gacattatta    51660
ttaaccttgc tctgtcttgc gagacctctt tgacaaagct acatcaatgc cggccaagtg    51720
ccttgggatt tgggaatggc ttctttcctc ccttcctcgg ttgtccccca aggcctaggc    51780
ttgccacgct gtattcagtc gcagccgcct ttacttttgc cctttgtgga agttttgtaa    51840
taaatggtct gattctatct tcggatagat gaagccggat gtttcatcca ttatctaaaa    51900
aaaagttggt tgctttgctg agctaagaaa gtgtaatcca gagtgcccgt aacgtattca    51960
tgtacataac tattatctaa tataaatctt cttttgtcgc aaaaaaaggt cggcccatca    52020
gaacaaatga tcaatgtaag gcccaaaatt tgtgtctcaa atgtcattta cgtttccaag    52080
ctaaacaaaa acacaggatt catataattt tgctggtggc ttaggcttcg tccaatagtg    52140
cttagtttaa tttgtatata cctgcaccat ggtattcgtc tggccttgga tcttgcgcat    52200
caattgccta tggacgatga tcgcagccac gccacattca tttttaatcg ccatttgctt    52260
gacacccaat gcctctgcac cacttgcgca cgctacgcac cgtctgatac gccaagatcc    52320
cgagctaaaa taacacccaa tcatcagatg aaaacaagcg cgagtgcgag ccagcccatg    52380
gcagcgatct tggccatttg cggagccaac tgaaagccgt gcacaaaata ttcgacaccg    52440 tataaggaa aacactagtt atacgaggtg gcaataatc cagatctcgg actcttccta    52500
acccggttca catgcatagc atatatgatg gccggccggg gttcacatga acgccatccc    52560
gtgccctagt gcactgattt cttaatgtcg acggccgct tttaagtatg accaattttt    52620
aagtataaac ccctcacgat tggttatttt tttaagtata accaattttt aagtataaac    52680
ccctcaccaa ttttttaagta taaacctagc gactaataaa cacaacttct tgccaaagtg    52740
tgagcatcac cattggatct gcgcccctca cgaacagtct tcgccggggt aaaattctcc    52800
aaattaaagt catcttgatg tccttgatca cctgtccata aggcccaatc ccagctccac    52860
gtatacttct gataagattg acatagtcac ttgcatgcca gtgtggaact ctggatgcct    52920
aggtcagagg ctagtgactg gccttcccgg catgctagca tgtagcatgc caaggatctg    52980
```

```
gctgctccag gtttgttatg cctgacatca ccatagggat gagagcaagt ataataatag   53040
gctgtaagct ttaaatgctc aggtggagaa aaaaaggaga ggagaggaga gagaaaagtg   53100
ggctataagc ttatagctgt gttagacata agaatcagaa acttcgtatg agagacaggt   53160
gagctatata ttaataacaa agagctaact attatatgag tgaaccgaga gaaggctgta   53220
aaaaaactta cacaatcaac gatcgacatt attattaacc ttgctctgtc ttgcgagacc   53280
tctttgacaa agctacatca atgccggcca agtgccttgg gatttgggaa tggcttcttt   53340
cctcccttcc tcggttgtcc cccaaggcct aggcttgcca cgctgtattc agtcgcagcc   53400
gcctttactt ttgcccttg tggaagtttt gtaataaatg gtctgattct atcttcggat   53460
agatgaagcc ggatgtttca tccattatct aaaaaaaagt tggttgcttt gctgagctaa   53520
gaaagtgtaa tccagagtgt tcgtaacgta ttcatgtaca taactattat ctaatataaa   53580
tcttcttttg tcgcaaaaaa aggtcggccc atcagaacaa atgatcaatg taaggcccaa   53640
aatttgtgtc tcaaatgtca tttacgtttc caagctaaac aaaaacacag gattcatata   53700
attttgctgg tggcttaggc ttcgtccaat agtgcttagt ttaatttgta tatacctgca   53760
ccatggtatt cgtctggcct tggatcttgc gcatcaattg cctatggacg atgatcgcag   53820
ccacgccaca ttcattttta atcgccattt gcttgacacc caatgcctct gcaccacttg   53880
cgcacgctac gcaccgtctg atacgccaag atcccgagct aaaataacac ccaatcatca   53940
gatgaaaaca agcgcgagtg cgagccagcc catggcagcg atcttggcca tttgcggagc   54000
caactgaaag ccgtgcacaa aatattcgac accgtataag ggaaaacact agttatacga   54060
ggtgggcaat aatccagatc tcggactctt cctaacccgg ttcacatgca tagcatatat   54120
gatggccggc cggggttcac atgaacgcca tcccgtgccc tagtgcactg atttcttaat   54180
cccatccagc atgctcttca attttggtgc tcacccttac gggtatgccc tcactgcctt   54240
ttataattgt ataagggaaa tattattcaa tataatgtcc taaaaattgg caatatcaat   54300
ctaaaaatcg ttatgaatag gatgtaaaca aagctactat ctgtccatat ataacgtcac   54360
aggaaggaca aaaaattcag tcagcgatcg agaacggcaa agaaaaacca tattattgtt   54420
gcttgccgac ataaatttaa gtataggaca aaaaaaaaag ccacatcata ttacatacta   54480
tgggcttacc agacaaaatg aaataaacgt gtgcatgcat gcatgcatgg tacgaacgtc   54540
tggatagagt ctccgagctg agtgtggtcc gacgtggaag tgtacgtctc aacacacgac   54600
gcatgtgacc gacaagggca agttgaagtc tatgcatgga tgggcctgag cgccgcgctg   54660
aatgaatctg gacgggtggt agggcatctc ggtgggcaaa acaaataact ccgtgtgctg   54720
catggctgcc tttggaatct ttgcatgcag ctgtgtgctg aactgaaacc cttcgctcta   54780
tctatataaa cagatgccct tcgctctcgt ctcagcaggc agcatcgtct caagttttgt   54840
tctcctctcc tagctagcca gcacctgcag atctgctcgt tgccttggta attcatcatg   54900
tagtacgtag catcagctag tatttatctc aagtatatat atacgcatat gtgtcgtcgc   54960
agtactttcc cttatctctc tatacacact acacgcatac ataccaatac catccgtctt   55020
aactcttaat ctttgcctgc atacgtacac tgcacgtacg tactgcaggg ctactgattt   55080
tgtggaacga agcggtcgag accggtgatc ttgtaaggtt cccttccctc ctcccctcac   55140 accctgttc gtgttccttc ggatcggatc tcagtggtga tgttagacgt ccgcggctgc   55200
ctacgtagtg gcattccgc ccgaaaggtt tgtttaggtg gggtagatcc gaaacaggcc   55260
ggatctggac catgtccgcg gcggggcggc gggacttgat cgcgtagctg tcgtgtgcat   55320
ttctccctac cagtggcgga atcggcgatg tggacctaag ggctaaggct tatctgctgc   55380
```

```
cttgaccatt tcgtcgctga caaaaacaaa gtgacaatca tgccgttctc tgtttgttta    55440
tctggatcgt tattacgctg tgaatcctgc gatatgtggc taagtgattt ttcttcttt     55500 tctgggggca gtttagcctt tgacccagtc ctaggtgtgg tcactaggac tgtgtagcat    55560
gatgagtgag gttgcagcag gctgattgct agtggacgtt ttttccccca atttgttagg    55620
ttttcacgct ccaggttgtg caagtaattt tgctagtgat tgtgtgatcc atcttcaacg    55680
ttgaaccttg ttttccccc  taaaaccccc aacaggaaat cttgcccga  cttctattgc    55740 aaaaattgta acgcttagca ccctgattga ctcaattcct gtcactaggc atgctcggtc    55800
aaaagcagat gatttaccac ttagaaactg ccctgcccct gctttccaca tagcatttcg    55860 aacttttga  ctactattga cacccccta  acttgccgaa ctatttctct cttcagctac    55920
tatttaccta gttataatta cataaatgtt tgtgtgtatc ttgtgcaggg atccgccatg    55980
gcagagccga caagggtgg  agcacctgcg atgaagaacg tcgccaagcc gtcgaccaaa    56040
cgcctgatcc cgagctcgat agccgcttcg agccagacta cgccaacgc  tctgacggag    56100 ccccttcctg ggtctgacgc gatcggccag agctacgacg cattcgggtt cttcgccaat    56160
ccccgcagca tcatgaagga gctgttcgag ttcagcccac aggaggagat cgtcgtcgaa    56220
ggcaacacct ggcttctcag cagcgacttc gtctacaccg ccatccgcga cacagagacc    56280
tcgaccgtct cgaggcgcac caaggacgac tacagcaagg agctggccgt gaaggtgaag    56340
ctcagcggaa gctacggcta cttcagcgct agcgtggaga gcgacttcag ccagagcatc    56400
agcgacgcta ccgacacgac gtacaccagc gtccgcaccc acgtcaacaa gtggcgcctc    56460
agcctcaagg acgacgtcgg agctctccgg agcaagctcc ttcctggtgt caagcaggct    56520
ctcgctacga tggacgcaac ccagctcttc gacacgttcg gcacccacta cgtcagcgag    56580
gtcctcgtcg gtggaagagc cgactacgtc gccaccacca agaccagcgc cttcagctcg    56640
agcacctcca tcagcgtcgc tgcagaggcg tcgtttcaga gcatcgcagg aggcgaagtc    56700
agccccgaga gcaaggtcct cgccgagatg ctgcgcgaga actccagcac acggctctac    56760
gcactgggag gctcagcact cccgaacatc acggacccag cgacctacaa cgcctggctg    56820
gagagcatcg acaccatccc ggtcttctgc ggcttcaccc agaactccct caagtcgatc    56880
agcgagctcg cggattcagc ccaacgcaga gacgcactcg cgaaggcatc ccagtcgtac    56940
atccccagct acgtcactcg cccagcagtc gtgggcctcg aggtcatcat ctccgactcc    57000
aactccgaga gccctccata cggctacacc cggatcgact acgacctcaa ccgcaatgcc    57060
ggaggcaagt acgtcttcct ctgctacaag cagaagaaca tctccgtcgg aggtgacgca    57120
gacgcgatca cggacgtcct cgtcgtctac ggcaacgacc ggaacccaag cgtgccctca    57180
ggctacacca agatcgacaa ggacctgaac tccggagctg gagggaagta catctacttc    57240
tgctactcca aggacaagcg caagcaggag gagggccttc cgatacgcgg acttcgcgtc    57300 gttgaccac  accctacgtc agtggcaccg tacggcttca gcaagatcga catcgacctc    57360
aacatgggcg caggtgggga cttcatctac ctctgcaagt cgcggcacct cgagtgagtt    57420
aaccccgggt caacccatca ggaaggatga agcgccctc  attttgtgcc ctaggtcgtg    57480
gattgctgga ttttaatttt acacatttcc ttgtcgatcc tttctgctgt gtgtggttcg    57540
agaatgttag tgtgttatcg caagatctgg gtgtttggaa gttatctcat tattgggcct    57600
cataaattca taattcttgc cagttagtga caactgtagc ttaggtttac ttctgcttgt    57660
agtacatcgc ctagatcgtg ggagtccctc ttttcagacg aatgtcatga aacattggtt    57720
```

```
tttggaaatg attaggaaga catttgctgt tttgtcgact gctgttttt   acggccaagt    57780
tcagagtttt ttttttcatg tacaaagtat cagcagttaa attatgttac ctttaccatg    57840
gttcttcata tttgttttcc ttccattgct caatctatgt catcttttga aatggtttgg    57900
aaggcatcct ttataggata tatagatata gatttgaagc ataattgtta ggataagaca    57960
ccagctagcc tatgctgcaa cgcacattat tcgaccctta ataacaacag gtgatttta    58020
tattataaaa aagttggaaa agtatacaca agaattttc aaaagaaggg taaaagggaa     58080
cagccctcct gctcgacaat tggaattggt gtcccgcata atttttttct gcctttgaga    58140
attcaggcgt ctctggattc tagttcacca tttaccaatt agaaggaata ctatgtatgt    58200
ataattctac aatctgcatt ctacacaatc cttctatttt ctgaatatag ttgcaagact    58260
agggctctct tatagtattt ctaattatag ccgctttgca aagtactgtc atatttgatt    58320
aggggtattg gaagaagga gaaaagggtg acaccctgct tgacaattgg aattgataag     58380
cagccaggggt accaaggcgc gaaacagccc cctccggcgg tgtccccac tgaagaaact    58440
atgtgctgta gtatagccgc tggctagcta gctagttgag tcatttagcg gcgatgattg    58500
agtaataatg tgtcacgcat caccatgcat gggtggcagt ctcagtgtga gcaatgacct    58560
gaatgaacaa ttgaaatgaa aagaaaaaag tattgttcca aattaaacgt tttaaccttt    58620
taataggttt atacaataat tgatatatgt tttctgtata tgtctaattt gttatcatcc    58680
atttagatat agacgaaaaa aaatctaaga actaaaacaa atgctaattt gaatgaagg     58740
gagtatatat tgggataatg tcgatgagat ccctcgtaat atcaccgaca tcacacgtgt    58800
ccagttaatg tatcagtgat acgtgtattc acatttgttg cgcgtaggcg tacccaacaa    58860
ttttgatcga ctatcagaaa gtcaacggaa gcgctgcaga aacttatctc tgttatgaat    58920
cagaagaagt tcatgtctcg tttcatttaa aactttggtg gtttgtgttt tggggccttg    58980
taaagcccct gatgaataat tgttcaacta tgtttccgtt cctgtgttat accttcttt    59040
ctaatgagta atgacatcaa acttcttctg tattgaaatt atgtccttgt gagtctcttt    59100
atcatcgttt cgtctttaca ttatatgtgc tactttgtc taatgagcct gaaaagtggc    59160
tccaatggta cgcactggaa gatttgttgg cttctggtag atatagcgac agtgttgagc    59220
ttgtaatatc atgtctctta ttgctaaatt agttcctttc ttaacagaaa ccttcaaagt    59280
ttttgttttt gttttcattt acctaatgta cacatacgct ggccatgact aacaacatg     59340
ccaggcttag agcatatttt tttctagctt aaattgttaa cttgtcattc agtaaaatcc    59400
gagaattgtg aagctctaat tgaagctaat tcgttttata aagtcagtta aaagtatac     59460
taaattatcc aacttttctt caaaatctca aaattctatg acaaaacgat agtctttgtt    59520
tatgtcagta ccacaaagag gtggaaaaaa acaccaaaaa aacaataagc aaactataca    59580
ctgagaagaa aaataaaaga gagctcaata gatgtttat actaacggta gattagatca     59640
aagatccaag ctttactcta catagagcag aacccagaat cccttcatat ctcttttatt    59700
ctagcaccga taatctactg aaaagaagac acttagagct ctgtctcttt gtcaaagaag    59760
tcccagccgt catccagaag ctccttacgt tcattaacag agaattcgac aaagcagcat    59820
tagtccgttg atcggtggaa gaccactcgt cagtgttgag ttgaatgttt gatcaataaa    59880
atacggcaat gctgtaaggg ttgttttta tgccattgat aatacactgt actgttcagt     59940
tgttgaactc tatttcttag ccatgccaag tgcttttctt attttgaata acattacagc    60000
aaaaagttga aagacaaaaa aaaaaacccc cgaacagagt gctttgggtc ccaagcttct    60060
ttagactgtg ttcggcgttc cccctaaatt tctccccta tatctcactc acttgtcaca     60120
```

```
tcagcgttct ctttccccct atatctccac gctctacagc agttccacct atatcaaacc   60180
tctatacccc accacaacaa tattatatac tttcatcttc aactaactca tgtaccttcc   60240 aattttttc tactaataat tatttacgtg cacagaaact tagcaaggag agagagagcg    60300
gggtgaccaa gcttggcgcg ccattctatc actagctagc tgctaattat tcccgggcac   60360
ccagctttct tgtacaaagt ggccgttaca gaatcactga ctagctaatc tagcggccgc   60420
tcaagcttcg gcatgcaatt cgcataccta cagtacaacg tggccaaagt catcatttaa   60480
tgagctctcg ggcgcgccgt ctcactagct agctgctaac gttcccgggc aactttatta   60540
tacaaagttg atagatccta caggccagaa tggcctctgg attcagcggc tagaaggcc    60600 gaagtacttg gtcttcctaa tatcggaccg aggaccgatt aaactttaat tcggtccgtc   60660
aatattcacc gaagcgacta attaactagc tgtcccacgg cctaactagc acttaatccc   60720
ctagcctaac ctaagagcgc taatctaggc tagtggtcac ttagggcttt aaggctagcg   60780
tatacgaagt tcctattccg aagttcctat tcttcaaaaa gtataggaac ttctgtacac   60840
ctgagcctaa ctaactagga cgtcccgagg tccgattccg ggctaattaa cacctagctc   60900
gccactcgac taattaggga ctaagcctag cgcttagccg ttaaaaccta gcacacccta   60960
agcaccctta gttaggttcc cctcttaatt aagccctagt gagcccctaa gttaagggga   61020
cgctaagagc cccctaacct agtattcggc tagaggcgaa ctaggctaaa cacctaagcg   61080
cacctcttta agctagatcg ctaggggct aggctagagc ttcgctagat tagtctaagg    61140
gcagctaact aactagggc gcgccaatac cgaattcatt ccgattaatc gtggcctctt    61200
gctcttcagg atgaagagct atgtttaaac gtgcaagcgc tactagacaa ttcagtacat   61260
taaaaacgtc cgcaatgtgt tattaagttg tctaagcgtc aatttgttta caccacaata   61320
tatcctgcca ccagccagcc aacagctccc cgaccggcag ctcggcacaa aatcaccact   61380
cgatacaggc agcccatcag tccgggacgg cgtcagcggg agagccgttg taaggcggca   61440
gactttgctc atgttaccga tgctattcgg aagaacggca actaagctgc cgggtttgaa   61500
acacggatga tctcgcggag ggtagcatgt tgattgtaac gatgacagag cgttgctgcc   61560
tgtgatcaaa tatcatctcc ctcgcagaga tccgaattat cagccttctt attcatttct   61620
cgcttaaccg tgacaggctg tcgatcttga gaactatgcc gacataatag gaaatcgctg   61680
gataaagccg ctgaggaagc tgagtggcgc tatttcttta gaagtgaacg ttgacgatcg   61740
tcgaccgtac cccgatgaat taattcggac gtacgttctg aacacagctg gatacttact   61800
tgggcgattg tcatacatga catcaacaat gtacccgttt gtgtaaccgt ctcttggagg   61860
ttcgtatgac actagtggtt cccctcagct tgcgactaga tgttgaggcc taacatttta   61920
ttagagagca ggctagttgc ttagatacat gatcttcagg ccgttatctg tcagggcaag   61980
cgaaaattgg ccatttatga cgaccaatgc cccgcagaag ctcccatctt tgccgccata   62040
gacgccgcgc ccccctttttg gggtgtagaa catccttttg ccagatgtgg aaagaagtt    62100 cgttgtccca ttgttggcaa tgacgtagta gccggcgaaa gtgcgagacc catttgcgct   62160
atatataagc ctacgatttc cgttgcgact attgtcgtaa ttggatgaac tattatcgta   62220
gttgctctca gagttgtcgt aatttgatgg actattgtcg taattgctta tggagttgtc   62280
gtagttgctt ggagaaatgt cgtagttgga tggggagtag tcatagggaa gacgagcttc   62340
atccactaaa acaattggca ggtcagcaag tgcctgcccc gatgcatcg caagtacgag     62400 gcttagaacc accttcaaca gatcgcgcat agtcttcccc agctctctaa cgcttgagtt   62460
```

-continued

```
aagccgcgcc gcgaagcggc gtcggcttga acgaattgtt agacattatt tgccgactac  62520
cttggtgatc tcgcctttca cgtagtgaac aaattcttcc aactgatctg cgcgcgaggc  62580
caagcgatct tcttgtccaa gataagcctg cctagcttca agtatgacgg gctgatactg  62640
ggccggcagg cgctccattg cccagtcggc agcgacatcc ttcggcgcga ttttgccggt  62700
tactgcgctg taccaaatgc gggacaacgt aagcactaca tttcgctcat cgccagccca  62760
gtcgggcggc gagttccata gcgttaaggt ttcatttagc gcctcaaata gatcctgttc  62820
aggaaccgga tcaaagagtt cctccgccgc tggacctacc aaggcaacgc tatgttctct  62880
tgcttttgtc agcaagatag ccagatcaat gtcgatcgtg gctggctcga agatacctgc  62940
aagaatgtca ttgcgctgcc attctccaaa ttgcagttcg cgcttagctg gataacgcca  63000
cggaatgatg tcgtcgtgca caacaatggt gacttctaca gcgcggagaa tctcgctctc  63060
tccaggggaa gccgaagttt ccaaaaggtc gttgatcaaa gctcgccgcg ttgtttcatc  63120
aagccttaca gtcaccgtaa ccagcaaatc aatatcactg tgtggcttca ggccgccatc  63180
cactgcggag ccgtacaaat gtacggccag caacgtcggt tcgagatggc gctcgatgac  63240
gccaactacc tctgatagtt gagtcgatac ttcgcgatc accgcttccc tcatgatgtt  63300
taactcctga attaagccgc gccgcgaagc ggtgtcggct tgaatgaatt gttaggcgtc  63360
atcctgtgct cccgagaacc agtaccagta catcgctgtt tcgttcgaga cttgaggtct  63420
agttttatac gtgaacaggt caatgccgcc gagagtaaag ccacattttg cgtacaaatt  63480
gcaggcaggt acattgttcg tttgtgtctc taatcgtatg ccaaggagct gtctgcttag  63540
tgcccacttt ttcgcaaatt cgatgagact gtgcgcgact cctttgcctc ggtgcgtgtg  63600
cgacacaaca atgtgttcga tagaggctag atcgttccat gttgagttga gttcaatctt  63660
cccgacaagc tcttggtcga tgaatgcgcc atagcaagca gagtcttcat cagagtcatc  63720
atccgagatg taatccttcc ggtaggggct cacacttctg gtagatagtt caaagccttg  63780
gtcggatagg tgcacatcga acacttcacg aacaatgaaa tggttctcag catccaatgt  63840
ttccgccacc tgctcaggga tcaccgaaat cttcatatga cgcctaacgc ctggcacagc  63900
ggatcgcaaa cctggcgcgg cttttggcac aaaaggcgtg acaggtttgc gaatccgttg  63960
ctgccacttg ttaacccttt tgccagattt ggtaactata atttatgtta gaggcgaagt  64020
cttgggtaaa aactggccta aaattgctgg ggatttcagg aaagtaaaca tcaccttccg  64080
gctcgatgtc tattgtagat atatgtagtg tatctacttg atcggggat ctgctgcctc  64140 gcgcgtttcg gtgatgacgg tgaaaacctc tgacacatgc agctcccgga gacggtcaca  64200
gcttgtctgt aagcggatgc cgggagcaga caagcccgtc agggcgcgtc agcgggtgtt  64260
ggcgggtgtc ggggcgcagc catgacccag tcacgtagcg atagcggagt gtatactggc  64320
ttaactatgc ggcatcagag cagattgtac tgagagtgca ccatatgcgg tgtgaaatac  64380
cgcacagatg cgtaaggaga aaataccgca tcaggcgctc ttccgcttcc tcgctcactg  64440
actcgctgcg ctcggtcgtt cggctgcggc gagcggtatc agctcactca aaggcggtaa  64500
tacggttatc cacagaatca ggggataacg caggaaagaa catgtgagca aaaggccagc  64560
aaaaggccag gaaccgtaaa aaggccgcgt tgctggcgtt tttccatagg ctccgccccc  64620
ctgacgagca tcacaaaaat cgacgctcaa gtcagaggtg gcgaaacccg acaggactat  64680
aaagatacca ggcgtttccc cctggaagct ccctcgtgcg ctctcctgtt ccgaccctgc  64740
cgcttaccgg atacctgtcc gcctttctcc cttcgggaag cgtggcgctt tctcatagct  64800
cacgctgtag gtatctcagt tcggtgtagg tcgttcgctc caagctgggc tgtgtgcacg  64860
```

```
aaccccccgt tcagcccgac cgctgcgcct tatccggtaa ctatcgtctt gagtccaacc   64920
cggtaagaca cgacttatcg ccactggcag cagccactgg taacaggatt agcagagcga   64980
ggtatgtagg cggtgctaca gagttcttga agtggtggcc taactacggc tacactagaa   65040
ggacagtatt tggtatctgc gctctgctga agccagttac cttcggaaaa agagttggta   65100
gctcttgatc cggcaaacaa accaccgctg gtagcggtgg ttttttttgtt tgcaagcagc   65160 agattacgcg cagaaaaaaa ggatctcaag aagatccttt gatcttttct acggggtctg   65220
acgctcagtg gaacgaaaac tcacgttaag ggattttggt catgagatta tcaaaaagga   65280
tcttcaccta gatccttta aattaaaaat gaagttttaa atcaatctaa agtatatatg   65340
agtaaacttg gtctgacagt taccaatgct taatcagtga ggcacctatc tcagcgatct   65400
gtctatttcg ttcatccata gttgcctgac tccccgtcgt gtagataact acgatacggg   65460
agggcttacc atctggcccc agtgctgcaa tgataccgcg agacccacgc tcaccggctc   65520
cagatttatc agcaataaac cagccagccg gaagggccga gcgcagaagt ggtcctgcaa   65580
ctttatccgc ctccatccag tctattaatt gttgccggga agctagagta agtagttcgc   65640
cagttaatag tttgcgcaac gttgttgcca ttgctgcagg ggggggggg ggggggttc   65700 cattgttcat tccacggaca aaaacagaga aaggaaacga cagaggccaa aaagctcgct   65760 ttcagcaccct gtcgtttcct ttcttttcag agggtatttt aaataaaaac attaagttat   65820
gacgaagaag aacggaaacg ccttaaaccg gaaaattttc ataaatagcg aaaacccgcg   65880
aggtcgccgc cccgtaacct gtcggatcac cggaaaggac ccgtaaagtg ataatgatta   65940
tcatctacat atcacaacgt gcgtggaggc catcaaacca cgtcaaataa tcaattatga   66000
cgcaggtatc gtattaattg atctgcatca acttaacgta aaaacaactt cagacaatac   66060
aaatcagcga cactgaatac ggggcaacct catgtccccc ccccccccc ccctgcaggc   66120 atcgtggtgt cacgctcgtc gtttggtatg gcttcattca gctccggttc caacgatca   66180 aggcgagtta catgatcccc catgttgtgc aaaaaagcgg ttagctcctt cggtcctccg   66240
atcgttgtca gaagtaagtt ggccgcagtg ttatcactca tggttatggc agcactgcat   66300
aattctctta ctgtcatgcc atccgtaaga tgcttttctg tgactggtga gtactcaacc   66360
aagtcattct gagaatagtg tatgcggcga ccgagttgct cttgcccggc gtcaacacgg   66420
gataataccg cgccacatag cagaacttta aaagtgctca tcattggaaa acgttcttcg   66480
gggcgaaaac tctcaaggat cttaccgctg ttgagatcca gttcgatgta acccactcgt   66540
gcacccaact gatcttcagc atcttttact ttcaccagcg tttctgggtg agcaaaaaca   66600
ggaaggcaaa atgccgcaaa aaagggaata agggcgacac ggaaatgttg aatactcata   66660
ctcttccttt ttcaatatta ttgaagcatt tatcagggtt attgtctcat gagcggatac   66720
atatttgaat gtatttagaa aaataaacaa ataggggttc cgcgcacatt tccccgaaaa   66780
gtgccacctg acgtctaaga aaccattatt atcatgacat taacctataa aaataggcgt   66840
atcacgaggc cctttcgtct tcaagaattc ggagcttttg ccattctcac cggattcagt   66900
cgtcactcat ggtgatttct cacttgataa ccttatttt gacgagggga aattaatagg   66960
ttgtattgat gttggacgag tcggaatcgc agaccgatac caggatcttg ccatcctatg   67020
gaactgcctc ggtgagtttt ctccttcatt acagaaacgg cttttttcaaa aatatggtat   67080 tgataatcct gatatgaata aattgcagtt tcatttgatg ctcgatgagt ttttctaatc   67140
agaattggtt aattggttgt aacactggca gagcattacg ctgacttgac gggacggcgg   67200
```

```
ctttgttgaa taaatcgaac ttttgctgag ttgaaggatc agatcacgca tcttcccgac    67260
aacgcagacc gttccgtggc aaagcaaaag ttcaaaatca ccaactggtc cacctacaac    67320
aaagctctca tcaaccgtgg ctccctcact ttctggctgg atgatggggc gattcaggcc    67380
tggtatgagt cagcaacacc ttcttcacga ggcagacctc agcgccagaa ggccgccaga    67440
gaggccgagc gcggccgtga ggcttggacg ctagggcagg gcatgaaaaa gcccgtagcg    67500
ggctgctacg ggcgtctgac gcggtggaaa ggggagggg atgttgtcta catggctctg    67560
ctgtagtgag tgggttgcgc tccggcagcg gtcctgatca atcgtcaccc tttctcggtc    67620
cttcaacgtt cctgacaacg agcctccttt tcgccaatcc atcgacaatc accgcgagtc    67680
cctgctcgaa cgctgcgtcc ggaccggctt cgtcgaaggc gtctatcgcg gcccgcaaca    67740
gcggcgagag cggagcctgt tcaacggtgc cgccgcgctc gccggcatcg ctgtcgccgg    67800
cctgctcctc aagcacggcc ccaacagtga agtagctgat tgtcatcagc gcattgacgg    67860 cgtcccggc cgaaaaaccc gcctcgcaga ggaagcgaag ctgcgcgtcg gccgtttcca    67920
tctgcggtgc gcccggtcgc gtgccggcat ggatgcgcgc gccatcgcgg taggcgagca    67980
gcgcctgcct gaagctgcgg gcattcccga tcagaaatga gcgccagtcg tcgtcggctc    68040
tcggcaccga atgcgtatga ttctccgcca gcatggcttc ggccagtgcg tcgagcagcg    68100
cccgcttgtt cctgaagtgc cagtaaagcg ccggctgctg aacccccaac cgttccgcca    68160
gtttgcgtgt cgtcagaccg tctacgccga cctcgttcaa caggtccagg gcggcacgga    68220
tcactgtatt cggctgcaac tttgtcatgc ttgacacttt atcactgata aacataatat    68280
gtccaccaac ttatcagtga taaagaatcc gcgcgttcaa tcggaccagc ggaggctggt    68340
ccggaggcca gacgtgaaac ccaacatacc cctgatcgta attctgagca ctgtcgcgct    68400
cgacgctgtc ggcatcggcc tgattatgcc ggtgctgccg gcctcctgc gcgatctggt    68460 tcactcgaac gacgtcaccg cccactatgg cattctgctg gcgctgtatg cgttggtgca    68520
atttgcctgc gcacctgtgc tgggcgcgct gtcggatcgt ttcggcggc ggccaatctt    68580 gctcgtctcg ctggccggcg ccactgtcga ctacgccatc atggcgacag cgcctttcct    68640
ttgggttctc tatatcgggc ggatcgtggc cggcatcacc ggggcgactg gggcggtagc    68700
cggcgcttat attgccgata tcactgatgg cgatgagcgc gcgcggcact tcggcttcat    68760
gagcgcctgt ttcggttcg ggatggtcgc gggacctgtg ctcggtgggc tgatgggcgg    68820
tttctccccc cacgctccgt tcttcgccgc ggcagccttg aacggcctca atttcctgac    68880
gggctgtttc cttttgccgg agtcgcacaa aggcgaacgc cggccgttac gccgggaggc    68940
tctcaacccg ctcgcttcgt tccggtgggc ccggggcatg accgtcgtcg ccgccctgat    69000
ggcggtcttc ttcatcatgc aacttgtcgg acaggtgccg gccgcgcttt gggtcatttt    69060
cggcgaggat cgctttcact gggacgcgac cacgatcggc atttcgcttg ccgcatttgg    69120
cattctgcat tcactcgccc aggcaatgat caccggccct gtagccgccc ggctcggcga    69180
aaggcgggca ctcatgctcg gaatgattgc cgacggcaca ggctacatcc tgcttgcctt    69240
cgcgacacgg ggatggatgg cgttcccgat catggtcctg cttgcttcgg gtggcatcgg    69300
aatgccggcc ctgcaagcaa tgttgtccag gcaggtggat gaggaacgtc aggggcagct    69360
gcaaggctca ctggcggcgc tcaccagcct gacctcgatc gtcggacccc tcctcttcac    69420
ggcgatctat gcggcttcta taacaacgtg gaacgggtgg gcatggattg caggcgctgc    69480
cctctacttg ctctgcctgc cggcgctgcg tcgcgggctt tggagcggcg cagggcaacg    69540
agccgatcgc tgatcgtgga aacgataggc ctatgccatg cgggtcaagg cgacttccgg    69600
```

```
caagctatac gcgccctagg agtgcggttg aacgttggc ccagccagat actcccgatc    69660
acgagcagga cgccgatgat ttgaagcgca ctcagcgtct gatccaagaa caaccatcct    69720
agcaacacgg cggtccccgg gctgagaaag cccagtaagg aaacaactgt aggttcgagt    69780
cgcgagatcc cccggaacca aaggaagtag gttaaacccg ctccgatcag gccgagccac    69840
gccaggccga gaacattggt tcctgtaggc atcgggattg gcggatcaaa cactaaagct    69900
actgaaacga gcagaagtcc tccggccgcc agttgccagg cggtaaaggt gagcagaggc    69960
acgggaggtt gccacttgcg ggtcagcacg gttccgaacg ccatggaaac cgcccccgcc    70020
aggcccgctg cgacgccgac aggatctagc gctgcgtttg gtgtcaacac caacagcgcc    70080
acgcccgcag ttccgcaaat agccccccagg accgccatca atcgtatcgg gctacctagc    70140
agagcggcag agatgaacac gaccatcagc ggctgcacag cgcctaccgt cgccgcgacc    70200
ccgcccggca ggcggtagac cgaaataaac aacaagctcc agaatagcga aatattaagt    70260
gcgccgagga tgaagatgcg catccaccag attcccgttg gaatctgtcg gacgatcatc    70320
acgagcaata acccgccgg caacgcccgc agcagcatac cggcgacccc tcggcctcgc    70380
tgttcgggct ccacgaaaac gccggacaga tgcgccttgt gagcgtcctt ggggccgtcc    70440
tcctgtttga agaccgacag cccaatgatc tcgccgtcga tgtaggcgcc gaatgccacg    70500
gcatctcgca accgttcagc gaacgcctcc atgggctttt tctcctcgtg ctcgtaaacg    70560
gacccgaaca tctctggagc tttcttcagg gccgacaatc ggatctcgcg gaaatcctgc    70620
acgtcggccg ctccaagccg tcgaatctga gccttaatca caattgtcaa ttttaatcct    70680
ctgtttatcg gcagttcgta gagcgcgccg tgcgtcccga gcgatactga gcgaagcaag    70740
tgcgtcgagc agtgcccgct tgttcctgaa atgccagtaa agcgctggct gctgaacccc    70800
cagccggaac tgaccccaca aggccctagc gtttgcaatg caccaggtca tcattgaccc    70860
aggcgtgttc caccaggccg ctgcctcgca actcttcgca ggcttcgccg acctgctcgc    70920
gccacttctt cacgcgggtg gaatccgatc cgcacatgag gcggaaggtt tccagcttga    70980
gcgggtacgg ctcccggtgc gagctgaaat agtcgaacat ccgtcgggcc gtcggcgaca    71040
gcttgcggta cttctcccat atgaatttcg tgtagtggtc gccagcaaac agcacgacga    71100
tttcctcgtc gatcaggacc tggcaacggg acgttttctt gccacggtcc aggacgcgga    71160
agcggtgcag cagcgacacc gattccaggt gcccaacgcg gtcggacgtg aagcccatcg    71220
ccgtcgcctg taggcgcgac aggcattcct cggccttcgt gtaataccgg ccattgatcg    71280
accagcccag gtcctggcaa agctcgtaga acgtgaaggt gatcggctcg ccgatagggg    71340
tgcgcttcgc gtactccaac acctgctgcc acaccagttc gtcatcgtcg gcccgcagct    71400
cgacgccggt gtaggtgatc ttcacgtcct tgttgacgtg gaaaatgacc ttgttttgca    71460
gcgcctcgcg cgggattttc ttgttgcgcg tggtgaacag ggcagagcgg gccgtgtcgt    71520
ttggcatcgc tcgcatcgtg tccggccacg gcgcaatatc gaacaaggaa agctgcattt    71580
ccttgatctg ctgcttcgtg tgtttcagca acgcggcctg cttggcctcg ctgacctgtt    71640
ttgccaggtc ctcgccggcg ttttttcgct tcttggtcgt catagttcct cgcgtgtcga    71700
tggtcatcga cttcgccaaa cctgccgcct cctgttcgag acgacgcgaa cgctccacgg    71760
cggccgatgg cgcgggcagg gcaggggag ccagttgcac gctgtcgcgc tcgatcttgg    71820
ccgtagcttg ctgaccatc gagccgacgg actggaaggt ttcgcggggc gcacgcatga    71880
cggtgcggct tgcgatggtt tcggcatcct cggcggaaaa ccccgcgtcg atcagttctt    71940
```

```
gcctgtatgc cttccggtca aacgtccgat tcattcaccc tccttgcggg attgccccga   72000
ctcacgccgg ggcaatgtgc ccttattcct gatttgaccc gcctggtgcc ttggtgtcca   72060
gataatccac cttatcggca atgaagtcgg tcccgtagac cgtctggccg tccttctcgt   72120
acttggtatt ccgaatcttg ccctgcacga ataccagcga cccttgccc aaatacttgc    72180 cgtgggcctc ggcctgagag ccaaaacact tgatgcggaa gaagtcggtg cgctcctgct   72240
tgtcgccggc atcgttgcgc cactcttcat taaccgctat atcgaaaatt gcttgcggct   72300
tgttagaatt gccatgacgt acctcggtgt cacgggtaag attaccgata aactggaact   72360
gattatggct catatcgaaa gtctccttga gaaggagac tctagtttag ctaaacattg    72420
gttccgctgt caagaacttt agcggctaaa attttgcggg ccgcgaccaa aggtgcgagg   72480
ggcggcttcc gctgtgtaca accagatatt tttcaccaac atccttcgtc tgctcgatga   72540
gcggggcatg acgaaacatg agctgtcgga gagggcaggg gtttcaattt cgttttatc    72600 agacttaacc aacggtaagg ccaacccctc gttgaaggtg atggaggcca ttgccgacgc   72660
cctggaaact cccctacctc ttctcctgga gtccaccgac cttgaccgcg aggcactcgc   72720
ggagattgcg ggtcatcctt tcaagagcag cgtgccgccc ggatacgaac gcatcagtgt   72780
ggttttgccg tcacataagg cgtttatcgt aaagaaatgg ggcgacgaca cccgaaaaaa   72840
gctgcgtgga aggctctgac gccaagggtt agggcttgca cttccttctt tagccgctaa   72900
aacggcccct tctctgcggg ccgtcggctc gcgcatcata tcgacatcct caacggaagc   72960
cgtgccgcga atggcatcgg gcgggtgcgc tttgacagtt gttttctatc agaaccccta   73020
cgtcgtgcgg ttcgattagc tgtttgtctt gcaggctaaa cactttcggt atatcgtttg   73080
cctgtgcgat aatgttgcta atgatttgtt gcgtaggggt tactgaaaag tgagcgggaa   73140
agaagagttt cagaccatca aggagcgggc caagcgcaag ctggaacgcg acatgggtgc   73200
ggacctgttg gccgcgctca acgacccgaa aaccgttgaa gtcatgctca acgcggacgg   73260
caaggtgtgg cacgaacgcc ttggcgagcc gatgcggtac atctgcgaca tgcggcccag   73320
ccagtcgcag gcgattatag aaacggtggc cggattccac ggcaaagagg tcacgcggca   73380
ttcgcccatc ctggaaggcg agttcccctt ggatggcagc cgctttgccg gccaattgcc   73440
gccggtcgtg gccgcgccaa cctttgcgat ccgcaagcgc gcggtcgcca tcttcacgct   73500
ggaacagtac gtcgaggcgg gcatcatgac ccgcgagcaa tacgaggtca ttaaaagcgc   73560
cgtcgcggcg catcgaaaca tcctcgtcat tggcggtact ggctcgggca agaccacgct   73620
cgtcaacgcg atcatcaatg aaatggtcgc cttcaacccg tctgagcgcg tcgtcatcat   73680
cgaggacacc ggcgaaatcc agtgcgccgc agagaacgcc gtccaatacc acaccagcat   73740
cgacgtctcg atgacgctgc tgctcaagac aacgctgcgt atgcgccccg accgcatcct   73800
ggtcggtgag gtacgtggcc ccgaagccct tgatctgttg atggcctgga acaccgggca   73860
tgaaggaggt gccgccaccc tgcacgcaaa caaccccaaa gcgggcctga ccggctcgc    73920 catgcttatc agcatgcacc cggattcacc gaaacccatt gagccgctga ttggcgaggc   73980
ggttcatgtg gtcgtccata tcgccaggac ccctagcggc cgtcgagtgc aagaaattct   74040
cgaagttctt ggttacgaga acggccagta catcaccaaa accctgtaag gagtatttcc   74100
aatgacaacg gctgttccgt tccgtctgac catgaatcgc ggcattttgt tctaccttgc   74160
cgtgttcttc gttctcgctc tcgcgttatc cgcgcatccg gcgatggcct cggaaggcac   74220
cggcggcagc ttgccatatg agagctggct gacgaacctg cgcaactccg taaccggccc   74280
ggtggccttc gcgctgtcca tcatcggcat cgtcgtcgcc ggcggcgtgc tgatcttcgg   74340
```

```
cggcgaactc aacgccttct tccgaaccct gatcttcctg gttctggtga tggcgctgct    74400
ggtcggcgcg cagaacgtga tgagcacctt cttcggtcgt ggtgccgaaa tcgcggccct    74460
cggcaacggg gcgctgcacc aggtgcaagt cgcggcggcg gatgccgtgc gtgcggtagc    74520
ggctggacgg ctcgcctaat catggctctg cgcacgatcc ccatccgtcg cgcaggcaac    74580
cgagaaaacc tgttcatggg tggtgatcgt gaactggtga tgttctcggg cctgatggcg    74640
tttgcgctga ttttcagcgc ccaagagctg cgggccaccg tggtcggtct gatcctgtgg    74700
ttcggggcgc tctatgcgtt ccgaatcatg gcgaaggccg atccgaagat gcggttcgtg    74760
tacctgcgtc accgccggta caagccgtat tacccggccc gctcgacccc gttccgcgag    74820
aacaccaata gccaagggaa gcaataccga tgatccaagc aattgcgatt gcaatcgcgg    74880
gcctcggcgc gcttctgttg ttcatcctct ttgcccgcat ccgcgcggtc gatgccgaac    74940
tgaaactgaa aaagcatcgt tccaaggacg ccggcctggc cgatctgctc aactacg       74997

<210> SEQ ID NO 2
<211> LENGTH: 24867
<212> TYPE: DNA
<213> ORGANISM: Artificial Sequence
<220> FEATURE:
<223> OTHER INFORMATION: Synthetic

<400> SEQUENCE: 2
cgtactgcac tgccaccatt caagacaagc tatggtcgtc gccgtgaacg tgagccgcgc      60
atcgttgaag gctaggtcca cgaggaggta gacaagggca catgcgctcc caagagcttg     120
ttcgtgttcg tgacccgacg accgcgcgcg tttgtccgtg ggctcgtggg acgccagcag     180
cccacgcgaa acggttcccc tgccgcgcgc gcgcgcgccc ggtgcatggc tctcctcagc     240
ctccgaatgg agtcatcacc gtcgacgcct cgacggcgcg gaggtgacca aataaggtcc     300
ggctgctcgc agccgtggca cgaaacgagg acacacggac tggtaggagg ctaggggggg     360
cacggacaag accgctccgt tccgttgcct ctcccgcgct ctgcgaggga tgatgcatgg     420
gcagcgcgcg gacacacgga ctggcagcgg ccctgtaccc acgtcgcagt gccgggatcc     480
gcgcctacca cggcacgatc agcgtcatca tggcacaatc attcacgaac ctcccagtcc     540
cagcggattg cacgccgaaa aatcgtcctc tagaagaaag cttttctcg tcgcacatcg      600 gcgcttctgc tcggcacggc atgtgaaact gtcagggcac aggggtaggt ttactgacaa     660
ggtttgattt cttttccggc tgctgagcac ggtccgcgac tgggagcaaa ttcaatgccc     720
ttgctttctc ccgtcccggc ccattcaaac cgggccgtcg ttttagtttc tttttatgtt     780
ttacttggtt ttagcggcga ggcgatgcaa cgaagaccac agcagcaaac tactattgtt     840
tcagggtcat ttctaataca ctctccgtcc taaaatatta ggtggcgctt ggcagagttt     900
ccacagcttc gctcagagcg agaatcactc ttactgagct aaatgataaa aatcggaact     960
gcttcatgtt gagagtggag tgaatctagt ctacactatg tattagaaag tgagagaaaa    1020
aaaacatgct tcccactaca ctactcccaa catgctcccc actctttaac ccctcatgaa    1080
tcatttcaca gcctatttgc caaacaattt tcgtcaaata tattcacttc tagtagagaa    1140
tcactcagaa tcaccaatca gctctcggaa ctagagaatt gatcaaagac aaactctatt    1200
accttcaatg atatgtggtt atgattcatg ttggcaagct gtgatcctgt tgctgctgtt    1260
cccctggtac tttttttttt gtgtgccggt tgagttttta tagtttatgt tgtgctgcat    1320
atgaatgagt tttggtagtt accgtggttg ccgttcacag cggcgttgcc tgctgttcat    1380
```

```
atgttggcaa tccgtgaatt tgcatgcttc tatatatgag tttggtgttc aattgtactt      1440
atatactacc aaaaaatacc atagtttcag tgggctgaag aaattaaaac ccatgcatgc      1500
tagtaatgtc atagctaggt gtataccatg gttttccaat accaaactta gctaccaaac      1560
acatactact gcatctgtat atataatgca ctggtgtgca gccgtcagcc gtgtgccttc      1620
tgaagcgtga aacctggtaa aaaaaaaaaa cgggggaggc aagaagcatc agggcaggca      1680
ggaggatcct agtacatatc ctacttactg gcttgcagca aggctagctg atggctgcgt      1740
gcgtgcttac atgatgatga tcatgcgtgt cgttcgtact cgtacgagga tcgaggaaag      1800
acaccataac tcaccttcaa cagacaccct tcgttaggag catgcacgga tagatggcgt      1860
ctagcatatc gataggacat gacaagtggt acgatccccg tcacatgtcc atggaggcat      1920
ctgatatgga cacggcgtgt atctatcgcg gctggaacag aaccagcgct cgcgcggcgg      1980
tcggcgggag ggacagacct tggctccgtg cgttcaggtt gtgcttgtgc cgcgcgccac      2040
gcacggtctc cgccgcctgc agctgaaatt ttagatttac atcctatccc tttattttt      2100 ttatttgtca caattcagtt caaaaatgaa gaacggaggt agtgcatcct tgtgagact      2160 aatgaaaatc acatctggat cctgaaatcg gcgtcgtaac ctacaaggcc acggactgga      2220
ttagatagtg gtccatggtg cataatgagg atcgaggggc acctcactga ctagctaatc      2280
gagctagtta ccctatgagg tgacatgaag cgctcacggt tactatgacg gttagcttca      2340
cgactgttgg tggcagtagc gtacgactta gctatagttc cggacttacc gataacttcg      2400
tatagcatac attatacgaa gttatggcgc cgctagcctg cagtgcagcg tgacccggtc      2460
gtgcccctct ctagagataa tgagcattgc atgtctaagt tataaaaaat taccacatat      2520
tttttttgtc acacttgttt gaagtgcagt ttatctatct ttatacatat atttaaactt      2580
tactctacga ataatataat ctatagtact acaataatat cagtgtttta gagaatcata      2640
taaatgaaca gttagacatg gtctaaagga caattgagta ttttgacaac aggactctac      2700
agttttatct ttttagtgtg catgtgttct ccttttttt tgcaaatagc ttcacctata      2760
taatacttca tccattttat tagtacatcc atttagggtt tagggttaat ggttttata      2820 gactaatttt tttagtacat ctattttatt ctattttagc ctctaaatta agaaaactaa      2880
aactctattt tagttttttt atttaataat ttagatataa aatagaataa cataaagtga      2940
ctaaaaatta aacaaatacc ctttaagaaa ttaaaaaaac taaggaaaca ttttctttgt      3000
ttcgagtaga taatgccagc ctgttaaacg ccgtcgacga gtctaacgga caccaaccag      3060
cgaaccagca gcgtcgcgtc gggccaagcg aagcagacgg cacggcatct ctgtcgctgc      3120
ctctggaccc ctctcgagag ttccgctcca ccgttggact tgctccgctg tcggcatcca      3180
gaaattgcgt ggcggagcgg cagacgtgag ccggcacggc aggcggcctc ctcctcctct      3240
cacggcaccg gcagctacgg gggattcctt tccaccgct ccttcgcttt ccttcctcg      3300 cccgccgtaa taaatagaca cccctccac acctcttc ccaacctcg tgttgttcgg      3360 agcgcacaca cacacaacca gatctcccc aaatccaccc gtcggcacct ccgcttcaag      3420
gtacgccgct cgtcctcccc ccccccctc tctaccttct ctagatcggc gttccggtcc      3480
atgcatggtt agggcccggt agttctactt ctgttcatgt ttgtgttaga tccgtgtttg      3540
tgttagatcc gtgctgctag cgttcgtaca cggatgcgac ctgtacgtca gacacgttct      3600
gattgctaac ttgccagtgt ttctcttttgg ggaatcctgg gatggctcta gccgttccgc      3660
agacgggatc gatttcatga ttttttttgt ttcgttgcat agggtttggt ttgccctttt      3720
cctttatttc aatatatgcc gtgcacttgt ttgtcgggtc atcttttcat gctttttttt      3780
```

```
gtcttggttg tgatgatgtg gtctggttgg gcggtcgttc tagatcggag tagaattctg    3840
tttcaaacta cctggtggat ttattaattt tggatctgta tgtgtgtgcc atacatattc    3900
atagttacga attgaagatg atggatggaa atatcgatct aggataggta tacatgttga    3960
tgcgggtttt actgatgcat atacagagat gcttttgtt cgcttggttg tgatgatgtg     4020
gtgtggttgg gcggtcgttc attcgttcta gatcggagta gaatactgtt tcaaactacc    4080
tggtgtattt attaattttg gaactgtatg tgtgtgtcat acatcttcat agttacgagt    4140
ttaagatgga tggaaatatc gatctaggat aggtatacat gttgatgtgg gttttactga    4200
tgcatataca tgatggcata tgcagcatct attcatatgc tctaaccttg agtacctatc    4260
tattataata aacaagtatg ttttataatt attttgatct tgatatactt ggatgatggc    4320
atatgcagca gctatatgtg gattttttta gccctgcctt catacgctat ttatttgctt    4380
ggtactgttt cttttgtcga tgctcaccct gttgtttggt gttacttctg caggtcgact    4440
ttaacttagc ctagggaagt tcctattccg aagttcctat tctctagaaa gtataggaac    4500
ttcagatcca ccgggatccc cgatcatgca aaaactcatt aactcagtgc aaaactatgc    4560
ctggggcagc aaaacggcgt tgactgaact ttatggtatg gaaatccgt ccagccagcc     4620 gatggccgag ctgtggatgg gcgcacatcc gaaaagcagt tcacgagtgc agaatgccgc    4680
cggagatatc gtttcactgc gtgatgtgat tgagagtgat aaatcgactc tgctcggaga    4740
ggccgttgcc aaacgctttg cgaactgcc ttttcctgttc aaagtattat gcgcagcaca    4800
gccactctcc attcaggttc atccaaacaa acacaattct gaaatcggtt ttgccaaaga    4860
aaatgccgca ggtatcccga tggatgccgc cgagcgtaac tataaagatc ctaaccacaa    4920
gccggagctg gtttttgcgc tgacgccttt ccttgcgatg aacgcgtttc gtgaattttc    4980
cgagattgtc tccctactcc agccggtcgc aggtgcacat ccggcgattg ctcactttt     5040 acaacagcct gatgccgaac gtttaagcga actgttcgcc agcctgttga atatgcaggg    5100
tgaagaaaaa tcccgcgcgc tggcgatttt aaaatcggcc ctcgatagcc agcagggtga    5160
accgtggcaa acgattcgtt taatttctga attttacccg gaagacagcg gtctgttctc    5220
cccgctattg ctgaatgtgg tgaaattgaa ccctggcgaa gcgatgttcc tgttcgctga    5280
aacaccgcac gcttacctgc aaggcgtggc gctggaagtg atggcaaact ccgataacgt    5340
gctgcgtgcg ggtctgacgc ctaaatacat tgatattccg gaactggttg ccaatgtgaa    5400
attcgaagcc aaaccggcta accagttgtt gacccagccg gtgaaacaag gtgcagaact    5460
ggacttcccg attccagtgg atgattttgc cttctcgctg catgaccta gtgataaaga     5520 aaccaccatt agccagcaga gtgccgccat tttgttctgc gtcgaaggcg atgcaacgtt    5580
gtggaaaggt tctcagcagt tacagcttaa accgggtgaa tcagcgttta ttgccgccaa    5640
cgaatcaccg gtgactgtca aaggccacgg ccgtttagcg cgtgtttaca acaagctgta    5700
agagcttact gaaaaaatta acatctcttg ctaagctggg ggtggaacct agacttgtcc    5760
atcttctgga ttggccaact taattaatgt atgaaataaa aggatgcaca catagtgaca    5820
tgctaatcac tataatgtgg gcatcaaagt tgtgtgttat gtgtaattac tagttatctg    5880
aataaaagag aaagagatca tccatatttc ttatcctaaa tgaatgtcac gtgtctttat    5940
aattctttga tgaaccagat gcatttcatt aaccaaatcc atatacatat aaatattaat    6000
catatataat taatatcaat tgggttagca aaacaaatct agtctaggtg tgttttgcga    6060
atgcgacctt cttatgtgct tctagtctcc aaatgtggtt gatagttatt ttgctctaag    6120
```

```
atcaacagta atgaagtata aatcatcgtt gtggtgtgct actcggttaa ttgagcatta    6180
acacacacaa acatgacgag gatggtataa tctccaaaaa tgtgtacttt gttaggtggg    6240
accctatagc cttgattaat gtgctatgtt aggcatgcct ggaaacgtgt gacgcatatg    6300
ttttgtgaac ctgttgatat tatatgtgct tttatattac catattttat taaaatacta    6360
atatttatta ctagtaagat ataacattct atctagctta aaaactaacc ataaatattc    6420
cataataact agatttacca aactaatata ctaaatatac ataataaata caaaattaac    6480
aagacaataa tcaatattta tgagcttaat atatttagac attatggttg gtcgacgata    6540
atcatgctaa cttttcgtaa ttgcttgatt gaaatatgct tagaataatg cctctttgtt    6600
ctacatggca aatagggacc attatggtgt aacaccctgg gaaccacaaa caccccgaaa    6660
tgctactaaa ctacacaact aaccttcata tataaaattt cgacagcatc tcctttgaaa    6720
atttgcatag acgtggaagc aacagagtat aaacagatat catgataaga aaacatacta    6780
gacattaata atctgctaga aatgggaaga atcctaactt gacgactgcg taactgacta    6840
gagtcacact tagctgaccc tagtcactta caactgactt cgtgtcctag gcttaggcta    6900
ctgctagtcc gcggtgtatc cgtgatcgag ttggcgccag acggaatctg ttctccatcg    6960
ctgacatcct cgagtagatc acattcaagc ttgatatcga attcctgcag cccatccctc    7020
agccgccttt cactatcttt tttgcccgag tcattgtcat gtgaaccttg gcatgtataa    7080
tcggtgaatt gcgtcgattt tcctcttata ggtgggccaa tgaatccgtg tgatcgcgtc    7140
tgattggcta gagatatgtt tcttccttgt tggatgtatt ttcatacata atcatatgca    7200
tacaaatatt tcattacact ttatagaaat ggtcagtaat aaaccctatc actatgtctg    7260
gtgtttcatt ttatttgctt ttaaacgaaa attgacttcc tgattcaata tttaaggatc    7320
gtcaacggtg tgcagttact aaattctggt ttgtaggaac tatagtaaac tattcaagtc    7380
ttcacttatt gtgcactcac ctctcgccac atcaccacag atgttattca cgtcttaaat    7440
ttgaactaca catcatattg acacaatatt ttttttaaat aagcgattaa aacctagcct    7500
ctatgtcaac aatggtgtac ataaccagcg aagtttaggg agtaaaaaac atcgccttac    7560
acaaagttcg ctttaaaaaa taagagtaa atttttacttt ggaccaccct tcaaccaatg    7620
tttcacttta gaacgagtaa ttttattatt gtcactttgg accaccctca aatcttttt    7680 ccatctacat ccaatttatc atgtcaaaga aatggtctac atacagctaa ggagatttat    7740
cgacgaatag tagctagcat actcgaggtc attcatatgc ttgagaagag agtcgggata    7800
gtccaaaata aaacaaaggt aagattacct ggtcaaaagt gaaaacatca gttaaaaggt    7860
ggtataaagt aaaatatcgg taataaaagg tggcccaaag tgaaatttac tcttttctac    7920
tattataaaa attgaggatg ttttttgtcgg tactttgata cgtcattttt gtatgaattg    7980
gtttttaagt ttattcgctt ttggaaatgc atatctgtat ttgagtcggg ttttaagttc    8040
gtttgctttt gtaaatacag agggatttgt ataagaaata tctttaaaaa aacccatatg    8100
ctaatttgac ataattttg agaaaaatat atattcaggc gaattctcac aatgaacaat    8160
aataagatta aaatagcttt ccccgttgc agcgcatggg tatttttct agtaaaaata    8220 aaagataaac ttagactcaa aacatttaca aaaacaaccc ctaaagttcc taaagcccaa    8280
agtgctatcc acgatccata gcaagcccag cccaacccaa cccaacccaa cccacccag    8340 tccagccaac tggacaatag tctccacacc ccccactat caccgtgagt tgtccgcacg    8400
caccgcacgt ctcgcagcca aaaaaaaaa aagaagaaa aaaagaaaa agaaaaaaca    8460 gcaggtgggt ccgggtcgtg ggggccggaa acgcgaggag gatcgcgagc cagcgacgag    8520
```

| | |
|---|---|
| gccggccctc cctccgcttc caaagaaacg cccccatcg ccactatata cataccccc | 8580 |
| cctctcctcc catccccca accctaccac caccaccacc accacctcca cctcctcccc | 8640 |
| cctcgctgcc ggacgacgag ctcctccccc ctccccctcc gccgccgccg cgccggtaac | 8700 |
| cacccccgccc ctctcctctt tctttctccg ttttttttt ccgtcacggt ctcgatcttt | 8760 |
| ggccttggta gtttgggtgg gcgagaggcg gcttcgtgcg cgcccagatc ggtgcgcggg | 8820 |
| aggggcggga tctcgcggct ggggctctcg ccggcgtgga tcaggccgg atctcgcggg | 8880 |
| gaatggggct ctcggatgta gatctgcgat ccgccgttgt tggggagat gatggggt | 8940 |
| ttaaaatttc cgccatgcta aacaagatca ggaagagggg aaaagggcac tatggtttat | 9000 |
| attttatat atttctgctg cttcgtcagg cttagatgtg ctagatcttt ctttcttctt | 9060 |
| tttgtgggta gaatttgaat ccctcagcat tgttcatcgg tagttttct tttcatgatt | 9120 |
| tgtgacaaat gcagcctcgt gcggagcttt tttgtaggta gaaggatcca cacgacacca | 9180 |
| tgtccccga gcgccgcccc gtcgagatcc gccggccac cgccgccgac atggccgccg | 9240 |
| tgtgcgacat cgtgaaccac tacatcgaga cctccaccgt gaacttccgc accgagccgc | 9300 |
| agacccccgca ggagtggatc gacgacctgg agcgcctcca ggaccgctac ccgtggctcg | 9360 |
| tggccgaggt ggagggcgtg gtggccggca tcgcctacgc cggcccgtgg aaggcccgca | 9420 |
| acgcctacga ctggaccgtg gagtccaccg tgtacgtgtc ccaccgccac cagcgcctcg | 9480 |
| gcctcggctc caccctctac acccacctcc tcaagagcat ggaggcccag ggcttcaagt | 9540 |
| ccgtggtggc cgtgatcggc ctcccgaacg accgtccgt gcgcctccac gaggccctcg | 9600 |
| gctacaccgc ccgcggcacc ctgcgcgccg ccggctacaa gcacggcggc tggcacgacg | 9660 |
| tcggcttctg gcagcgcgac ttcgagctgc cggcccccgcc gcgccggtg cgccggtga | 9720 |
| cgcagatctg agtcgacctg caggcatgcc gctgaaatca ccagtctctc tctacaaatc | 9780 |
| tatctctctc tataataatg tgtgagtagt tcccagataa gggaattagg gttcttatag | 9840 |
| ggtttcgctc atgtgttgag catataagaa acccttagta tgtatttgta tttgtaaaat | 9900 |
| acttctatca ataaaatttc taattcctaa aaccaaaatc cagtggcgag ctaatgcggc | 9960 |
| ccgaataact tcgtatagca tacattatac gaagttatac ctggtggcgc cgctagggc | 10020 |
| tgcaggaatt cctgcagccc ggggatcca ctagttctag agcggccgac ctcgacagat | 10080 |
| ctaagcttac tagtgccgtg ggtcgtttaa gctgccgctg tacctgtgtc gtctggtgcc | 10140 |
| ttctggtgta cctgggaggt tgtcgtctat caagtatctg tggttggtgt catgagtcag | 10200 |
| tgagtcccaa tactgttcgt gtcctgtgtg cattataccc aaaactgtta tgggcaaatc | 10260 |
| atgaataagc ttgatgttcg aacttaaaag tctctgctca atatggtatt atggttgttt | 10320 |
| ttgttcgtct cctaatattt gcctgggatc aaatttatt ggctggtgtt catttgacct | 10380 |
| ccatgttctt gctaggctcc attttttact ctacagccat aatatgtttg attgtttggt | 10440 |
| ttgttctttg ttgtacacct ggttctgtcg agcttagttt tcgacactgg cttacagctt | 10500 |
| aacatgttgc tattttattg ggttctgatt gctatttat tgggttctga ttgctagttt | 10560 |
| ttgctgaatc caaaaaccat gttatttatt taagcgatcc aggttattat tatgatggtg | 10620 |
| gctaagtttt ttttttcca agggtaaatt ttctggattc tccagtgttt ctgtggccga | 10680 |
| attcactagt gattcagatc tgatatcgat gggcccacta actatctata ctgtaataat | 10740 |
| gttgtatagc cgccggatag ctagctagtt tagtcattca gcggcgatgg gtaataataa | 10800 |
| agtgtcatcc atccatcacc atgggtggca acgtgagcaa tgacctgatt gaacaaattg | 10860 |

```
aaatgaaaag aagaaatatg ttatatgtca acgagatttc ctcataatgc cactgacgac    10920
gtgtgtccaa gaaatgtatc agtgatacgt atattcacaa ttttttttatg acttatactc    10980 acaatttgtt tttttactac ttatactcac aatttgttgt gggtaccata acaatttcga    11040
tcgaatatat atcagaaagt tgacgaaagt aagctcactc aaaaagttaa atgggctgcg    11100
gaagctgcgt caggcccaag ttttggctat tctatccggt atccacgatt ttgatggctg    11160
agggacatat gttcgcttaa gcttggtcac ccggtccggg cctagaaggc cagcttcaag    11220
tttgtacaaa aaagcaggct ccggccagaa tctcactgac tagctaaaca gcggccgctt    11280
ttaagtatga ccaattttta agtataaacc cctcacgatt ggttattttt taagtataa    11340 ccaattttta agtataaacc cctcaccaat ttttaagtat aaacctagcg actaataaac    11400
acaacttctt gccaaagtgt gagcatcacc attggatctg cgcccctcac gaacagtctt    11460
cgccggggta aaattctcca aattaaagtc atcttgatgt ccttgatcac ctgtccataa    11520
ggcccaatcc cagctccacg tatacttctg ataagattga catagtcact tgcatgccag    11580
tgtggaactc tggatgccta ggtcagaggc tagtgactgg ccttcccggc atgctagcat    11640
gtagcatgcc aaggatctgg ctgctccagg tttgttatgc ctgacatcac catagggatg    11700
agagcaagta taataatagg ctgtaagctt taaatgctca ggtggagaaa aaaggagag    11760 gagaggagag agaaaagtgg gctataagct tatagctgtg ttagacataa gaatcagaaa    11820
cttcgtatga gagacaggtg agctatatat taataacaaa gagctaacta ttatatgagt    11880
gaaccgagag aaggctgtaa aaaaacttac acaatcaacg atcgacatta ttattaacct    11940
tgctctgtct tgcgagacct ctttgacaaa gctacatcaa tgccggccaa gtgccttggg    12000
atttgggaat ggcttctttc ctcccttcct cggttgtccc ccaaggccta ggcttgccac    12060
gctgtattca gtcgcagccg cctttacttt tgccctttgt ggaagttttg taataaatgg    12120
tctgattcta tcttcggata gatgaagccg gatgtttcat ccattatcta aaaaaaagtt    12180
ggttgctttg ctgagctaag aaagtgtaat ccagagtgcc cgtaacgtat tcatgtacat    12240
aactattatc taatataaat cttctttttgt cgcaaaaaaa ggtcggccca tcagaacaaa    12300
tgatcaatgt aaggcccaaa atttgtgtct caaatgtcat ttacgtttcc aagctaaaca    12360
aaaacacagg attcatataa ttttgctggt ggcttaggct tcgtccaata gtgcttagtt    12420
taatttgtat atacctgcac catggtattc gtctggcctt ggatcttgcg catcaattgc    12480
ctatggacga tgatcgcagc cacgccacat tcatttttaa tcgccatttg cttgacaccc    12540
aatgcctctg caccacttgc gcacgctacg caccgtctga tacgccaaga tcccgagcta    12600
aaataacacc caatcatcag atgaaaacaa gcgcgagtgc gagccagccc atggcagcga    12660
tcttggccat ttgcggagcc aactgaaagc cgtgcacaaa atattcgaca ccgtataagg    12720
gaaaacacta gttatacgag gtgggcaata atccagatct cggactcttc ctaacccggt    12780
tcacatgcat agcatatatg atggccggcc ggggttcaca tgaacgccat cccgtgccct    12840
agtgcactga tttcttaatt tcgaattta agtatgacca atttttaagt ataaccccct    12900
cacgattggt tatttttta agtataacca atttttaagt ataaccccct caccaatttt    12960
taagtataaa cctagcgact aataaacaca acttcttgcc aaagtgtgag catcaccatt    13020
ggatctgcgc ccctcacgaa cagtcttcgc cggggtaaaa ttctccaaat taaagtcatc    13080
ttgatgtcct tgatcacctg tccataaggc ccaatcccag ctccacgtat acttctgata    13140
agattgacat agtcacttgc atgccagtgt ggaactctgg atgcctaggt cagaggctag    13200
tgactggcct tcccggcatg ctagcatgta gcatgccaag gatctggctg ctccaggttt    13260
```

```
gttatgcctg acatcaccat agggatgaga gcaagtataa aataggctg taagctttaa    13320 atgctcaggt ggagaaaaaa aggagaggag aggagagaga aaagtgggct ataagcttat    13380
agctgtgtta gacataagaa tcagaaactt cgtatgagag acaggtgagc tatatattaa    13440
taacaaagag ctaactatta tatgagtgaa ccgagagaag gctgtaaaaa aacttacaca    13500
atcaacgatc gacattatta ttaaccttgc tctgtcttgc gagacctctt tgacaaagct    13560
acatcaatgc cggccaagtg ccttgggatt tgggaatggc ttctttcctc ccttcctcgg    13620
ttgtccccca aggcctaggc ttgccacgct gtattcagtc gcagccgcct ttacttttgc    13680
cctttgtgga agttttgtaa taaatggtct gattctatct tcggatagat gaagccggat    13740
gtttcatcca ttatctaaaa aaagttggt tgctttgctg agctaagaaa gtgtaatcca    13800
gagtgcccgt aacgtattca tgtacataac tattatctaa tataaatctt cttttgtcgc    13860
aaaaaaaggt cggcccatca gaacaaatga tcaatgtaag gcccaaaatt tgtgtctcaa    13920
atgtcattta cgtttccaag ctaaacaaaa acacaggatt catataattt tgctggtggc    13980
ttaggcttcg tccaatagtg cttagtttaa tttgtatata cctgcaccat ggtattcgtc    14040
tggccttgga tcttgcgcat caattgccta tggacgatga tcgcagccac gccacattca    14100
tttttaatcg ccatttgctt gacacccaat gcctctgcac cacttgcgca cgctacgcac    14160
cgtctgatac gccaagatcc cgagctaaaa taacacccaa tcatcagatg aaaacaagcg    14220
cgagtgcgag ccagcccatg gcagcgatct tggccatttg cggagccaac tgaaagccgt    14280
gcacaaaata ttcgacaccg tataagggaa aacactagtt atacgaggtg ggcaataatc    14340
cagatctcgg actcttccta acccggttca catgcatagc atatatgatg gccggccggg    14400
gttcacatga acgccatccc gtgccctagt gcactgattt cttaatgtcg acgggccgct    14460
tttaagtatg accaatttt aagtataaac ccctcacgat tggttatttt tttaagtata    14520
accaattttt aagtataaac ccctcaccaa ttttaagta taaacctagc gactaataaa    14580
cacaacttct tgccaaagtg tgagcatcac cattggatct gcgcccctca cgaacagtct    14640 tcgccgggt aaaattctcc aaattaaagt catcttgatg tccttgatca cctgtccata    14700
aggcccaatc ccagctccac gtatacttct gataagattt acatagtcac ttgcatgcca    14760
gtgtggaact ctggatgcct aggtcagagg ctagtgactg gccttccgg catgctagca    14820 tgtagcatgc caaggatctg gctgctccag gtttgttatg cctgacatca ccatagggat    14880
gagagcaagt ataataatag gctgtaagct ttaaatgctc aggtggagaa aaaaaggaga    14940
ggagaggaga gagaaaagtg ggctataagc ttatagctgt gttagacata agaatcagaa    15000
acttcgtatg agagacaggt gagctatata ttaataacaa agagctaact attatatgag    15060
tgaaccgaga gaaggctgta aaaaaactta cacaatcaac gatcgacatt attattaacc    15120
ttgctctgtc ttgcgagacc tctttgacaa agctacatca atgccggcca agtgccttgg    15180
gatttgggaa tggcttcttt cctcccttcc tcggttgtcc cccaaggcct aggcttgcca    15240
cgctgtattc agtcgcagcc gcctttactt ttgccctttg tggaagtttt gtaataaatg    15300
gtctgattct atcttcggat agatgaagcc ggatgtttca tccattatct aaaaaaaagt    15360
tggttgcttt gctgagctaa gaaagtgtaa tccagagtgt cgtaacgta ttcatgtaca    15420 taactattat ctaatataaa tcttcttttg tcgcaaaaaa aggtcggccc atcagaacaa    15480
atgatcaatg taaggcccaa aatttgtgtc tcaaatgtca tttacgtttc caagctaaac    15540
aaaaacacag gattcatata attttgctgg tggcttaggc ttcgtccaat agtgcttagt    15600
```

-continued

| | | | | |
|---|---|---|---|---|
| ttaatttgta | tatacctgca | ccatggtatt | cgtctggcct | tggatcttgc gcatcaattg | 15660 |
| cctatggacg | atgatcgcag | ccacgccaca | ttcattttta | atcgccatttt gcttgacacc | 15720 |
| caatgcctct | gcaccacttg | cgcacgctac | gcaccgtctg | atacgccaag atcccgagct | 15780 |
| aaaataacac | ccaatcatca | gatgaaaaca | agcgcgagtg | cgagccagcc catggcagcg | 15840 |
| atcttggcca | tttgcggagc | caactgaaag | ccgtgcacaa | aatattcgac accgtataag | 15900 |
| ggaaaacact | agttatacga | ggtgggcaat | aatccagatc | tcggactctt cctaacccgg | 15960 |
| ttcacatgca | tagcatatat | gatggccggc | cggggttcac | atgaacgcca tcccgtgccc | 16020 |
| tagtgcactg | atttcttaat | cccatccagc | atgctcttca | attttggtgc tcacccttac | 16080 |
| gggtatgccc | tcactgcctt | ttataattgt | ataagggaaa | tattattcaa tataatgtcc | 16140 |
| taaaaattgg | caatatcaat | ctaaaaatcg | ttatgaatag | gatgtaaaca aagctactat | 16200 |
| ctgtccatat | ataacgtcac | aggaaggaca | aaaaattcag | tcagcgatcg agaacggcaa | 16260 |
| agaaaaacca | tattattgtt | gcttgccgac | ataaatttaa | gtataggaca aaaaaaaaag | 16320 |
| ccacatcata | ttcatatacta | tgggcttacc | agacaaaatg | aaataaacgt gtgcatgcat | 16380 |
| gcatgcatgg | tacgaacgtc | tggatagagt | ctccgagctg | agtgtggtcc gacgtggaag | 16440 |
| tgtacgtctc | aacacacgac | gcatgtgacc | gacaagggca | agttgaagtc tatgcatgga | 16500 |
| tgggcctgag | cgccgcgctg | aatgaatctg | gacgggtggt | agggcatctc ggtgggcaaa | 16560 |
| acaaataact | ccgtgtgctg | catggctgcc | tttggaatct | ttgcatgcag ctgtgtgctg | 16620 |
| aactgaaacc | cttcgctcta | tctatataaa | cagatgccct | tcgctctcgt ctcagcaggc | 16680 |
| agcatcgtct | caagttttgt | tctcctctcc | tagctagcca | gcacctgcag atctgctcgt | 16740 |
| tgccttggta | attcatcatg | tagtacgtag | catcagctag | tatttatctc aagtatatat | 16800 |
| atacgcatat | gtgtcgtcgc | agtactttcc | cttatctctc | tatacacact acacgcatac | 16860 |
| ataccaatac | catccgtctt | aactcttaat | ctttgcctgc | atacgtacac tgcacgtacg | 16920 |
| tactgcaggg | ctactgattt | tgtggaacga | agcggtcgag | accggtgatc ttgtaaggtt | 16980 |
| cccttccctc | ctcccctcac | accctgttc | gtgttccttc | ggatcggatc tcagtggtga | 17040 |
| tgttagacgt | ccgcggctgc | ctacgtagtg | gcattgccgc | ccgaaaggtt tgtttaggtg | 17100 |
| gggtagatcc | gaaacaggcc | ggatctggac | catgtccgcg | gcgggcggc gggacttgat | 17160 |
| cgcgtagctg | tcgtgtgcat | ttctccctac | cagtggcgga | atcggcgatg tggacctaag | 17220 |
| ggctaaggct | tatctgctgc | cttgaccatt | tcgtcgctga | caaaaacaaa gtgacaatca | 17280 |
| tgccgttctc | tgtttgttta | tctggatcgt | tattacgctg | tgaatcctgc gatatgtggc | 17340 |
| taagtgattt | ttcttctttt | tctggggca | gtttagcctt | tgacccagtc ctaggtgtgg | 17400 |
| tcactaggac | tgtgtagcat | gatgagtgag | gttgcagcag | gctgattgct agtgacgtt | 17460 |
| ttttcccca | atttgttagg | ttttcacgct | ccaggttgtg | caagtaattt tgctagtgat | 17520 |
| tgtgtgatcc | atcttcaacg | ttgaaccttg | ttttcccc | taaaccccc aacaggaaat | 17580 |
| cttgccccga | cttctattgc | aaaaattgta | acgcttagca | ccctgattga ctcaattcct | 17640 |
| gtcactaggc | atgctcggtc | aaaagcagat | gatttaccac | ttagaaactg ccctgcccct | 17700 |
| gctttccaca | tagcatttcg | aactttttga | ctactattga | cacccccta acttgccgaa | 17760 |
| ctatttctct | cttcagctac | tatttaccta | gttataatta | cataaatgtt tgtgtgtatc | 17820 |
| ttgtgcaggg | atccgccatg | gcagagccga | acaagggtgg | agcacctgcg atgaagaacg | 17880 |
| tcgccaagcc | gtcgaccaaa | cgcctgatcc | cgagctcgat | agccgcttcg agccagacta | 17940 |
| gcgccaacgc | tctgacggag | cccttcctg | ggtctgacgc | gatcggccag agctacgacg | 18000 |

```
cattcgggtt cttcgccaat ccccgcagca tcatgaagga gctgttcgag ttcagcccac   18060
aggaggagat cgtcgtcgaa ggcaacacct ggcttctcag cagcgacttc gtctacaccg   18120
ccatccgcga cacagagacc tcgaccgtct cgaggcgcac caaggacgac tacagcaagg   18180
agctggccgt gaaggtgaag ctcagcggaa gctacggcta cttcagcgct agcgtggaga   18240
gcgacttcag ccagagcatc agcgacgcta ccgacacgac gtacaccagc gtccgcaccc   18300
acgtcaacaa gtggcgcctc agcctcaagg acgacgtcgg agctctccgg agcaagctcc   18360
ttcctggtgt caagcaggct ctcgctacga tggacgcaac ccagctcttc gacacgttcg   18420
gcacccacta cgtcagcgag gtcctcgtcg gtggaagagc cgactacgtc gccaccacca   18480
agaccagcgc cttcagctcg agcacctcca tcagcgtcgc tgcagaggcg tcgtttcaga   18540
gcatcgcagg aggcgaagtc agccccgaga gcaaggtcct cgccgagatg ctgcgcgaga   18600
actccagcac acggctctac gcactgggag gctcagcact cccgaacatc acggacccag   18660
cgacctacaa cgcctggctg gagagcatcg acaccatccc ggtcttctgc ggcttcaccc   18720
agaactccct caagtcgatc agcgagctcg cggattcagc ccaacgcaga gacgcactcg   18780
cgaaggcatc ccagtcgtac atccccagct acgtcactcg cccagcagtc gtgggcctcg   18840
aggtcatcat ctccgactcc aactccgaga gccctccata cggctacacc cggatcgact   18900
acgacctcaa ccgcaatgcc ggaggcaagt acgtcttcct ctgctacaag cagaagaaca   18960
tctccgtcgg aggtgacgca gacgcgatca cggacgtcct cgtcgtctac ggcaacgacc   19020
ggaacccaag cgtgccctca ggctacacca agatcgacaa ggacctgaac tccggagctg   19080
gagggaagta catctacttc tgctactcca aggacaagcg caagcaggag gagggccttc   19140
cgatacgcgg acttcgcgtc gttggaccac accctacgtc agtggcaccg tacggcttca   19200
gcaagatcga catcgacctc aacatgggcg caggtgggga cttcatctac ctctgcaagt   19260
cgcggcacct cgagtgagtt aaccccgggt caacccatca ggaaggatga agcgcccctc   19320
attttgtgcc ctaggtcgtg gattgctgga ttttaatttt acacatttcc ttgtcgatcc   19380
tttctgctgt gtgtggttcg agaatgttag tgtgttatcg caagatctgg gtgtttggaa   19440
gttatctcat tattgggcct cataaattca taattcttgc cagttagtga caactgtagc   19500
ttaggtttac ttctgcttgt agtacatcgc ctagatcgtg ggagtccctc ttttcagacg   19560
aatgtcatga aacattggtt tttggaaatg attaggaaga catttgctgt tttgtcgact   19620
gctgtttttt acggccaagt tcagagtttt tttttcatg tacaaagtat cagcagttaa   19680
attatgttac ctttaccatg gttcttcata tttgttttcc ttccattgct caatctatgt   19740
catcttttga aatggtttgg aaggcatcct ttataggata tatagatata gatttgaagc   19800
ataattgtta ggataagaca ccagctagcc tatgctgcaa cgcacattat tcgaccctta   19860
ataacaacag gtgatttta tattataaaa aagttggaaa agtatacaca agaattttc    19920 aaaagaaggg taaagggaa cagccctcct gctcgacaat tggaattggt gtcccgcata   19980 attttttct gcctttgaga attcaggcgt ctctggattc tagttcacca tttaccaatt   20040
agaaggaata ctatgtatgt ataattctac aatctgcatt ctacacaatc cttctatttt   20100
ctgaatatag ttgcaagact agggctctct tatagtattt ctaattatag ccgctttgca   20160
aagtactgtc atatttgatt aggggtattg gaaagaagga gaaagggtg acaccctgct   20220 tgacaattgg aattgataag cagccagggt accaaggcgc gaaacagccc cctccggcgg   20280 tgtccccac tgaagaaact atgtgctgta gtatagccgc tggctagcta gctagttgag   20340
```

```
tcatttagcg gcgatgattg agtaataatg tgtcacgcat caccatgcat gggtggcagt   20400
ctcagtgtga gcaatgacct gaatgaacaa ttgaaatgaa aagaaaaaag tattgttcca   20460
aattaaacgt tttaaccttt taataggttt atacaataat tgatatatgt tttctgtata   20520
tgtctaattt gttatcatcc atttagatat agacgaaaaa aaatctaaga actaaaacaa   20580
atgctaattt gaaatgaagg gagtatatat tgggataatg tcgatgagat ccctcgtaat   20640
atcaccgaca tcacacgtgt ccagttaatg tatcagtgat acgtgtattc acatttgttg   20700
cgcgtaggcg tacccaacaa ttttgatcga ctatcagaaa gtcaacggaa gcgctgcaga   20760
aacttatctc tgttatgaat cagaagaagt tcatgtctcg tttcatttaa aactttggtg   20820
gtttgtgttt tggggccttg taaagcccct gatgaataat tgttcaacta tgtttccgtt   20880
cctgtgttat accttctttt ctaatgagta atgacatcaa acttcttctg tattgaaatt   20940
atgtccttgt gagtctcttt atcatcgttt cgtctttaca ttatatgtgc tacttttgtc   21000
taatgagcct gaaaagtggc tccaatggta cgcactggaa gatttgttgg cttctggtag   21060
atatagcgac agtgttgagc ttgtaatatc atgtctctta ttgctaaatt agttcctttc   21120
ttaacagaaa ccttcaaagt ttttgttttt gttttcattt acctaatgta cacatacgct   21180
ggccatgact aacaacatgt ccaggcttag agcatatttt tttctagctt aaattgttaa   21240
cttgtcattc agtaaaatcc gagaattgtg aagctctaat tgaagctaat tcgttttata   21300
aagtcagtta aaaagtatac taaattatcc aacttttctt caaaatctca aaattctatg   21360
acaaaacgat agtctttgtt tatgtcagta ccacaaagag gtggaaaaaa acaccaaaaa   21420
aacaataagc aaactataca ctgagaagaa aaataaaaga gagctcaata gatgttttat   21480
actaacggta gattagatca aagatccaag ctttactcta catagagcag aacccagaat   21540
cccttcatat ctcttttatt ctagcaccga taatctactg aaaagaagac acttagagct   21600
ctgtctcttt gtcaaagaag tcccagccgt catccagaag ctccttacgt tcattaacag   21660
agaattcgac aaagcagcat tagtccgttg atcggtggaa gaccactcgt cagtgttgag   21720
ttgaatgttt gatcaataaa atacggcaat gctgtaaggg ttgttttta tgccattgat   21780 aatacactgt actgttcagt tgttgaactc tatttcttag ccatgccaag tgcttttctt   21840
attttgaata acattacagc aaaaagttga agacaaaaa aaaaaacccc cgaacagagt   21900
gctttgggtc ccaagcttct ttagactgtg ttcggcgttc cccctaaatt tctccccta   21960 tatctcactc acttgtcaca tcagcgttct ctttccccct atatctccac gctctacagc   22020
agttccacct atatcaaacc tctataccc accacaacaa tattatatac tttcatcttc   22080
aactaactca tgtaccttcc aatttttttc tactaataat tatttacgtg cacagaaact   22140
tagcaaggag agagagagcg gggtgaccaa gcttggcgcg ccattctatc actagctagc   22200
tgctaattat tcccgggcac ccagctttct tgtacaaagt ggccgttaca gaatcactga   22260
ctagctaatc tagcggccgc tcaagcttcg gcatgcaatt cgcataccta cagtacaacg   22320
tggccaaagt catcatttaa tgagctctcg ggcgcgccgt ctcactagct agctgctaac   22380
gttcccgggc aactttatta tacaaagttg atagatccta caggccagaa tggcctctgg   22440
attcagcggc ctagaaggcc gaagtacttg gtcttcctaa tatcggaccg aggaccgatt   22500
aaactttaat tcggtccgtc aatattcacc gaagcgacta attaactagc tgtcccacgg   22560
cctaactagc acttaatccc ctagcctaac ctaagagcgc taatctaggc tagtggtcac   22620
ttagggcttt aaggctagcg tatacgaagt tcctattccg aagttcctat tcttcaaaaa   22680
gtataggaac ttctgtacac ctgagctgat tccgatgact tcgtaggttc ctagctcaag   22740
```

```
ccgctcgtgt ccaagcgtca cttacgatta gctaatgatt acggcatcta ggaccgacta   22800
gctaactaac tagggcgcgc catgaggagc aatcattgtt caagacatga tgcaaagcta   22860
gaaaactttg attgtggccg tcctaattgt gaagtttagg ccgggggaa cttcatgaac    22920 cctatcgaag cttaattagt tctttttgt tgttagccat gtttgtattg tagtttaggt    22980
gaacaacatg acgccgcacc cgcgatctca gggctcgtcc ccacacagga gggcacgtcg   23040
tcgtcttcgc cgccgagcat cagagattca gagcacgtac acgcacatct caagcaaacg   23100
gagtagtacg tcctactcct acgtacatac ctagccgacg acctttatgt gcacaccacc   23160
actgctctgc tgcccggcct ctccgtcgtc cgttcatcac cagctggtct ggtccttcaa   23220
tttccatgcg tcggtccgaa gtcaacattt tccgtcaatt catggccaaa ggctacaact   23280
aacattgttt aatgtcgact gttttttttt tgttaatgtg acgccgtgtt ttttttgtta   23340
ttgctagaac actgtttaat gtcaaactgt tttaagtcca tgggacgcct cagcaatagt   23400
agccttttgt taatgtgacg ccgcatcaat caactaatta aagcccttaa ccatctgtgt   23460
ctcattgtta ccggcatcac ctaaacaaca gatcacggct ctacgagcaa cgtacataac   23520
agtaaactaa tggcctgatc tgctgggcta gtagggccac agcaaacacta gctgaacgta   23580 tgcagcggcg gcggcggcac catccaagta actcaagcga gcacggttga acaatacttg   23640 aaccttttg tcccaatcca ctttagaaaa ctaagaaatt catatcggag aaaggtcgaa    23700
gaatggtttg agaaaagact cggtagcttc cccaccaagt ctcacaatag aaacattatg   23760
aaaatattta cccttcataa ccctaatatg acccttcttc gcagtcgact tctcaaagac   23820
gacgtggctt ggtttctagg gtcgttcttc ggcatcaccc tcaaaatcaa agtcctcgct   23880
atcctcagaa tcgttgacat tccgaccaat attttataag taatcttcgg aatattactc   23940
ttctccatag cctcctggaa cccagcaagc gcaaactctt cactcttgct cccctcgacc   24000
atcatagcca aaaccaaata accaatgaat ctaaaacggt cacaattgat aataataacc   24060
ttcggtttta aagcgctagc tattctagca acaaaatagg tgaatggtgt gataattgcg   24120
catacgattt tcattctatt tataataaaa gccaggccag ggtcgaataa aaatataaa    24180 actaccactg caaaatgggc ctcgcatttc aagtatctcg atgattagct taaggaaggt   24240
gttttttcaa ccttcgacat aaggcctcg ttcatttctc agtttgagtt cgttgcaaga    24300
aaacaaacta atactgggag gggctagttt tggggccttc atcatttgaa ggttctcaaa   24360
acactaatta accattgttt catgatacat ctctaaaagt gttacaggtg cttcagtaaa   24420
aaccaccttc gaaataaatc gagcaacgac gaaggtacat tctactagc ggataaaact    24480 ggtcttgggc cgaggcagca tacaaagaag cttcgcctgt gcgcgcaagt ggcagaggtg   24540
ttagccgaag tcgataactt tggcaacaac agaagaggat ggagaaaata cattattatc   24600
ctgatggtat ttgtaaacaa tgtttgtaaa accttggggc atgattataa ttctatataa   24660
agacagttca ttttcctata aataggtgag cagtaccctg cataaggcat cttttttgagg  24720 ggtgatcact tcgtttaact tagcttacag agaacctttg taccatcttg tgtgtggagc   24780
tgaaggtatg cttgtacacc tttatcaaga gagatagagt aaattgctaa ggcatataag   24840
atgagttgaa tatgaagtta cactttg                                        24867
```

<210> SEQ ID NO 3
<211> LENGTH: 24867
<212> TYPE: DNA
<213> ORGANISM: Artificial Sequence
<220> FEATURE:

<223> OTHER INFORMATION: Synthetic

<400> SEQUENCE: 3

```
cgtactgcac tgccaccatt caagacaagc tatggtcgtc gccgtgaacg tgagccgcgc      60
atcgttgaag gctaggtcca cgaggaggta gacaagggca catgcgctcc caagagcttg     120
ttcgtgttcg tgacccgacg accgcgcgcg tttgtccgtg ggctcgtggg acgccagcag     180
cccacgcgaa acggttcccc tgccgcgcgc gcgcgcgccc ggtgcatggc tctcctcagc     240
ctccgaatgg agtcatcacc gtcgacgcct cgacggcgcg gaggtgacca aataaggtcc     300
ggctgctcgc agccgtggca cgaaacgagg acacacggac tggtaggagg ctaggggggg     360
cacggacaag accgctccgt tccgttgcct ctcccgcgct ctgcgaggga tgatgcatgg     420
gcagcgcgcg gacacacgga ctggcagcgg ccctgtaccc acgtcgcagt gccgggatcc     480
gcgcctacca cggcacgatc agcgtcatca tggcacaatc attcacgaac ctcccagtcc     540
cagcggattg cacgccgaaa atcgtcctc tagaagaaag cttttctcg tcgcacatcg      600
gcgcttctgc tcggcacggc atgtgaaact gtcaggcac agggggtagt ttactgacaa      660
ggtttgattt cttttccggc tgctgagcac ggtccgcgac tgggagcaaa ttcaatgccc     720
ttgctttctc ccgtcccggc ccattcaaac cgggccgtcg ttttagtttc tttttatgtt     780
ttacttggtt ttagcggcga ggcgatgcaa cgaagaccac agcagcaaac tactattgtt     840
tcagggtcat ttctaataca ctctccgtcc taaaatatta ggtggcgctt ggcagagttt     900
ccacagcttc gctcagagcg agaatcactc ttactgagct aaatgataaa aatcggaact     960
gcttcatgtt gagagtggag tgaatctagt ctacactatg tattagaaag tgagagaaaa    1020
aaaacatgct tcccactaca ctactcccaa catgctcccc actctttaac ccctcatgaa    1080
tcatttcaca gcctatttgc caaacaattt tcgtcaaata tattcacttc tagtagaaa    1140
tcactcagaa tcaccaatca gctctcggaa ctagagaatt gatcaaagac aaactctatt    1200
accttcaatg atatgtggtt atgattcatg ttggcaagct gtgatcctgt tgctgctgtt    1260
cccctggtac ttttttttt gtgtgccggt tgagtttta tagttatgt tgtgctgcat     1320
atgaatgagt tttggtagtt accgtggttg ccgttcacag cggcgttgcc tgctgttcat    1380
atgttggcaa tccgtgaatt tgcatgcttc tatatatgag tttggtgttc aattgtactt    1440
atatactacc aaaaaatacc atagtttcag tgggctgaag aaattaaaac ccatgcatgc    1500
tagtaatgtc atagctaggt gtataccatg gttttccaat accaaactta gctaccaaac    1560
acatactact gcatctgtat atataatgca ctggtgtgca gccgtcagcc gtgtgccttc    1620
tgaagcgtga aacctggtaa aaaaaaaaaa cggggaaggc aagaagcatc agggcaggca    1680
ggaggatcct agtacatatc ctacttactg gcttgcagca aggctagctg atggctgcgt    1740
gcgtgcttac atgatgatga tcatgcgtgt cgttcgtact cgtacgagga tcgaggaaag    1800
acaccataac tcaccttcaa cagacaccct tcgttaggag catgcacgga tagatggcgt    1860
ctagcatatc gataggacat gacaagtggt acgatccccg tcacatgtcc atggaggcat    1920
ctgatatgga cacggcgtgt atctatcgcg gctggaacag aaccagcgct cgcgcggcgg    1980
tcggcgggag ggacagacct tggctccgtg cgttcaggtt gtgcttgtgc cgcgcgccac    2040
gcacggtctc cgccgcctgc agctgaaatt ttagatttac atcctatccc tttattttt    2100
ttatttgtca caattcagtt caaaaatgaa gaacggaggt agtgcatcct ttgtgagact    2160
aatgaaaatc acatctggat cctgaaatcg gcgtcgtaac ctacaaggcc acggactgga    2220
ttagatagtg gtccatggtg cataatgagg atcgaggggt acctcactga ctagctaatc    2280
```

```
gagctagtta ccctatgagg tgacatgaag cgctcacggt tactatgacg gttagcttca    2340
cgactgttgg tggcagtagc gtacgactta gctatagttc cggacttacc gataacttcg    2400
tatagcatac attatacgaa gttatggcgc cgctagcctg cagtgcagcg tgacccggtc    2460
gtgcccctct ctagagataa tgagcattgc atgtctaagt tataaaaaat taccacatat    2520
ttttttttgtc acacttgttt gaagtgcagt ttatctatct ttatacatat atttaaactt    2580
tactctacga ataatataat ctatagtact acaataatat cagtgtttta gagaatcata    2640
taaatgaaca gttagacatg gtctaaagga caattgagta ttttgacaac aggactctac    2700
agttttatct ttttagtgtg catgtgttct ccttttttttt tgcaaatagc ttcacctata    2760
taatacttca tccattttat tagtacatcc atttaggggtt taggggttaat ggttttttata    2820
gactaatttt tttagtacat ctatttatt ctattttagc ctctaaatta agaaaactaa    2880
aactctattt tagtttttttt atttaataat ttagatataa aatagaataa cataaagtga    2940
ctaaaaatta aacaaatacc ctttaagaaa ttaaaaaaac taaggaaaca tttttcttgt    3000
ttcgagtaga taatgccagc ctgttaaacg ccgtcgacga gtctaacgga caccaaccag    3060
cgaaccagca gcgtcgcgtc gggccaagcg aagcagacgg cacggcatct ctgtcgctgc    3120
ctctggaccc ctctcgagag ttccgctcca ccgttggact tgctccgctg tcggcatcca    3180
gaaattgcgt ggcggagcgg cagacgtgag ccggcacggc aggcggcctc ctcctcctct    3240
cacggcaccg gcagctacgg gggattcctt tcccaccgct ccttcgcttt ccttcctcg    3300
cccgccgtaa taaatagaca ccccctccac accctctttc cccaacctcg tgttgttcgg    3360
agcgcacaca cacacaacca gatctccccc aaatccaccc gtcggcacct ccgcttcaag    3420
gtacgccgct cgtcctcccc cccccccctc tctaccttct ctagatcggc gttccggtcc    3480
atgcatggtt agggcccggt agttctactt ctgttcatgt ttgtgttaga tccgtgtttg    3540
tgttagatcc gtgctgctag cgttcgtaca cggatgcgac ctgtacgtca gacacgttct    3600
gattgctaac ttgccagtgt ttctctttgg ggaatcctgg gatggctcta gccgttccgc    3660
agacgggatc gatttcatga ttttttttgt ttcgttgcat agggtttggt ttgcccttt    3720
cctttatttc aatatatgcc gtgcacttgt ttgtcgggtc atcttttcat gcttttttt    3780
gtcttggttg tgatgatgtg gtctggttgg gcggtcgttc tagatcggag tagaattctg    3840
tttcaaacta cctggtggat ttattaattt tggatctgta tgtgtgtgcc atacatattc    3900
atagttacga attgaagatg atggatggaa atatcgatct aggataggta tacatgttga    3960
tgcgggtttt actgatgcat atacagagat gcttttttgtt cgcttggttg tgatgatgtg    4020
gtgtggttgg gcggtcgttc attcgttcta gatcggagta gaatactgtt tcaaactacc    4080
tggtgtattt attaattttg gaactgtatg tgtgtgtcat acatcttcat agttacgagt    4140
ttaagatgga tggaaatatc gatctaggat aggtatacat gttgatgtgg gttttactga    4200
tgcatataca tgatggcata tgcagcatct attcatatgc tctaaccttg agtacctatc    4260
tattataata aacaagtatg ttttataatt attttgatct tgatatactt ggatgatggc    4320
atatgcagca gctatatgtg gattttttta gccctgcctt catacgctat ttatttgctt    4380
ggtactgttt cttttgtcga tgctcaccct gttgtttggt gttacttctg caggtcgact    4440
ttaacttagc ctagggaagt tcctattccg aagttcctat tctctagaaa gtataggaac    4500
ttcagatcca ccgggatccc cgatcatgca aaaactcatt aactcagtgc aaaactatgc    4560
ctggggcagc aaaacggcgt tgactgaact ttatggtatg gaaaatccgt ccagccagcc    4620
```

```
gatggccgag ctgtggatgg gcgcacatcc gaaaagcagt tcacgagtgc agaatgccgc    4680
cggagatatc gtttcactgc gtgatgtgat tgagagtgat aaatcgactc tgctcggaga    4740
ggccgttgcc aaacgctttg gcgaactgcc tttcctgttc aaagtattat gcgcagcaca    4800
gccactctcc attcaggttc atccaaacaa acacaattct gaaatcggtt ttgccaaaga    4860
aaatgccgca ggtatcccga tggatgccgc cgagcgtaac tataaagatc ctaaccacaa    4920 gccgagctg gtttttgcgc tgacgccttt ccttgcgatg aacgcgtttc gtgaattttc    4980
cgagattgtc tccctactcc agccggtcgc aggtgcacat ccggcgattg ctcactttt    5040 acaacagcct gatgccgaac gtttaagcga actgttcgcc agcctgttga atatgcaggg    5100
tgaagaaaaa tcccgcgcgc tggcgatttt aaaatcggcc ctcgatagcc agcagggtga    5160
accgtggcaa acgattcgtt taatttctga attttacccg gaagacagcg gtctgttctc    5220
cccgctattg ctgaatgtgg tgaaattgaa ccctggcgaa gcgatgttcc tgttcgctga    5280
aacaccgcac gcttacctgc aaggcgtggc gctggaagtg atggcaaact ccgataacgt    5340
gctgcgtgcg ggtctgacgc ctaaatacat tgatattccg gaactggttg ccaatgtgaa    5400
attcgaagcc aaaccggcta accagttgtt gacccagccg gtgaaacaag gtgcagaact    5460
ggacttcccg attccagtgg atgattttgc cttctcgctg catgaccta gtgataaaga    5520 aaccaccatt agccagcaga gtgccgccat tttgttctgc gtcgaaggcg atgcaacgtt    5580
gtggaaaggt tctcagcagt tacagcttaa accgggtgaa tcagcgttta ttgccgccaa    5640
cgaatcaccg gtgactgtca aaggccacgg ccgtttagcg cgtgtttaca caagctgta    5700 agagcttact gaaaaaatta acatctcttg ctaagctggg ggtggaacct agacttgtcc    5760
atcttctgga ttggccaact taattaatgt atgaaataaa aggatgcaca catagtgaca    5820
tgctaatcac tataatgtgg gcatcaaagt tgtgtgttat gtgtaattac tagttatctg    5880
aataaaagag aaagagatca tccatatttc ttatcctaaa tgaatgtcac gtgtctttat    5940 aattcttga tgaaccagat gcatttcatt aaccaaatcc atatacatat aaatattaat    6000
catatataat taatatcaat tgggttagca aaacaaatct agtctaggtg tgttttgcga    6060 atgcgaccctt cttatgtgct tctagtctcc aaatgtggtt gatagttatt ttgctctaag    6120
atcaacagta atgaagtata atcatcgtt gtggtgtgct actcggttaa ttgagcatta    6180
acacacacaa acatgacgag gatggtataa tctccaaaaa tgtgtacttt gttaggtggg    6240
accctatagc cttgattaat gtgctatgtt aggcatgcct ggaaacgtgt gacgcatatg    6300
ttttgtgaac ctgttgatat tatatgtgct tttatattac catattttat taaaatacta    6360
atatttatta ctagtaagat ataacattct atctagctta aaaactaacc ataaatattc    6420
cataataact agatttacca aactaatata ctaaatatac ataataaata caaaattaac    6480
aagacaataa tcaatattta tgagcttaat atatttagac attatggttg gtcgacgata    6540
atcatgctaa cttttcgtaa ttgcttgatt gaaatatgct tagaataatg cctctttgtt    6600
ctacatggca aatagggacc attatggtgt aacaccctgg gaaccacaaa caccccgaaa    6660
tgctactaaa ctacacaact aaccttcata tataaaattt cgacagcatc tcctttgaaa    6720
atttgcatag acgtggaagc aacagagtat aaacagatat catgataaga aaacatacta    6780
gacattaata atctgctaga aatgggaaga atcctaactt gacgactgcg taactgacta    6840
gagtcacact tagctgaccc tagtcactta caactgactt cgtgtcctag gcttaggcta    6900
ctgctagtcc gcggtgtatc cgtgatcgag ttggcgccag acggaatctg ttctccatcg    6960
ctgacatcct cgagtagatc acattcaagc ttgatatcga attcctgcag cccatccctc    7020
```

| | |
|---|---|
| agccgccttt cactatcttt tttgcccgag tcattgtcat gtgaaccttg gcatgtataa | 7080 |
| tcggtgaatt gcgtcgattt tcctcttata ggtgggccaa tgaatccgtg tgatcgcgtc | 7140 |
| tgattggcta gagatatgtt tcttccttgt tggatgtatt ttcatacata atcatatgca | 7200 |
| tacaaatatt tcattacact ttatagaaat ggtcagtaat aaaccctatc actatgtctg | 7260 |
| gtgtttcatt ttatttgctt ttaaacgaaa attgacttcc tgattcaata tttaaggatc | 7320 |
| gtcaacggtg tgcagttact aaattctggt ttgtaggaac tatagtaaac tattcaagtc | 7380 |
| ttcacttatt gtgcactcac ctctcgccac atcaccacag atgttattca cgtcttaaat | 7440 |
| ttgaactaca catcatattg acacaatatt ttttttaaat aagcgattaa aacctagcct | 7500 |
| ctatgtcaac aatggtgtac ataaccagcg aagtttaggg agtaaaaaac atcgccttac | 7560 |
| acaaagttcg ctttaaaaaa taagagtaa attttacttt ggaccaccct tcaaccaatg | 7620 |
| tttcacttta gaacgagtaa ttttattatt gtcactttgg accaccctca aatcttttt | 7680 |
| ccatctacat ccaatttatc atgtcaaaga aatggtctac atacagctaa ggagatttat | 7740 |
| cgacgaatag tagctagcat actcgaggtc attcatatgc ttgagaagag agtcgggata | 7800 |
| gtccaaaata aaacaaaggt aagattacct ggtcaaaagt gaaacatca gttaaaaggt | 7860 |
| ggtataaagt aaaatatcgg taataaaagg tggcccaaag tgaaatttac tcttttctac | 7920 |
| tattataaaa attgaggatg ttttgtcgg tactttgata cgtcattttt gtatgaattg | 7980 |
| gttttaagt ttattcgctt ttggaaatgc atatctgtat ttgagtcggg ttttaagttc | 8040 |
| gtttgctttt gtaaatacag agggatttgt ataagaaata tctttaaaaa aacccatatg | 8100 |
| ctaatttgac ataattttg agaaaaatat atattcaggc gaattctcac aatgaacaat | 8160 |
| aataagatta aaatagcttt cccccgttgc agcgcatggg tatttttct agtaaaaata | 8220 |
| aaagataaac ttagactcaa aacatttaca aaaacaaccc ctaaagttcc taaagcccaa | 8280 |
| agtgctatcc acgatccata gcaagccag cccaacccaa cccaacccaa cccaccccag | 8340 |
| tccagccaac tggacaatag tctccacacc cccccactat caccgtgagt tgtccgcacg | 8400 |
| caccgcacgt ctcgcagcca aaaaaaaaaa aagaaagaaa aaaaagaaaa agaaaaaaca | 8460 |
| gcaggtgggt ccgggtcgtg ggggccggaa acgcgaggag gatcgcgagc cagcgacgag | 8520 |
| gccggccctc cctccgcttc caaagaaacg ccccccatcg ccactatata catacccccc | 8580 |
| cctctcctcc catccccca accctaccac caccaccacc accacctcca cctcctcccc | 8640 |
| cctcgctgcc ggacgacgag ctcctccccc ctcccctcc gccgccgccg cgccggtaac | 8700 |
| cacccccgcc ctctcctctt tctttctccg ttttttttt ccgtcacggt ctcgatcttt | 8760 |
| ggccttggta gtttgggtgg gcgagaggcg gcttcgtgcg cgcccagatc ggtgcgcggg | 8820 |
| aggggcggga tctcgcggct ggggctctcg ccggcgtgga tcaggccgg atctcgcggg | 8880 |
| gaatggggct ctcggatgta gatctgcgat ccgccgttgt tggggagat gatgggggt | 8940 |
| ttaaaatttc cgccatgcta aacaagatca ggaagagggg aaaagggcac tatgtttat | 9000 |
| atttttatat atttctgctg cttcgtcagg cttagatgtg ctagatcttt cttctcttctt | 9060 |
| tttgtgggta gaatttgaat ccctcagcat tgttcatcgg tagtttttct tttcatgatt | 9120 |
| tgtgacaaat gcagcctcgt gcggagcttt tttgtaggta gaaggatcca cacgacacca | 9180 |
| tgtcccccga gcgccgcccc gtcgagatcc gcccggccac cgccgccgac atggccgccg | 9240 |
| tgtgcgacat cgtgaaccac tacatcgaga cctccaccgt gaacttccgc accgagccgc | 9300 |
| agaccccgca ggagtggatc gacgacctgg agcgcctcca ggaccgctac ccgtggctcg | 9360 |

```
tggccgaggt ggagggcgtg gtggccggca tcgcctacgc cggcccgtgg aaggcccgca    9420
acgcctacga ctggaccgtg gagtccaccg tgtacgtgtc ccaccgccac cagcgcctcg    9480
gcctcggctc caccctctac acccacctcc tcaagagcat ggaggcccag ggcttcaagt    9540
ccgtggtggc cgtgatcggc ctcccgaacg accgtccgt gcgcctccac gaggccctcg     9600
gctacaccgc ccgcggcacc ctgcgcgccg ccggctacaa gcacggcggc tggcacgacg    9660
tcggcttctg gcagcgcgac ttcgagctgc cggccccgcc gcgcccggtg cgcccggtga    9720
cgcagatctg agtcgacctg caggcatgcc gctgaaatca ccagtctctc tctacaaatc    9780
tatctctctc tataataatg tgtgagtagt tcccagataa gggaattagg gttcttatag    9840
ggtttcgctc atgtgttgag catataagaa acccttagta tgtatttgta tttgtaaaat    9900
acttctatca ataaaatttc taattcctaa aaccaaaatc cagtggcgag ctaatgcggc    9960
ccgaataact tcgtatagca tacattatac gaagttatac ctggtggcgc cgctaggggc    10020
tgcaggaatt cctgcagccc gggggatcca ctagttctag agcggccgac ctcgacagat    10080
ctaagcttac tagtgccgtg ggtcgtttaa gctgccgctg tacctgtgtc gtctggtgcc    10140
ttctggtgta cctgggaggt tgtcgtctat caagtatctg tggttggtgt catgagtcag    10200
tgagtcccaa tactgttcgt gtcctgtgtg cattataccc aaaactgtta tgggcaaatc    10260
atgaataagc ttgatgttcg aacttaaaag tctctgctca atatggtatt atggttgttt    10320
ttgttcgtct cctaatattt gcctgggatc aaatttatt ggctggtgtt catttgacct     10380
ccatgttctt gctaggctcc attttttact ctacagccat aatatgtttg attgtttggt    10440
ttgttctttg ttgtacacct ggttctgtcg agcttagttt tcgacactgg cttacagctt    10500
aacatgttgc tattttattg ggttctgatt gctattttat tgggttctga ttgctagttt    10560
ttgctgaatc caaaaaccat gttatttatt taagcgatcc aggttattat tatgatggtg    10620
gctaagtttt tttttttcca agggtaaatt ttctggattc tccagtgttt ctgtggccga    10680
attcactagt gattcagatc tgatatcgat gggcccacta actatctata ctgtaataat    10740
gttgtatagc cgccggatag ctagctagtt tagtcattca gcggcgatgg gtaataataa    10800
agtgtcatcc atccatcacc atgggtggca acgtgagcaa tgacctgatt gaacaaattg    10860
aaatgaaaag aagaaatatg ttatatgtca acgagatttc ctcataatgc cactgacgac    10920
gtgtgtccaa gaaatgtatc agtgatacgt atattcacaa ttttttttatg acttatactc    10980 acaatttgtt tttttactac ttatactcac aatttgttgt gggtaccata acaatttcga    11040
tcgaatatat atcagaaagt tgacgaaagt aagctcactc aaaaagttaa atgggctgcg    11100
gaagctgcgt caggcccaag ttttggctat tctatccggt atccacgatt ttgatggctg    11160
agggacatat gttcgcttaa gcttggtcac ccggtccggg cctagaaggc cagcttcaag    11220
tttgtacaaa aaagcaggct ccggccagaa tctcactgac tagctaaaca gcggccgctt    11280
ttaagtatga ccaatttta agtataaacc cctcacgatt ggttattttt ttaagtataa     11340 ccaatttta agtataaacc cctcaccaat ttttaagtat aaacctagcg actaataaac     11400
acaacttctt gccaaagtgt gagcatcacc attggatctg cgcccctcac gaacagtctt    11460
cgccggggta aaattctcca aattaaagtc atcttgatgt ccttgatcac ctgtccataa    11520
ggcccaatcc cagctccacg tatacttctg ataagattga catagtcact tgcatgccag    11580
tgtggaactc tggatgccta ggtcagaggc tagtgactgg ccttcccggc atgctagcat    11640
gtagcatgcc aaggatctgg ctgctccagg tttgttatgc ctgacatcac catagggatg    11700
agagcaagta taataatagg ctgtaagctt taaatgctca ggtggagaaa aaaggagag    11760
```

```
gagaggagag agaaaagtgg gctataagct tatagctgtg ttagacataa gaatcagaaa    11820
cttcgtatga gagacaggtg agctatatat taataacaaa gagctaacta ttatatgagt    11880
gaaccgagag aaggctgtaa aaaaacttac acaatcaacg atcgacatta ttattaacct    11940
tgctctgtct tgcgagacct cttttgacaaa gctacatcaa tgccggccaa gtgccttggg    12000
atttgggaat ggcttctttc ctcccttcct cggttgtccc ccaaggccta ggcttgccac    12060
gctgtattca gtcgcagccg cctttacttt tgccctttgt ggaagttttg taataaatgg    12120
tctgattcta tcttcggata gatgaagccg gatgtttcat ccattatcta aaaaaaagtt    12180
ggttgctttg ctgagctaag aaagtgtaat ccagagtgcc cgtaacgtat tcatgtacat    12240
aactattatc taatataaat cttcttttgt cgcaaaaaaa ggtcggccca tcagaacaaa    12300
tgatcaatgt aaggcccaaa atttgtgtct caaatgtcat ttacgtttcc aagctaaaca    12360
aaaacacagg attcatataa ttttgctggt ggcttaggct tcgtccaata gtgcttagtt    12420
taatttgtat atacctgcac catggtattc gtctggcctt ggatcttgcg catcaattgc    12480
ctatggacga tgatcgcagc cacgccacat tcattttaa tcgccatttg cttgacaccc    12540
aatgcctctg caccacttgc gcacgctacg caccgtctga tacgccaaga tcccgagcta    12600
aaataacacc caatcatcag atgaaaacaa gcgcgagtgc gagccagccc atggcagcga    12660
tcttggccat ttgcggagcc aactgaaagc cgtgcacaaa atattcgaca ccgtataagg    12720
gaaaacacta gttatacgag gtgggcaata atccagatct cggactcttc ctaacccggt    12780
tcacatgcat agcatatatg atggccggcc ggggttcaca tgaacgccat cccgtgccct    12840
agtgcactga tttcttaatt tcgaattta agtatgacca atttttaagt ataaacccct    12900
cacgattggt tatttttta agtataacca atttttaagt ataaacccct caccaatttt    12960
taagtataaa cctagcgact aataaacaca acttcttgcc aaagtgtgag catcaccatt    13020
ggatctgcgc ccctcacgaa cagtcttcgc cggggtaaaa ttctccaaat taaagtcatc    13080
ttgatgtcct tgatcacctg tccataaggc ccaatcccag ctccacgtat acttctgata    13140
agattgacat agtcacttgc atgccagtgt ggaactctgg atgcctaggt cagaggctag    13200
tgactggcct tcccggcatg ctagcatgta gcatgccaag gatctggctg ctccaggttt    13260
gttatgcctg acatcaccat agggatgaga gcaagtataa taataggctg taagctttaa    13320
atgctcaggt ggagaaaaaa aggagaggag aggagagaga aaagtgggct ataagcttat    13380
agctgtgtta gacataagaa tcagaaactt cgtatgagag acaggtgagc tatatattaa    13440
taacaaagag ctaactatta tatgagtgaa ccgagagaag ctgtaaaaa aacttacaca    13500 atcaacgatc gacattatta ttaaccttgc tctgtcttgc gagacctctt tgacaaagct    13560
acatcaatgc cggccaagtg ccttgggatt tgggaatggc ttctttcctc ccttcctcgg    13620
ttgtccccca aggcctaggc ttgccacgct gtattcagtc gcagccgcct ttacttttgc    13680
cctttgtgga agttttgtaa taaatggtct gattctatct tcggatagat gaagccggat    13740
gtttcatcca ttatctaaaa aaagttggt tgctttgctg agctaagaaa gtgtaatcca    13800
gagtgcccgt aacgtattca tgtacataac tattatctaa tataaatctt cttttgtcgc    13860
aaaaaaaggt cggcccatca gaacaaatga tcaatgtaag gcccaaaatt tgtgtctcaa    13920
atgtcattta cgtttccaag ctaaacaaaa acacaggatt catataattt gctggtggc    13980 ttaggcttcg tccaatagtg cttagtttaa tttgtatata cctgcaccat ggtattcgtc    14040
tggccttgga tcttgcgcat caattgccta tggacgatga tcgcagccac gccacattca    14100
```

```
tttttaatcg ccatttgctt gacacccaat gcctctgcac cacttgcgca cgctacgcac    14160
cgtctgatac gccaagatcc cgagctaaaa taacacccaa tcatcagatg aaaacaagcg    14220
cgagtgcgag ccagcccatg gcagcgatct tggccatttg cggagccaac tgaaagccgt    14280
gcacaaaata ttcgacaccg tataagggaa aacactagtt atacgaggtg ggcaataatc    14340
cagatctcgg actcttccta acccggttca catgcatagc atatatgatg gccggccggg    14400
gttcacatga acgccatccc gtgccctagt gcactgattt cttaatgtcg acgggccgct    14460
tttaagtatg accaattttt aagtataaac ccctcacgat tggttatttt tttaagtata    14520
accaattttt aagtataaac ccctcaccaa tttttaagta taaacctagc gactaataaa    14580
cacaacttct tgccaaagtg tgagcatcac cattggatct gcgcccctca cgaacagtct    14640 tcgccgggt aaaattctcc aaattaaagt catcttgatg tccttgatca cctgtccata    14700
aggcccaatc ccagctccac gtatacttct gataagattg acatagtcac ttgcatgcca    14760
gtgtggaact ctggatgcct aggtcagagg ctagtgactg gccttcccgg catgctagca    14820
tgtagcatgc caaggatctg gctgctccag gtttgttatg cctgacatca ccatagggat    14880
gagagcaagt ataataatag gctgtaagct ttaaatgctc aggtggagaa aaaaaggaga    14940
ggagaggaga gagaaaagtg ggctataagc ttatagctgt gttagacata agaatcagaa    15000
acttcgtatg agagacaggt gagctatata ttaataacaa agagctaact attatatgag    15060
tgaaccgaga gaaggctgta aaaaaactta cacaatcaac gatcgacatt attattaacc    15120
ttgctctgtc ttgcgagacc tctttgacaa agctacatca atgccggcca agtgccttgg    15180
gatttgggaa tggcttcttt cctcccttcc tcggttgtcc cccaaggcct aggcttgcca    15240
cgctgtattc agtcgcagcc gcctttactt ttgcccttg tggaagtttt gtaataaatg    15300
gtctgattct atcttcggat agatgaagcc ggatgtttca tccattatct aaaaaaaagt    15360 tggttgctt gctgagctaa gaaagtgtaa tccagagtgt tcgtaacgta ttcatgtaca    15420
taactattat ctaatataaa tcttcttttg tcgcaaaaaa aggtcggccc atcagaacaa    15480
atgatcaatg taaggcccaa aatttgtgtc tcaaatgtca tttacgtttc caagctaaac    15540
aaaaacacag gattcatata attttgctgg tggcttaggc ttcgtccaat agtgcttagt    15600
ttaatttgta tatacctgca ccatggtatt cgtctggcct tggatcttgc gcatcaattg    15660
cctatggacg atgatcgcag ccacgccaca ttcattttta atcgccattt gcttgacacc    15720
caatgcctct gcaccacttg cgcacgctac gcaccgtctg atacgccaag atcccgagct    15780
aaaataacac ccaatcatca gatgaaaaca agcgcgagtg cgagccagcc catggcagcg    15840
atcttggcca tttgcggagc caactgaaag ccgtgcacaa aatattcgac accgtataag    15900
ggaaaacact agttatacga ggtgggcaat aatccagatc tcggactctt cctaacccgg    15960
ttcacatgca tagcatatat gatggccggc cggggttcac atgaacgcca tcccgtgccc    16020
tagtgcactg atttcttaat cccatccagc atgctcttca attttggtgc tcacccttac    16080
gggtatgccc tcactgcctt ttataattgt ataagggaaa tattattcaa tataatgtcc    16140
taaaaattgg caatatcaat ctaaaaatcg ttatgaatag gatgtaaaca aagctactat    16200
ctgtccatat ataacgtcac aggaaggaca aaaaattcag tcagcgatcg agaacggcaa    16260
agaaaaacca tattattgtt gcttgccgac ataaatttaa gtataggaca aaaaaaaaag    16320
ccacatcata ttcatactga tgggcttacc agacaaaatg aaataaacgt gtgcatgcat    16380
gcatgcatgt tacgaacgtc tggatagagt ctccgagctg agtgtggtcc gacgtggaag    16440
tgtacgtctc aacacacgac gcatgtgacc gacaagggca agttgaagtc tatgcatgga    16500
```

```
tgggcctgag cgccgcgctg aatgaatctg gacgggtggt agggcatctc ggtgggcaaa    16560
acaaataact ccgtgtgctg catggctgcc tttggaatct ttgcatgcag ctgtgtgctg    16620
aactgaaacc cttcgctcta tctatataaa cagatgccct tcgctctcgt ctcagcaggc    16680
agcatcgtct caagttttgt tctcctctcc tagctagcca gcacctgcag atctgctcgt    16740
tgccttggta attcatcatg tagtacgtag catcagctag tatttatctc aagtatatat    16800
atacgcatat gtgtcgtcgc agtactttcc cttatctctc tatacacact acacgcatac    16860
ataccaatac catccgtctt aactcttaat ctttgcctgc atacgtacac tgcacgtacg    16920
tactgcaggg ctactgattt tgtggaacga agcggtcgag accggtgatc ttgtaaggtt    16980
cccttccctc ctcccctcac acccctgttc gtgttccttc ggatcggatc tcagtggtga    17040
tgttagacgt ccgcggctgc ctacgtagtg gcattgccgc ccgaaaggtt tgtttaggtg    17100
gggtagatcc gaaacaggcc ggatctggac catgtccgcg gcggggcggc gggacttgat    17160
cgcgtagctg tcgtgtgcat ttctccctac cagtggcgga atcggcgatg tggacctaag    17220
ggctaaggct tatctgctgc cttgaccatt tcgtcgctga caaaaacaaa gtgacaatca    17280
tgccgttctc tgtttgttta tctggatcgt tattacgctg tgaatcctgc gatatgtggc    17340
taagtgattt ttcttctttt tctggggca gtttagcctt tgacccagtc ctaggtgtgg    17400
tcactaggac tgtgtagcat gatgagtgag gttgcagcag gctgattgct agtgacgtt     17460 ttttccccca atttgttagg ttttcacgct ccaggttgtg caagtaattt tgctagtgat    17520
tgtgtgatcc atcttcaacg ttgaaccttg ttttccccc taaaaccccc aacaggaaat     17580 cttgcccga cttctattgc aaaaattgta acgcttagca ccctgattga ctcaattcct     17640
gtcactaggc atgctcggtc aaaagcagat gatttaccac ttagaaactg ccctgcccct    17700
gctttccaca tagcatttcg aacttttga ctactattga cacccccta acttgccgaa      17760 ctatttctct cttcagctac tatttaccta gttataatta cataaatgtt tgtgtgtatc    17820
ttgtgcaggg atccgccatg gcagagccga acaagggtgg agcacctgcg atgaagaacg    17880
tcgccaagcc gtcgaccaaa cgcctgatcc cgagctcgat agccgcttcg agccagacta    17940
gcgccaacgc tctgacggag cccttcctg ggtctgacgc gatcggccag agctacgacg      18000
cattcgggtt cttcgccaat ccccgcagca tcatgaagga gctgttcgag ttcagcccac    18060
aggaggagat cgtcgtcgaa ggcaacacct ggcttctcag cagcgacttc gtctacaccg    18120
ccatccgcga cacagagacc tcgaccgtct cgaggcgcac caaggacgac tacagcaagg    18180
agctggccgt gaaggtgaag ctcagcggaa gctacggcta cttcagcgct agcgtggaga    18240
gcgacttcag ccagagcatc agcgacgcta ccgacacgac gtacaccagc gtccgcaccc    18300
acgtcaacaa gtggcgcctc agcctcaagg acgacgtcgg agctctccgg agcaagctcc    18360
ttcctggtgt caagcaggct ctcgctacga tggacgcaac ccagctcttc gacacgttcg    18420
gcacccacta cgtcagcgag gtcctcgtcg gtggaagagc cgactacgtc gccaccacca    18480
agaccagcgc cttcagctcg agcacctcca tcagcgtcgc tgcagaggcg tcgtttcaga    18540
gcatcgcagg aggcgaagtc agccccgaga gcaaggtcct cgccgagatg ctgcgcgaga    18600
actccagcac acggctctac gcactgggag gctcagcact cccgaacatc acggaccag     18660 cgacctacaa cgcctggctg gagagcatcg acaccatccc ggtcttctgc ggcttcaccc    18720
agaactccct caagtcgatc agcgagctcg cggattcagc ccaacgcaga gacgcactcg    18780
cgaaggcatc ccagtcgtac atccccagct acgtcactcg cccagcagtc gtgggcctcg    18840
```

```
aggtcatcat ctccgactcc aactccgaga gccctccata cggctacacc cggatcgact    18900
acgacctcaa ccgcaatgcc ggaggcaagt acgtcttcct ctgctacaag cagaagaaca    18960
tctccgtcgg aggtgacgca gacgcgatca cggacgtcct cgtcgtctac ggcaacgacc    19020
ggaacccaag cgtgccctca ggctacacca agatcgacaa ggacctgaac tccggagctg    19080
gagggaagta catctacttc tgctactcca aggacaagcg caagcaggag gagggccttc    19140
cgatacgcgg acttcgcgtc gttggaccac accctacgtc agtggcaccg tacggcttca    19200
gcaagatcga catcgacctc aacatgggcg caggtgggga cttcatctac ctctgcaagt    19260
cgcggcacct cgagtgagtt aaccccgggt caacccatca ggaaggatga agcgcccctc    19320
attttgtgcc ctaggtcgtg gattgctgga ttttaatttt acacatttcc ttgtcgatcc    19380
tttctgctgt gtgtggttcg agaatgttag tgtgttatcg caagatctgg gtgtttggaa    19440
gttatctcat tattgggcct cataaattca taattcttgc cagttagtga caactgtagc    19500
ttaggtttac ttctgcttgt agtacatcgc ctagatcgtg ggagtccctc ttttcagacg    19560
aatgtcatga acattggtt tttggaaatg attaggaaga catttgctgt tttgtcgact     19620 gctgttttt acggccaagt tcagagtttt ttttttcatg tacaaagtat cagcagttaa     19680
attatgttac ctttaccatg gttcttcata tttgttttcc ttccattgct caatctatgt    19740
catcttttga aatggtttgg aaggcatcct ttataggata tatagatata gatttgaagc    19800
ataattgtta ggataagaca ccagctagcc tatgctgcaa cgcacattat tcgaccctta    19860
ataacaacag gtgatttta tattataaaa aagttggaaa agtatacaca agaattttc     19920 aaaagaaggg taaagggaa cagccctcct gctcgacaat tggaattggt gtcccgcata     19980
atttttttct gcctttgaga attcaggcgt ctctggattc tagttcacca tttaccaatt    20040
agaaggaata ctatgtatgt ataattctac aatctgcatt ctacacaatc cttctatttt    20100
ctgaatatag ttgcaagact agggctctct tatagtattt ctaattatag ccgctttgca    20160
aagtactgtc atatttgatt aggggtattg gaaagaagga gaaagggtg acaccctgct     20220 tgacaattgg aattgataag cagccagggt accaaggcgc gaaacagccc cctccggcgg    20280
tgtcccccac tgaagaaact atgtgctgta gtatagccgc tggctagcta gctagttgag    20340
tcatttagcg gcgatgattg agtaataatg tgtcacgcat caccatgcat gggtggcagt    20400
ctcagtgtga gcaatgacct gaatgaacaa ttgaaatgaa aagaaaaaag tattgttcca    20460
aattaaacgt tttaaccttt taataggttt atacaataat tgatatatgt tttctgtata    20520
tgtctaattt gttatcatcc atttagatat agacgaaaaa aaatctaaga actaaaacaa    20580
atgctaattt gaaatgaagg gagtatatat tgggataatg tcgatgagat ccctcgtaat    20640
atcaccgaca tcacacgtgt ccagttaatg tatcagtgat acgtgtattc acatttgttg    20700
cgcgtaggcg tacccaacaa ttttgatcga ctatcagaaa gtcaacggaa gcgctgcaga    20760
aacttatctc tgttatgaat cagaagaagt tcatgtctcg tttcatttaa aactttggtg    20820
gtttgtgttt tggggccttg taaagcccct gatgaataat tgttcaacta tgtttccgtt    20880
cctgtgttat acctttcttt ctaatgagta atgacatcaa acttcttctg tattgaaatt    20940
atgtccttgt gagtctcttt atcatcgttt cgtctttaca ttatatgtgc tacttttgtc    21000
taatgagcct gaaaagtggc tccaatggta cgcactggaa gatttgttgg cttctggtag    21060
atatagcgac agtgttgagc ttgtaatatc atgtctctta ttgctaaatt agttcctttc    21120
ttaacagaaa ccttcaaagt ttttgttttt gttttcattt acctaatgta cacatacgct    21180
ggccatgact aacaacatgt ccaggcttag agcatatttt tttctagctt aaattgttaa    21240
```

```
cttgtcattc agtaaaatcc gagaattgtg aagctctaat tgaagctaat tcgtttata    21300 aagtcagtta aaaagtatac taaattatcc aactttcctt caaaatctca aaattctatg    21360
acaaaacgat agtctttgtt tatgtcagta ccacaaagag gtggaaaaaa acaccaaaaa    21420
aacaataagc aaactataca ctgagaagaa aaataaaaga gagctcaata gatgttttat    21480
actaacggta gattagatca aagatccaag ctttactcta catagagcag aacccagaat    21540
cccttcatat ctcttttatt ctagcaccga taatctactg aaaagaagac acttagagct    21600
ctgtctcttt gtcaaagaag tcccagccgt catccagaag ctccttacgt tcattaacag    21660
agaattcgac aaagcagcat tagtccgttg atcggtggaa gaccactcgt cagtgttgag    21720
ttgaatgttt gatcaataaa atacggcaat gctgtaaggg ttgttttta tgccattgat    21780 aatacactgt actgttcagt tgttgaactc tattcttag ccatgccaag tgcttttctt    21840
attttgaata acattacagc aaaagttga aagacaaaaa aaaaaccccc gaacagagt    21900 gctttgggtc ccaagcttct ttagactgtg ttcggcgttc cccctaaatt tctcccccta    21960
tatctcactc acttgtcaca tcagcgttct cttcccct atatctccac gctctacagc    22020
agttccacct atatcaaacc tctataccc accacaacaa tattatatac tttcatcttc    22080
aactaactca tgtaccttcc aattttttc tactaataat tatttacgtg cacagaaact    22140
tagcaaggag agagagagcg gggtgaccaa gcttggcgcg ccattctatc actagctagc    22200
tgctaattat tcccgggcac ccagctttct tgtacaaagt ggccgttaca gaatcactga    22260
ctagctaatc tagcggccgc tcaagcttcg gcatgcaatt cgcataccta cagtacaacg    22320
tggccaaagt catcatttaa tgagctctcg ggcgcgccgt ctcactagct agctgctaac    22380
gttcccgggc aactttatta tacaaagttg atagatccta caggccagaa tggcctctgg    22440
attcagcggc ctagaaggcc gaagtacttg gtcttcctaa tatcggaccg aggaccgatt    22500 aaacttaat tcggtccgtc aatattcacc gaagcgacta attaactagc tgtcccacgg    22560
cctaactagc acttaatccc ctagcctaac ctaagagcgc taatctaggc tagtggtcac    22620
ttagggcttt aaggctagcg tatacgaagt tcctattccg aagttcctat tcttcaaaaa    22680
gtataggaac ttctgtacac ctgagctgat tccgatgact tcgtaggttc ctagctcaag    22740
ccgctcgtgt ccaagcgtca cttacgatta gctaatgatt acggcatcta ggaccgacta    22800
gctaactaac tagggcgcgc catgaggagc aatcattgtt caagacatga tgcaaagcta    22860 gaaactttg attgtggccg tcctaattgt gaagtttagg ccggggggaa cttcatgaac    22920
cctatcgaag cttaattagt tcttttttgt tgttagccat gtttgtattg tagtttaggt    22980
gaacaacatg acgccgcacc cgcgatctca gggctcgtcc ccacacagga gggcacgtcg    23040
tcgtcttcgc cgccgagcat cagagattca gagcacgtac acgcacatct caagcaaacg    23100
gagtagtacg tcctactcct acgtacatac ctagccgacg acctttatgt gcacaccacc    23160
actgctctgc tgcccggcct ctccgtcgtc cgttcatcac cagctggtct ggtccttcaa    23220
tttccatgcg tcggtccgaa gtcaacattt tccgtcaatt catggccaaa ggctacaact    23280
aacattgttt aatgtcgact gttttttttt tgttaatgtg acgccgtgtt ttttttgtta    23340
ttgctagaac actgtttaat gtcaaactgt tttaagtcca tgggacgcct cagcaatagt    23400
agccttttgt taatgtgacg ccgcatcaat caactaatta aagcccttaa ccatctgtgt    23460
ctcattgtta ccggcatcac ctaaacaaca gatcacggct ctacgagcaa cgtacataac    23520
agtaaactaa tggcctgatc tgctgggcta gtagggccac agcaacacta gctgaacgta    23580
```

-continued

```
tgcagcggcg gcggcggcac catccaagta actcaagcga gcacggttga acaatacttg    23640
aacctttttg tcccaatcca ctttagaaaa ctaagaaatt catatcggag aaaggtcgaa    23700
gaatggtttg agaaaagact cggtagcttc cccaccaagt ctcacaatag aaacattatg    23760
aaaatattta cccttcataa ccctaatatg acccttcttc gcagtcgact tctcaaagac    23820
gacgtggctt ggtttctagg gtcgttcttc ggcatcaccc tcaaaatcaa agtcctcgct    23880
atcctcagaa tcgttgacat tccgaccaat attttataag taatcttcgg aatattactc    23940
ttctccatag cctcctggaa cccagcaagc gcaaactctt cactcttgct cccctcgacc    24000
atcatagcca aaaccaaata accaatgaat ctaaaacggt cacaattgat aataataacc    24060
ttcggtttta aagcgctagc tattctagca acaaaatagg tgaatggtgt gataattgcg    24120
catacgattt tcattctatt tataataaaa gccaggccag ggtcgaataa aaatataaa    24180 actaccactg caaaatgggc ctcgcatttc aagtatctcg atgattagct taaggaaggt    24240 gtttttcaa ccttcgacat aaggccttcg ttcatttctc agtttgagtt cgttgcaaga    24300
aaacaaacta atactgggag gggctagttt tggggccttc atcatttgaa ggttctcaaa    24360
acactaatta accattgttt catgatacat ctctaaaagt gttacaggtg cttcagtaaa    24420
aaccaccttc gaaataaatc gagcaacgac gaaggtacat tctactagc ggataaaact    24480 ggtcttgggc cgaggcagca tacaaagaag cttcgcctgt gcgcgcaagt ggcagaggtg    24540
ttagccgaag tcgataactt tggcaacaac agaagaggat ggagaaaata cattattatc    24600
ctgatggtat ttgtaaacaa tgtttgtaaa accttggggc atgattataa ttctatataa    24660
agacagttca ttttcctata aataggtgag cagtaccctg cataaggcat cttttttgagg   24720 ggtgatcact tcgtttaact tagcttacag agaacctttg taccatcttg tgtgtggagc    24780
tgaaggtatg cttgtacacc tttatcaaga gagatagagt aaattgctaa ggcatataag    24840
atgagttgaa tatgaagtta cactttg                                        24867
```

```
<210> SEQ ID NO 4
<211> LENGTH: 1434
<212> TYPE: DNA
<213> ORGANISM: Ophioglossum pendulum

<400> SEQUENCE: 4
```

```
atggaaccca acaaggtgg tgctccagcc atgaaaaatg tagccaaacc ttccacaaag      60
agactcatac cgtcatccat tgctgcatca tcgcaaacat ctgcaaatgc attaaccgag    120
ccattgcctg gctctgatgc catcggccag agctacgatg cattcgggtt cttcgccaat    180
cccagaagca tcatgaagga gttgttcgag ttcagtcctc aagaggagat agtcgtggaa    240
ggaaatacct ggcttctctc ttcggacttc gtttacaccg caattagaga cactgagacc    300
tccacggtct cacgtcgcac caaggacgac tactccaagg aattggctgt gaaggtgaag    360
ctgtctggaa gctatggcta ttttttctgcc tccgttgagt ctgatttctc tcagagcatt    420
tccgatgcga cggacaccac atacacttca gttcgcaccc acgtcaacaa gtggaggctg    480
agcctgaagg acgatgttgg ggcccttcgc tcgaagctgc tgcctggcgt caagcaggcg    540
ctggctacca tggatgctac gcagctcttt gacacgttcg ggactcacta tgtgagcgag    600
gtgcttgtgg gtgggcgtgc agactacgtt gccaccacca agaccagcgc gttcagctca    660
tccaccagca tcagcgtagc ggcagaagca tcattccagt ccatcgcggg tggggaggtg    720
tctccggagt ccaaggtgct tgcggagatg ctgagagaga acagcagcac acgcctgtac    780
gctcttggcg ggagtgccct ccccaacatc acagatccag ccacgtacaa cgcctggctg    840
```

-continued

```
gagtccattg acaccatccc tgtcttctgc ggattcactc aaaacagcct caagtccatc    900
tcggagcttg ctgactccgc tcaacgccgg gacgctctgg ccaaagcctc ccaaagctat    960
atcccatcat acgtgactcg tcctgcagtg gttggcttgg aggtcataat atcggacagc   1020
aactcggaga gccctcccta tggctacacc agaatagact acgacctcaa ccgcaacgca   1080
ggaggcaaat acgtgttcct ctgctacaag cagaagaaca tttcagtggg aggggatgcc   1140
gatgccatca ccgacgtcct tgtcgtctac ggaaatgacc gaaatccatc tgtgccgtct   1200
ggctacacca agatcgacaa ggacctcaac tccggggcag gcggtaagta tatctacttc   1260
tgctactcca aggacaagcg gaagcaagag gagggactgc ccattcgtgg gcttcgtgtt   1320
gttgggcctc acccaacctc agtggcacct tacggattct ctaagatcga catagatctg   1380
aatatgggtg caggaggaga tttatatac ctttgcaaat cacgccattt ggag           1434
```

<210> SEQ ID NO 5
<211> LENGTH: 478
<212> TYPE: PRT
<213> ORGANISM: Ophioglossum pendulum

<400> SEQUENCE: 5

```
Met Glu Pro Asn Lys Gly Gly Ala Pro Ala Met Lys Asn Val Ala Lys
1               5                   10                  15

Pro Ser Thr Lys Arg Leu Ile Pro Ser Ser Ile Ala Ala Ser Ser Gln
            20                  25                  30

Thr Ser Ala Asn Ala Leu Thr Glu Pro Leu Pro Gly Ser Asp Ala Ile
        35                  40                  45

Gly Gln Ser Tyr Asp Ala Phe Gly Phe Phe Ala Asn Pro Arg Ser Ile
    50                  55                  60

Met Lys Glu Leu Phe Glu Phe Ser Pro Gln Glu Ile Val Val Glu
65                  70                  75                  80

Gly Asn Thr Trp Leu Leu Ser Ser Asp Phe Val Tyr Thr Ala Ile Arg
                85                  90                  95

Asp Thr Glu Thr Ser Thr Val Ser Arg Arg Thr Lys Asp Asp Tyr Ser
            100                 105                 110

Lys Glu Leu Ala Val Lys Val Lys Leu Ser Gly Ser Tyr Gly Tyr Phe
        115                 120                 125

Ser Ala Ser Val Glu Ser Asp Phe Ser Gln Ser Ile Ser Asp Ala Thr
    130                 135                 140

Asp Thr Thr Tyr Thr Ser Val Arg Thr His Val Asn Lys Trp Arg Leu
145                 150                 155                 160

Ser Leu Lys Asp Asp Val Gly Ala Leu Arg Ser Lys Leu Leu Pro Gly
                165                 170                 175

Val Lys Gln Ala Leu Ala Thr Met Asp Ala Thr Gln Leu Phe Asp Thr
            180                 185                 190

Phe Gly Thr His Tyr Val Ser Glu Val Leu Val Gly Gly Arg Ala Asp
        195                 200                 205

Tyr Val Ala Thr Thr Lys Thr Ser Ala Phe Ser Ser Thr Ser Ile
    210                 215                 220

Ser Val Ala Ala Glu Ala Ser Phe Gln Ser Ile Ala Gly Gly Glu Val
225                 230                 235                 240

Ser Pro Glu Ser Lys Val Leu Ala Glu Met Leu Arg Glu Asn Ser Ser
                245                 250                 255

Thr Arg Leu Tyr Ala Leu Gly Gly Ser Ala Leu Pro Asn Ile Thr Asp
            260                 265                 270
```

```
Pro Ala Thr Tyr Asn Ala Trp Leu Glu Ser Ile Asp Thr Ile Pro Val
        275                 280                 285

Phe Cys Gly Phe Thr Gln Asn Ser Leu Lys Ser Ile Ser Glu Leu Ala
    290                 295                 300

Asp Ser Ala Gln Arg Arg Asp Ala Leu Ala Lys Ala Ser Gln Ser Tyr
305                 310                 315                 320

Ile Pro Ser Tyr Val Thr Arg Pro Ala Val Gly Leu Glu Val Ile
                325                 330                 335

Ile Ser Asp Ser Asn Ser Glu Ser Pro Pro Tyr Gly Tyr Thr Arg Ile
                340                 345                 350

Asp Tyr Asp Leu Asn Arg Asn Ala Gly Gly Lys Tyr Val Phe Leu Cys
            355                 360                 365

Tyr Lys Gln Lys Asn Ile Ser Val Gly Gly Asp Ala Asp Ala Ile Thr
    370                 375                 380

Asp Val Leu Val Val Tyr Gly Asn Asp Arg Asn Pro Ser Val Pro Ser
385                 390                 395                 400

Gly Tyr Thr Lys Ile Asp Lys Asp Leu Asn Ser Gly Ala Gly Gly Lys
                405                 410                 415

Tyr Ile Tyr Phe Cys Tyr Ser Lys Asp Lys Arg Lys Gln Glu Glu Gly
                420                 425                 430

Leu Pro Ile Arg Gly Leu Arg Val Val Gly Pro His Pro Thr Ser Val
            435                 440                 445

Ala Pro Tyr Gly Phe Ser Lys Ile Asp Ile Asp Leu Asn Met Gly Ala
    450                 455                 460

Gly Gly Asp Phe Ile Tyr Leu Cys Lys Ser Arg His Leu Glu
465                 470                 475

<210> SEQ ID NO 6
<211> LENGTH: 27
<212> TYPE: DNA
<213> ORGANISM: Artificial Sequence
<220> FEATURE:
<223> OTHER INFORMATION: Synthetic

<400> SEQUENCE: 6
gcatctagga ccgactagct aactaac                                              27

<210> SEQ ID NO 7
<211> LENGTH: 24
<212> TYPE: DNA
<213> ORGANISM: Artificial Sequence
<220> FEATURE:
<223> OTHER INFORMATION: Synthetic

<400> SEQUENCE: 7
ctttgcatca tgtcttgaac aatg                                                 24

<210> SEQ ID NO 8
<211> LENGTH: 15
<212> TYPE: DNA
<213> ORGANISM: Artificial Sequence
<220> FEATURE:
<223> OTHER INFORMATION: Synthetic

<400> SEQUENCE: 8
cgccatgagg agcaa                                                           15

<210> SEQ ID NO 9
<211> LENGTH: 18
```

```
<212> TYPE: DNA
<213> ORGANISM: Artificial Sequence
<220> FEATURE:
<223> OTHER INFORMATION: Synthetic

<400> SEQUENCE: 9
gctggccgtg aaggtgaa                                                    18

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
tccacgctag cgctgaagta                                                  20

<210> SEQ ID NO 11
<211> LENGTH: 14
<212> TYPE: DNA
<213> ORGANISM: Artificial Sequence
<220> FEATURE:
<223> OTHER INFORMATION: Synthetic

<400> SEQUENCE: 11
ctcagcggaa gcta                                                        14

<210> SEQ ID NO 12
<211> LENGTH: 19
<212> TYPE: DNA
<213> ORGANISM: Artificial Sequence
<220> FEATURE:
<223> OTHER INFORMATION: Synthetic

<400> SEQUENCE: 12
tgactgtcaa aggccacgg                                                   19

<210> SEQ ID NO 13
<211> LENGTH: 24
<212> TYPE: DNA
<213> ORGANISM: Artificial Sequence
<220> FEATURE:
<223> OTHER INFORMATION: Synthetic

<400> SEQUENCE: 13
agatggacaa gtctaggttc cacc                                             24

<210> SEQ ID NO 14
<211> LENGTH: 28
<212> TYPE: DNA
<213> ORGANISM: Artificial Sequence
<220> FEATURE:
<223> OTHER INFORMATION: Synthetic

<400> SEQUENCE: 14
ccgtttagcg cgtgtttaca acaagctg                                         28

<210> SEQ ID NO 15
<211> LENGTH: 24
<212> TYPE: DNA
<213> ORGANISM: Artificial Sequence
<220> FEATURE:
<223> OTHER INFORMATION: Synthetic

<400> SEQUENCE: 15
```

```
catcgtgaac cactacatcg agac                                              24

<210> SEQ ID NO 16
<211> LENGTH: 18
<212> TYPE: DNA
<213> ORGANISM: Artificial Sequence
<220> FEATURE:
<223> OTHER INFORMATION: Synthetic

<400> SEQUENCE: 16
gtcgatccac tcctgcgg                                                     18

<210> SEQ ID NO 17
<211> LENGTH: 22
<212> TYPE: DNA
<213> ORGANISM: Artificial Sequence
<220> FEATURE:
<223> OTHER INFORMATION: Synthetic

<400> SEQUENCE: 17
accgtgaact tccgcaccga gc                                                22

<210> SEQ ID NO 18
<211> LENGTH: 23
<212> TYPE: DNA
<213> ORGANISM: Artificial Sequence
<220> FEATURE:
<223> OTHER INFORMATION: Synthetic

<400> SEQUENCE: 18
ttggactaga aatctcgtgc tga                                               23

<210> SEQ ID NO 19
<211> LENGTH: 22
<212> TYPE: DNA
<213> ORGANISM: Artificial Sequence
<220> FEATURE:
<223> OTHER INFORMATION: Synthetic

<400> SEQUENCE: 19
gctacatagg gagccttgtc ct                                                22

<210> SEQ ID NO 20
<211> LENGTH: 16
<212> TYPE: DNA
<213> ORGANISM: Artificial Sequence
<220> FEATURE:
<223> OTHER INFORMATION: Synthetic

<400> SEQUENCE: 20
gcgtttgtgt ggattg                                                       16

<210> SEQ ID NO 21
<211> LENGTH: 72
<212> TYPE: DNA
<213> ORGANISM: Artificial Sequence
<220> FEATURE:
<223> OTHER INFORMATION: Synthetic

<400> SEQUENCE: 21
gcatctagga ccgactagct aactaactag ggcgccatga ggagcaatca ttgttcaaga       60
catgatgcaa ag                                                           72

<210> SEQ ID NO 22
<211> LENGTH: 57
```

<212> TYPE: DNA
<213> ORGANISM: Artificial Sequence
<220> FEATURE:
<223> OTHER INFORMATION: Synthetic

<400> SEQUENCE: 22
gctggccgtg aaggtgaagc tcagcggaag ctacggctac ttcagcgcta gcgtgga    57

<210> SEQ ID NO 23
<211> LENGTH: 113
<212> TYPE: DNA
<213> ORGANISM: Artificial Sequence
<220> FEATURE:
<223> OTHER INFORMATION: Synthetic

<400> SEQUENCE: 23
tgactgtcaa aggccacggc cgtttagcgc gtgtttacaa caagctgtaa gagcttactg    60
aaaaaattaa catctcttgc taagctgggg gtggaaccta gacttgtcca tct    113

<210> SEQ ID NO 24
<211> LENGTH: 76
<212> TYPE: DNA
<213> ORGANISM: Artificial Sequence
<220> FEATURE:
<223> OTHER INFORMATION: Synthetic

<400> SEQUENCE: 24
catcgtgaac cactacatcg agacctccac cgtgaacttc cgcaccgagc cgcagacccc    60
gcaggagtgg atcgac    76

<210> SEQ ID NO 25
<211> LENGTH: 79
<212> TYPE: DNA
<213> ORGANISM: Artificial Sequence
<220> FEATURE:
<223> OTHER INFORMATION: Synthetic

<400> SEQUENCE: 25
ttggactaga aatctcgtgc tgattaattg ttttacgcgt gcgtttgtgt ggattgtagg    60
acaaggctcc ctatgtagc    79

<210> SEQ ID NO 26
<211> LENGTH: 10
<212> TYPE: DNA
<213> ORGANISM: Artificial Sequence
<220> FEATURE:
<223> OTHER INFORMATION: Synthetic

<400> SEQUENCE: 26
cgaggggtac    10

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
aggatcgagg ggtacctcac    20

<210> SEQ ID NO 28
<211> LENGTH: 50
<212> TYPE: DNA

```
<213> ORGANISM: Artificial Sequence
<220> FEATURE:
<223> OTHER INFORMATION: Synthetic

<400> SEQUENCE: 28
ccatggtgca taatgaggat cgaggggtac ctcactgact agctaatcga          50

<210> SEQ ID NO 29
<211> LENGTH: 10
<212> TYPE: DNA
<213> ORGANISM: Artificial Sequence
<220> FEATURE:
<223> OTHER INFORMATION: Synthetic

<400> SEQUENCE: 29
gcgccatgag                                                      10

<210> SEQ ID NO 30
<211> LENGTH: 20
<212> TYPE: DNA
<213> ORGANISM: Artificial Sequence
<220> FEATURE:
<223> OTHER INFORMATION: Synthetic

<400> SEQUENCE: 30
agggcgcgcc atgaggagca                                           20

<210> SEQ ID NO 31
<211> LENGTH: 50
<212> TYPE: DNA
<213> ORGANISM: Artificial Sequence
<220> FEATURE:
<223> OTHER INFORMATION: Synthetic

<400> SEQUENCE: 31
actagctaac taactagggc gcgccatgag gagcaatcat tgttcaagac          50

<210> SEQ ID NO 32
<211> LENGTH: 24867
<212> TYPE: DNA
<213> ORGANISM: Artificial Sequence
<220> FEATURE:
<223> OTHER INFORMATION: Synthetic

<400> SEQUENCE: 32
cgtactgcac tgccaccatt caagacaagc tatggtcgtc gccgtgaacg tgagccgcgc    60
atcgttgaag gctaggtcca cgaggaggta gacaagggca catgcgctcc caagagcttg   120
ttcgtgttcg tgacccgacg accgcgcgcg tttgtccgtg ggctcgtggg acgccagcag   180
cccacgcgaa acggttcccc tgccgcgcgc gcgcgcgccc ggtgcatggc tctcctcagc   240
ctccgaatgg agtcatcacc gtcgacgcct cgacggcgcg gaggtgacca aataaggtcc   300
ggctgctcgc agccgtggca cgaaacgagg acacacggac tggtaggagg ctaggggggg   360
cacggacaag accgctccgt tccgttgcct ctcccgcgct ctgcgaggga tgatgcatgg   420
gcagcgcgcg gacacacgga ctggcagcgg ccctgtaccc acgtcgcagt gccgggatcc   480
gcgcctacca cggcacgatc agcgtcatca tggcacaatc attcacgaac ctcccagtcc   540
cagcggattg cacgccgaaa atcgtcctc tagaagaaag ctttttctcg tcgcacatcg    600
gcgcttctgc tcggcacggc atgtgaaact gtcagggcac aggggtaggt ttactgacaa   660
ggtttgattt cttttccggc tgctgagcac ggtccgcgca tggagcaaa ttcaatgccc    720 ttgctttctc ccgtcccggc ccattcaaac cgggccgtcg ttttagtttc ttttatgtt    780
```

```
ttacttggtt ttagcggcga ggcgatgcaa cgaagaccac agcagcaaac tactattgtt    840
tcagggtcat ttctaataca ctctccgtcc taaaatatta ggtggcgctt ggcagagttt    900
ccacagcttc gctcagagcg agaatcactc ttactgagct aaatgataaa aatcggaact    960
gcttcatgtt gagagtggag tgaatctagt ctacactatg tattagaaag tgagagaaaa   1020
aaaacatgct tcccactaca ctactcccaa catgctcccc actctttaac ccctcatgaa   1080
tcatttcaca gcctatttgc caaacaattt tcgtcaaata tattcacttc tagtagagaa   1140
tcactcagaa tcaccaatca gctctcggaa ctagagaatt gatcaaagac aaactctatt   1200
accttcaatg atatgtggtt atgattcatg ttggcaagct gtgatcctgt tgctgctgtt   1260
cccctggtac tttttttttt gtgtgccggt tgagttttta tagtttatgt tgtgctgcat   1320
atgaatgagt tttggtagtt accgtggttg ccgttcacag cggcgttgcc tgctgttcat   1380
atgttggcaa tccgtgaatt tgcatgcttc tatatatgag tttggtgttc aattgtactt   1440
atatactacc aaaaaatacc atagtttcag tgggctgaag aaattaaaac ccatgcatgc   1500
tagtaatgtc atagctaggt gtataccatg gttttccaat accaaactta gctaccaaac   1560
acatactact gcatctgtat atataatgca ctggtgtgca gccgtcagcc gtgtgccttc   1620
tgaagcgtga aacctggtaa aaaaaaaaaa cgggggaggc aagaagcatc agggcaggca   1680
ggaggatcct agtacatatc ctacttactg gcttgcagca aggctagctg atggctgcgt   1740
gcgtgcttac atgatgatga tcatgcgtgt cgttcgtact cgtacgagga tcgaggaaag   1800
acaccataac tcaccttcaa cagacaccct tcgttaggag catgcacgga tagatggcgt   1860
ctagcatatc gataggacat gacaagtggt acgatccccg tcacatgtcc atggaggcat   1920 ctgtatatgga cacggcgtgt atctatcgcg gctggaacag aaccagcgct cgcgcggcgg   1980
tcggcgggag ggacagacct tggctccgtg cgttcaggtt gtgcttgtgc cgcgcgccac   2040
gcacggtctc cgccgcctgc agctgaaatt ttagatttac atcctatccc tttatttttt   2100
ttatttgtca caattcagtt caaaaatgaa gaacggaggt agtgcatcct ttgtgagact   2160
aatgaaaatc acatctggat cctgaaatcg gcgtcgtaac ctacaaggcc acggactgga   2220
ttagatagtg gtccatggtg cataatgagg atcgaggggc acctcactga ctagctaatc   2280
gagctagtta ccctatgagg tgacatgaag cgctcacggt tactatgacg gttagcttca   2340
cgactgttgg tggcagtagc gtacgactta gctatagttc cggacttacc gataacttcg   2400
tatagcatac attatacgaa gttatggcgc cgctagcctg cagtgcagcg tgacccggtc   2460
gtgcccctct ctagagataa tgagcattgc atgtctaagt tataaaaaat taccacatat   2520 ttttttttgtc acacttgttt gaagtgcagt ttatctatct ttatacatat atttaaactt   2580
tactctacga ataatataat ctatagtact acaataatat cagtgtttta gagaatcata   2640
taaatgaaca gttagacatg gtctaaagga caattgagta ttttgacaac aggactctac   2700
agttttatct ttttagtgtg catgtgttct ccttttttt tgcaaatagc ttcacctata   2760
taatacttca tccattttat tagtacatcc atttagggtt tagggttaat ggttttata   2820 gactaatttt tttagtacat ctatttatt ctattttagc ctctaaatta agaaaactaa   2880
aactctattt tagtttttttt atttaataat ttagatataa aatagaataa cctaaagtga   2940
ctaaaaatta aacaaatacc ctttaagaaa ttaaaaaaac taaggaaaca ttttcttgt    3000 ttcgagtaga taatgccagc ctgttaaacg ccgtcgacga gtctaacgga caccaaccag   3060
cgaaccagca gcgtcgcgtc gggccaagcg aagcagacgg cacggcatct ctgtcgctgc   3120
```

```
ctctggaccc ctctcgagag ttccgctcca ccgttggact tgctccgctg tcggcatcca    3180
gaaattgcgt ggcggagcgg cagacgtgag ccggcacggc aggcggcctc ctcctcctct    3240
cacggcaccg gcagctacgg gggattcctt tcccaccgct ccttcgcttt ccctccctcg    3300
cccgccgtaa taaatagaca ccccctccac accctctttc cccaacctcg tgttgttcgg    3360
agcgcacaca cacacaacca gatctccccc aaatccaccc gtcggcacct ccgcttcaag    3420
gtacgccgct cgtcctcccc ccccccctc tctaccttct ctagatcggc gttccggtcc    3480
atgcatggtt agggcccggt agttctactt ctgttcatgt ttgtgttaga tccgtgtttg    3540
tgttagatcc gtgctgctag cgttcgtaca cggatgcgac ctgtacgtca gacacgttct    3600
gattgctaac ttgccagtgt ttctctttgg ggaatcctgg gatggctcta gccgttccgc    3660
agacgggatc gatttcatga ttttttttgt ttcgttgcat agggtttggt ttgcccttt     3720
cctttatttc aatatatgcc gtgcacttgt ttgtcgggtc atcttttcat gcttttttt     3780
gtcttggttg tgatgatgtg gtctggttgg gcggtcgttc tagatcggag tagaattctg    3840
tttcaaacta cctggtggat ttattaattt tggatctgta tgtgtgtgcc atacatattc    3900
atagttacga attgaagatg atggatggaa atatcgatct aggataggta tacatgttga    3960
tgcgggtttt actgatgcat atacagagat gcttttttgtt cgcttggttg tgatgatgtg   4020
gtgtggttgg gcggtcgttc attcgttcta gatcggagta gaatactgtt tcaaactacc    4080
tggtgtattt attaattttg gaactgtatg tgtgtgtcat acatcttcat agttacgagt    4140
ttaagatgga tggaaatatc gatctaggat aggtatacat gttgatgtgg gttttactga    4200
tgcatataca tgatggcata tgcagcatct attcatatgc tctaaccttg agtacctatc    4260
tattataata aacaagtatg ttttataatt attttgatct tgatatactt ggatgatggc    4320
atatgcagca gctatatgtg gatttttta gccctgcctt catacgctat ttatttgctt     4380
ggtactgttt cttttgtcga tgctcaccct gttgtttggt gttacttctg caggtcgact    4440
ttaacttagc ctagggaagt tcctattccg aagttcctat tctctagaaa gtataggaac    4500
ttcagatcca ccgggatccc cgatcatgca aaaactcatt aactcagtgc aaaactatgc    4560
ctggggcagc aaaacggcgt tgactgaact ttatggtatg gaaaatccgt ccagccagcc    4620
gatggccgag ctgtggatgg gcgcacatcc gaaaagcagt tcacgagtgc agaatgccgc    4680
cggagatatc gtttcactgc gtgatgtgat tgagagtgat aaatcgactc tgctcggaga    4740
ggccgttgcc aaacgctttg gcgaactgcc tttcctgttc aaagtattat gcgcagcaca    4800
gccactctcc attcaggttc atccaaacaa acacaattct gaaatcggtt ttgccaaaga    4860
aaatgccgca ggtatcccga tggatgccgc cgagcgtaac tataaagatc ctaaccacaa    4920
gccgagctg gttttttgcgc tgacgccttt ccttgcgatg aacgcgtttc gtgaattttc    4980
cgagattgtc tccctactcc agccggtcgc aggtgcacat ccggcgattg ctcactttt    5040
acaacagcct gatgccgaac gtttaagcga actgttcgcc agcctgttga atatgcaggg    5100
tgaagaaaaa tcccgcgcgc tggcgatttt aaaatcggcc ctcgatagcc agcagggtga    5160
accgtggcaa acgattcgtt taatttctga attttacccg gaagacagcg gtctgttctc    5220
cccgctattg ctgaatgtgg tgaaattgaa ccctggcgaa gcgatgttcc tgttcgctga    5280
aacaccgcac gcttacctgc aaggcgtggc gctggaagtg atggcaaact ccgataacgt    5340
gctgcgtgcg ggtctgacgc ctaaatacat tgatattccg gaactggttg ccaatgtgaa    5400
attcgaagcc aaaccggcta accagttgtt gacccagccg gtgaaacaag gtgcagaact    5460
ggacttcccg attccagtgg atgattttgc cttctcgctg catgacctta gtgataaaga    5520
```

```
aaccaccatt agccagcaga gtgccgccat tttgttctgc gtcgaaggcg atgcaacgtt    5580
gtggaaaggt tctcagcagt tacagcttaa accgggtgaa tcagcgttta ttgccgccaa    5640
cgaatcaccg gtgactgtca aaggccacgg ccgtttagcg cgtgtttaca acaagctgta    5700
agagcttact gaaaaaatta acatctcttg ctaagctggg ggtggaacct agacttgtcc    5760
atcttctgga ttggccaact taattaatgt atgaaataaa aggatgcaca catagtgaca    5820
tgctaatcac tataatgtgg gcatcaaagt tgtgtgttat gtgtaattac tagttatctg    5880
aataaaagag aaagagatca tccatatttc ttatcctaaa tgaatgtcac gtgtctttat    5940
aattctttga tgaaccagat gcatttcatt aaccaaatcc atatacatat aaatattaat    6000
catatataat taatatcaat tgggttagca aaacaaatct agtctaggtg tgttttgcga    6060
atgcgacctt cttatgtgct tctagtctcc aaatgtggtt gatagttatt ttgctctaag    6120
atcaacagta atgaagtata aatcatcgtt gtggtgtgct actcggttaa ttgagcatta    6180
acacacacaa acatgacgag gatggtataa tctccaaaaa tgtgtacttt gttaggtggg    6240
accctatagc cttgattaat gtgctatgtt aggcatgcct ggaaacgtgt gacgcatatg    6300
ttttgtgaac ctgttgatat tatatgtgct tttatattac catattttat taaaatacta    6360
atatttatta ctagtaagat ataacattct atctagctta aaaactaacc ataaatattc    6420
cataataact agatttacca aactaatata ctaaatatac ataataaata caaaattaac    6480
aagacaataa tcaatattta tgagcttaat atatttagac attatggttg gtcgacgata    6540
atcatgctaa cttttcgtaa ttgcttgatt gaaatatgct tagaataatg cctcttttgtt   6600 ctacatggca aatagggacc attatggtgt aacaccctgg gaaccacaaa caccccgaaa    6660
tgctactaaa ctacacaact aaccttcata tataaaattt cgacagcatc tcctttgaaa    6720
atttgcatag acgtggaagc aacagagtat aaacagatat catgataaga aaacatacta    6780
gacattaata atctgctaga aatgggaaga atcctaactt gacgactgcg taactgacta    6840
gagtcacact tagctgaccc tagtcactta caactgactt cgtgtcctag cttaggcta    6900 ctgctagtcc gcggtgtatc cgtgatcgag ttggcgccag acggaatctg ttctccatcg    6960
ctgacatcct cgagtagatc acattcaagc ttgatatcga attcctgcag cccatccctc    7020
agccgccttt cactatcttt tttgcccgag tcattgtcat gtgaaccttg gcatgtataa    7080
tcggtgaatt gcgtcgattt tcctcttata ggtgggccaa tgaatccgtg tgatcgcgtc    7140
tgattggcta gagatatgtt tcttccttgt tggatgtatt ttcatacata atcatatgca    7200
tacaaatatt tcattacact ttatagaaat ggtcagtaat aaaccctatc actatgtctg    7260
gtgtttcatt ttatttgctt ttaaacgaaa attgacttcc tgattcaata tttaaggatc    7320
gtcaacggtg tgcagttact aaattctggt ttgtaggaac tatagtaaac tattcaagtc    7380
ttcacttatt gtgcactcac ctctcgccac atcaccacag atgttattca cgtcttaaat    7440
ttgaactaca catcatattg acacaatatt tttttttaaat aagcgattaa aacctagcct   7500
ctatgtcaac aatggtgtac ataaccagcg aagtttaggg agtaaaaaac atcgccttac    7560
acaaagttcg ctttaaaaaa taagagtaa attttacttt ggaccaccct tcaaccaatg    7620
tttcacttta gaacgagtaa ttttattatt gtcactttgg accaccctca aatctttttt    7680
ccatctacat ccaatttatc atgtcaaaga aatggtctac atacagctaa ggagatttat    7740
cgacgaatag tagctagcat actcgaggtc attcatatgc ttgagaagag agtcgggata    7800
gtccaaaata aaacaaaggt aagattacct ggtcaaaagt gaaaacatca gttaaaaggt    7860
```

| | |
|---|---|
| ggtataaagt aaaatatcgg taataaaagg tggcccaaag tgaaatttac tcttttctac | 7920 |
| tattataaaa attgaggatg tttttgtcgg tactttgata cgtcattttt gtatgaattg | 7980 |
| gttttttaagt ttattcgctt ttggaaatgc atatctgtat ttgagtcggg ttttaagttc | 8040 |
| gtttgctttt gtaaatacag agggatttgt ataagaaata tctttaaaaa aacccatatg | 8100 |
| ctaatttgac ataattttg agaaaaatat atattcaggc gaattctcac aatgaacaat | 8160 |
| aataagatta aaatagcttt cccccgttgc agcgcatggg tattttttct agtaaaaata | 8220 |
| aaagataaac ttagactcaa aacatttaca aaaacaaccc ctaaagttcc taaagcccaa | 8280 |
| agtgctatcc acgatccata gcaagccag cccaacccaa cccaacccaa cccaccccag | 8340 |
| tccagccaac tggacaatag tctccacacc cccccactat caccgtgagt tgtccgcacg | 8400 |
| caccgcacgt ctcgcagcca aaaaaaaaaa aagaaagaaa aaaagaaaa agaaaaaaca | 8460 |
| gcaggtgggt ccgggtcgtg ggggccggaa acgcgaggag gatcgcgagc cagcgacgag | 8520 |
| gccggccctc cctccgcttc caaagaaacg ccccccatcg ccactatata catacccccc | 8580 |
| cctctcctcc catcccccca accctaccac caccaccacc accacctcca cctcctcccc | 8640 |
| cctcgctgcc ggacgacgag ctcctccccc ctccccctcc gccgccgccg cgccggtaac | 8700 |
| caccccgccc ctctcctctt tctttctccg tttttttttt ccgtcacggt ctcgatcttt | 8760 |
| ggccttggta gtttgggtgg gcgagaggcg gcttcgtgcg cgcccagatc ggtgcgcggg | 8820 |
| aggggcggga tctcgcggct ggggctctcg ccggcgtgga tcaggcccgg atctcgcggg | 8880 |
| gaatggggct ctcggatgta gatctgcgat ccgccgttgt tgggggagat gatgggggt | 8940 |
| ttaaaatttc cgccatgcta aacaagatca ggaagagggg aaaagggcac tatggtttat | 9000 |
| atttttatat atttctgctg cttcgtcagg cttagatgtg ctagatcttt ctttcttctt | 9060 |
| tttgtgggta gaatttgaat ccctcagcat tgttcatcgg tagtttttct tttcatgatt | 9120 |
| tgtgacaaat gcagcctcgt gcggagcttt tttgtaggta gaaggatcca cacgacacca | 9180 |
| tgtccccga gcgccgcccc gtcgagatcc gccggccac cgccgccgac atggccgccg | 9240 |
| tgtgcgacat cgtgaaccac tacatcgaga cctccaccgt gaacttccgc accgagccgc | 9300 |
| agaccccgca ggagtggatc gacgacctgg agcgcctcca ggaccgctac ccgtggctcg | 9360 |
| tggccgaggt ggagggcgtg gtggccggca tcgcctacgc cggcccgtgg aaggcccgca | 9420 |
| acgcctacga ctggaccgtg gagtccaccg tgtacgtgtc ccaccgccac cagcgcctcg | 9480 |
| gcctcggctc caccctctac acccacctcc tcaagagcat ggaggcccag ggcttcaagt | 9540 |
| ccgtggtggc cgtgatcggc ctcccgaacg accgtccgt gcgcctccac gaggccctcg | 9600 |
| gctacaccgc ccgcggcacc ctgcgcgccg ccggctacaa gcacggcggc tggcacgacg | 9660 |
| tcggcttctg gcagcgcgac ttcgagctgc cggcccgcc gcgccggtg cgcccggtga | 9720 |
| cgcagatctg agtcgacctg caggcatgcc gctgaaatca ccagtctctc tctacaaatc | 9780 |
| tatctctctc tataataatg tgtgagtagt tcccagataa gggaattagg gttcttatag | 9840 |
| ggtttcgctc atgtgttgag catataagaa acccttagta tgtatttgta tttgtaaaat | 9900 |
| acttctatca ataaaatttc taattcctaa aaccaaaatc cagtggcgag ctaatgcggc | 9960 |
| ccgaataact tcgtatagca tacattatac gaagttatac ctggtggcgc cgctaggggc | 10020 |
| tgcaggaatt cctgcagccc gggggatcca ctagttctag agcggccgac ctcgacagat | 10080 |
| ctaagcttac tagtgccgtg gtcgtttaa gctgccgctg tacctgtgtc gtctggtgcc | 10140 |
| ttctggtgta cctgggaggt tgtcgtctat caagtatctg tggttggtgt catgagtcag | 10200 |
| tgagtcccaa tactgttcgt gtcctgtgtg cattatacc aaaactgtta tgggcaaatc | 10260 |

```
atgaataagc ttgatgttcg aacttaaaag tctctgctca atatggtatt atggttgttt    10320
ttgttcgtct cctaatattt gcctgggatc aaatttatt ggctggtgtt catttgacct    10380
ccatgttctt gctaggctcc attttttact ctacagccat aatatgtttg attgtttggt    10440
ttgttctttg ttgtacacct ggttctgtcg agcttagttt tcgacactgg cttacagctt    10500
aacatgttgc tattttattg ggttctgatt gctattttat tgggttctga ttgctagttt    10560
ttgctgaatc caaaaaccat gttatttatt taagcgatcc aggttattat tatgatggtg    10620
gctaagtttt ttttttttcca agggtaaatt ttctggattc tccagtgttt ctgtggccga    10680
attcactagt gattcagatc tgatatcgat gggcccacta actatctata ctgtaataat    10740
gttgtatagc cgccggatag ctagctagtt tagtcattca gcggcgatgg gtaataataa    10800
agtgtcatcc atccatcacc atgggtggca acgtgagcaa tgacctgatt gaacaaattg    10860
aaatgaaaag aagaaatatg ttatatgtca acgagatttc ctcataatgc cactgacgac    10920
gtgtgtccaa gaaatgtatc agtgatacgt atattcacaa tttttttatg acttatactc    10980
acaatttgtt tttttactac ttatactcac aatttgttgt gggtaccata acaatttcga    11040
tcgaatatat atcagaaagt tgacgaaagt aagctcactc aaaaagttaa atgggctgcg    11100
gaagctgcgt caggcccaag ttttggctat tctatccggt atccacgatt ttgatggctg    11160
agggacatat gttcgcttaa gcttggtcac ccggtccggg cctagaaggc cagcttcaag    11220
tttgtacaaa aaagcaggct ccggccagaa tctcactgac tagctaaaca gcggccgctt    11280
ttaagtatga ccaattttta agtataaacc cctcacgatt ggttatttt ttaagtataa    11340
ccaattttta agtataaacc cctcaccaat ttttaagtat aaacctagcg actaataaac    11400
acaacttctt gccaaagtgt gagcatcacc attggatctg cgcccctcac gaacagtctt    11460
cgccggggta aaattctcca aattaaagtc atcttgatgt ccttgatcac ctgtccataa    11520
ggcccaatcc cagctccacg tatacttctg ataagattga catagtcact tgcatgccag    11580
tgtggaactc tggatgccta ggtcagaggc tagtgactgg ccttcccggc atgctagcat    11640
gtagcatgcc aaggatctgg ctgctccagg tttgttatgc ctgacatcac catagggatg    11700
agagcaagta taataatagg ctgtaagctt taaatgctca ggtggagaaa aaaggagag    11760
gagaggagag agaaaagtgg gctataagct tatagctgtg ttagacataa gaatcagaaa    11820
cttcgtatga gagacaggtg agctatatat taataacaaa gagctaacta ttatatgagt    11880
gaaccgagag aaggctgtaa aaaaacttac acaatcaacg atcgacatta ttattaacct    11940
tgctctgtct tgcgagacct ctttgacaaa gctacatcaa tgccggccaa gtgccttggg    12000
atttgggaat ggcttctttc ctccccttcct cggttgtccc ccaaggccta ggcttgccac    12060
gctgtattca gtcgcagccg cctttacttt tgcccctttgt ggaagttttg taataaatgg    12120
tctgattcta tcttcggata gatgaagccg gatgtttcat ccattatcta aaaaaaagtt    12180
ggttgctttg ctgagctaag aaagtgtaat ccagagtgcc cgtaacgtat tcatgtacat    12240
aactattatc taatataaat cttcttttgt cgcaaaaaaa ggtcggccca tcagaacaaa    12300
tgatcaatgt aaggcccaaa atttgtgtct caaatgtcat ttacgtttcc aagctaaaca    12360
aaaacacagg attcatataa ttttgctggt ggcttaggct tcgtccaata gtgcttagtt    12420
taatttgtat atacctgcac catggtattc gtctggcctt ggatcttgcg catcaattgc    12480
ctatggacga tgatcgcagc cacgccacat tcattttaa tcgccatttg cttgacaccc    12540
aatgcctctg caccacttgc gcacgctacg caccgtctga tacgccaaga tcccgagcta    12600
```

```
aaataacacc caatcatcag atgaaaacaa gcgcgagtgc gagccagccc atggcagcga   12660
tcttggccat ttgcggagcc aactgaaagc cgtgcacaaa atattcgaca ccgtataagg   12720
gaaaacacta gttatacgag gtgggcaata atccagatct cggactcttc ctaacccggt   12780
tcacatgcat agcatatatg atggccggcc ggggttcaca tgaacgccat cccgtgccct   12840
agtgcactga tttcttaatt tcgaatttta agtatgacca attttaagt ataaacccct    12900 cacgattggt tatttttta agtataacca attttaagt ataaacccct caccaatttt    12960
taagtataaa cctagcgact aataaacaca acttcttgcc aaagtgtgag catcaccatt   13020
ggatctgcgc ccctcacgaa cagtcttcgc cggggtaaaa ttctccaaat taaagtcatc   13080
ttgatgtcct tgatcaccctg tccataaggc ccaatcccag ctccacgtat acttctgata   13140
agattgacat agtcacttgc atgccagtgt ggaactctgg atgcctaggt cagaggctag   13200
tgactggcct tcccggcatg ctagcatgta gcatgccaag gatctggctg ctccaggttt   13260
gttatgcctg acatcaccat agggatgaga gcaagtataa aataggctg taagctttaa    13320 atgctcaggt ggagaaaaaa aggagaggag aggagagaga aaagtgggct ataagcttat   13380
agctgtgtta gacataagaa tcagaaactt cgtatgagag acaggtgagc tatatattaa   13440
taacaaagag ctaactatta tatgagtgaa ccgagagaag gctgtaaaaa aacttacaca   13500
atcaacgatc gacattatta ttaaccttgc tctgtcttgc gagacctctt tgacaaagct   13560
acatcaatgc cggccaagtg cctgggatt tgggaatggc ttcttcctc ccttcctcgg     13620 ttgtccccca aggcctaggc ttgccacgct gtattcagtc gcagccgcct ttacttttgc   13680
cctttgtgga agttttgtaa taaatggtct gattctatct tcggatagat gaagccggat   13740
gtttcatcca ttatctaaaa aaagttggt tgctttgctg agctaagaaa gtgtaatcca    13800
gagtgcccgt aacgtattca tgtacataac tattatctaa tataaatctt cttttgtcgc   13860 aaaaaaggt cggcccatca gaacaaatga tcaatgtaag gcccaaaatt tgtgtctcaa    13920
atgtcattta cgtttccaag ctaaacaaaa acacaggatt catataattt tgctggtggc   13980
ttaggcttcg tccaatagtg cttagtttaa tttgtatata cctgcaccat ggtattcgtc   14040
tggccttgga tcttgcgcat caattgccta tggacgatga tcgcagccac gccacattca   14100
tttttaatcg ccatttgctt gacacccaat gcctctgcac cacttgcgca cgctacgcac   14160
cgtctgatac gccaagatcc cgagctaaaa taacacccaa tcatcagatg aaaacaagcg   14220
cgagtgcgag ccagcccatg gcagcgatct tggccatttg cggagccaac tgaaagccgt   14280
gcacaaaata ttcgacaccg tataagggaa aacactagtt atacgaggtg gcaataatc    14340 cagatctcgg actcttccta acccggttca catgcatagc atatatgatg gccggccggg   14400
gttcacatga acgccatccc gtgccctagt gcactgattt cttaatgtcg acgggccgct   14460
tttaagtatg accaatttt aagtataaac ccctcacgat tggttatttt tttaagtata    14520
accaattttt aagtataaac ccctcaccaa ttttaagta taaacctagc gactaataaa    14580
cacaacttct tgccaaagtg tgagcatcac cattggatct gcgcccctca cgaacagtct   14640
tcgccggggt aaaattctcc aaattaaagt catcttgatg tccttgatca cctgtccata   14700
aggcccaatc ccagctccac gtatacttct gataagattg acatagtcac ttgcatgcca   14760
gtgtggaact ctggatgcct aggtcagagg ctagtgactg gccttcccgg catgctagca   14820
tgtagcatgc caaggatctg gctgctccag gtttgttatg cctgacatca ccatagggat   14880
gagagcaagt ataataatag gctgtaagct ttaaatgctc aggtggagaa aaaaggaga    14940 ggagaggaga gagaaaagtg ggctataagc ttatagctgt gttagacata agaatcagaa   15000
```

```
acttcgtatg agagacaggt gagctatata ttaataacaa agagctaact attatatgag   15060
tgaaccgaga gaaggctgta aaaaaactta cacaatcaac gatcgacatt attattaacc   15120
ttgctctgtc ttgcgagacc tctttgacaa agctacatca atgccggcca agtgccttgg   15180
gatttgggaa tggcttcttt cctcccttcc tcggttgtcc cccaaggcct aggcttgcca   15240
cgctgtattc agtcgcagcc gcctttactt ttgccctttg tggaagtttt gtaataaatg   15300
gtctgattct atcttcggat agatgaagcc ggatgtttca tccattatct aaaaaaaagt   15360
tggttgcttt gctgagctaa gaaagtgtaa tccagagtgt tcgtaacgta ttcatgtaca   15420
taactattat ctaatataaa tcttcttttg tcgcaaaaaa aggtcggccc atcagaacaa   15480
atgatcaatg taaggcccaa aatttgtgtc tcaaatgtca tttacgtttc caagctaaac   15540
aaaaacacag gattcatata attttgctgg tggcttaggc ttcgtccaat agtgcttagt   15600
ttaatttgta tatacctgca ccatggtatt cgtctggcct tggatcttgc gcatcaattg   15660
cctatggacg atgatcgcag ccacgccaca ttcattttta atcgccattt gcttgacacc   15720
caatgcctct gcaccacttg cgcacgctac gcaccgtctg atacgccaag atcccgagct   15780
aaaataacac ccaatcatca gatgaaaaca agcgcgagtg cgagccagcc catggcagcg   15840
atcttggcca tttgcggagc caactgaaag ccgtgcacaa aatattcgac accgtataag   15900
ggaaaacact agttatacga ggtgggcaat aatccagatc tcggactctt cctaacccgg   15960
ttcacatgca tagcatatat gatggccggc cggggttcac atgaacgcca tcccgtgccc   16020
tagtgcactg atttcttaat cccatccagc atgctcttca attttggtgc tcacccttac   16080
gggtatgccc tcactgcctt ttataattgt ataagggaaa tattattcaa tataatgtcc   16140
taaaaattgg caatatcaat ctaaaaatcg ttatgaatag gatgtaaaca aagctactat   16200
ctgtccatat ataacgtcac aggaaggaca aaaaattcag tcagcgatcg agaacggcaa   16260
agaaaaacca tattattgtt gcttgccgac ataaatttaa gtataggaca aaaaaaaaag   16320
ccacatcata ttacatacta tgggcttacc agacaaaatg aaataaacgt gtgcatgcat   16380
gcatgcatgg tacgaacgtc tggatagagt ctccgagctg agtgtggtcc gacgtggaag   16440
tgtacgtctc aacacacgac gcatgtgacc gacaagggca agttgaagtc tatgcatgga   16500
tgggcctgag cgccgcgctg aatgaatctg gacgggtggt agggcatctc ggtgggcaaa   16560
acaaataact ccgtgtgctg catggctgcc tttggaatct ttgcatgcag ctgtgtgctg   16620
aactgaaacc cttcgctcta tctatataaa cagatgccct tcgctctcgt ctcagcaggc   16680
agcatcgtct caagttttgt tctcctctcc tagctagcca gcacctgcag atctgctcgt   16740
tgccttggta attcatcatg tagtacgtag catcagctag tatttatctc aagtatatat   16800
atacgcatat gtgtcgtcgc agtactttcc cttatctctc tatacacact acacgcatac   16860
ataccaatac catccgtctt aactcttaat cttttgcctgc atacgtacac tgcacgtacg   16920
tactgcaggg ctactgattt tgtggaacga agcggtcgag accggtgatc ttgtaaggtt   16980
cccttccctc ctcccctcac acccctgttc gtgttccttc ggatcggatc tcagtggtga   17040
tgttagacgt ccgcggctgc ctacgtagtg gcattgccgc ccgaaaggtt tgtttaggtg   17100
gggtagatcc gaaacaggcc ggatctggac catgtccgcg gcggggcggc gggacttgat   17160
cgcgtagctg tcgtgtgcat ttctccctac cagtggcgga atcggcgatg tggacctaag   17220
ggctaaggct tatctgctgc cttgaccatt tcgtcgctga caaaaacaaa gtgacaatca   17280
tgccgttctc tgtttgttta tctggatcgt tattacgctg tgaatcctgc gatatgtggc   17340
```

```
taagtgattt ttcttctttt tctgggggca gtttagcctt tgacccagtc ctaggtgtgg   17400
tcactaggac tgtgtagcat gatgagtgag gttgcagcag gctgattgct agtggacgtt   17460
tttttcccca atttgttagg ttttcacgct ccaggttgtg caagtaattt tgctagtgat   17520
tgtgtgatcc atcttcaacg ttgaaccttg ttttcccccc taaaacccccc aacaggaaat   17580 cttgccccga cttctattgc aaaaattgta acgcttagca ccctgattga ctcaattcct   17640
gtcactaggc atgctcggtc aaaagcagat gatttaccac ttagaaactg ccctgccect   17700 gctttccaca tagcatttcg aacttttga ctactattga cacccccta acttgccgaa   17760 ctatttctct cttcagctac tatttaccta gttataatta cataaatgtt tgtgtgtatc   17820
ttgtgcaggg atccgccatg gcagagccga acaagggtgg agcacctgcg atgaagaacg   17880
tcgccaagcc gtcgaccaaa cgcctgatcc cgagctcgat agccgcttcg agccagacta   17940
gcgccaacgc tctgacggag cccettcctg gtctgacgc gatcggccag agctacgacg   18000
cattcgggtt cttcgccaat cccgcagca tcatgaagga gctgttcgag ttcagcccac   18060
aggaggagat cgtcgtcgaa ggcaacacct ggcttctcag cagcgacttc gtctacaccg   18120
ccatccgcga cacagagacc tcgaccgtct cgaggcgcac caaggacgac tacagcaagg   18180
agctggccgt gaaggtgaag ctcagcggaa gctacggcta cttcagcgct agcgtggaga   18240
gcgacttcag ccagagcatc agcgacgcta ccgacacgac gtacaccagc gtccgcaccc   18300
acgtcaacaa gtggcgcctc agcctcaagg acgacgtcgg agctctccgg agcaagctcc   18360
ttcctggtgt caagcaggct ctcgctacga tggacgcaac ccagctcttc gacacgttcg   18420
gcacccacta cgtcagcgag gtcctcgtcg gtggaagagc cgactacgtc gccaccacca   18480
agaccagcgc cttcagctcg agcacctcca tcagcgtcgc tgcagaggcg tcgtttcaga   18540
gcatcgcagg aggcgaagtc agcccgaga gcaaggtcct cgccgagatg ctgcgcgaga   18600
actccagcac acggctctac gcactgggag gctcagcact cccgaacatc acggacccag   18660
cgacctacaa cgcctggctg gagagcatcg acaccatccc ggtcttctgc ggcttcaccc   18720
agaactccct caagtcgatc agcgagctcg cggattcagc ccaacgcaga gacgcactcg   18780
cgaaggcatc ccagtcgtac atccccagct acgtcactcg cccagcagtc gtgggcctcg   18840
aggtcatcat ctccgactcc aactccgaga gccctccata cggctacacc cggatcgact   18900
acgacctcaa ccgcaatgcc ggaggcaagt acgtcttcct ctgctacaag cagaagaaca   18960
tctccgtcgg aggtgacgca gacgcgatca cggacgtcct cgtcgtctac ggcaacgacc   19020
ggaacccaag cgtgccctca ggctacacca agatcgacaa ggacctgaac tccggagctg   19080
gagggaagta catctacttc tgctactcca aggacaagcg caagcaggag gagggccttc   19140
cgatacgcgg acttcgcgtc gttggaccac accctacgtc agtggcaccg tacggcttca   19200
gcaagatcga catcgacctc aacatgggcg caggtgggga cttcatctac ctctgcaagt   19260
cgcggcacct cgagtgagtt aaccccgggt caacccatca ggaaggatga agcgcccctc   19320
attttgtgcc ctaggtcgtg gattgctgga tttaattt acacatttcc ttgtcgatcc   19380
tttctgctgt gtgtggttcg agaatgttag tgtgttatcg caagatctgg gtgtttggaa   19440
gttatctcat tattgggcct cataaattca taattcttgc cagttagtga caactgtagc   19500
ttaggtttac ttctgcttgt agtacatcgc ctagatcgtg ggagtccctc ttttcagacg   19560
aatgtcatga acattggtt tttggaaatg attaggaaga catttgctgt tttgtcgact   19620
gctgtttttt acggccaagt tcagagtttt tttttcatg tacaaagtat cagcagttaa   19680
attatgttac ctttaccatg gttcttcata tttgttttcc ttccattgct caatctatgt   19740
```

```
catcttttga aatggtttgg aaggcatcct ttataggata tatagatata gatttgaagc    19800
ataattgtta ggataagaca ccagctagcc tatgctgcaa cgcacattat tcgaccctta    19860
ataacaacag gtgatttta tattataaaa aagttggaaa agtatacaca agaatttttc    19920
aaaagaaggg taaaagggaa cagccctcct gctcgacaat tggaattggt gtcccgcata    19980
atttttttct gcctttgaga attcaggcgt ctctggattc tagttcacca tttaccaatt    20040
agaaggaata ctatgtatgt ataattctac aatctgcatt ctacacaatc cttctatttt    20100
ctgaatatag ttgcaagact agggctctct tatagtattt ctaattatag ccgctttgca    20160
aagtactgtc atatttgatt aggggtattg gaaagaagga gaaagggtg acaccctgct     20220 tgacaattgg aattgataag cagccagggt accaaggcgc gaaacagccc cctccggcgg    20280
tgtcccccac tgaagaaact atgtgctgta gtatagccgc tggctagcta gctagttgag    20340
tcatttagcg gcgatgattg agtaataatg tgtcacgcat caccatgcat gggtggcagt    20400
ctcagtgtga gcaatgacct gaatgaacaa ttgaaatgaa aagaaaaaag tattgttcca    20460
aattaaacgt tttaaccttt taataggttt atacaataat tgatatatgt tttctgtata    20520
tgtctaattt gttatcatcc atttagatat agacgaaaaa aaatctaaga actaaaacaa    20580
atgctaattt gaaatgaagg gagtatatat tgggataatg tcgatgagat ccctcgtaat    20640
atcaccgaca tcacacgtgt ccagttaatg tatcagtgat acgtgtattc acatttgttg    20700
cgcgtaggcg tacccaacaa ttttgatcga ctatcagaaa gtcaacggaa gcgctgcaga    20760
aacttatctc tgttatgaat cagaagaagt tcatgtctcg tttcatttaa aactttggtg    20820
gtttgtgttt tggggccttg taaagcccct gatgaataat tgttcaacta tgtttccgtt    20880
cctgtgttat acctttcttt ctaatgagta atgacatcaa acttcttctg tattgaaatt    20940
atgtccttgt gagtctcttt atcatcgttt cgtctttaca ttatatgtgc tacttttgtc    21000
taatgagcct gaaagtggc tccaatggta cgcactggaa gatttgttgg cttctggtag     21060
atatagcgac agtgttgagc ttgtaatatc atgtctctta ttgctaaatt agttcctttc    21120
ttaacagaaa ccttcaaagt tttttgttttt gttttcattt acctaatgta cacatacgct   21180
ggccatgact aacaacatgt ccaggcttag agcatatttt tttctagctt aaattgttaa    21240
cttgtcattc agtaaaatcc gagaattgtg aagctctaat tgaagctaat tcgtttttata   21300 aagtcagtta aaaagtatac taaattatcc aactttcttt caaaatctca aaattctatg    21360
acaaaacgat agtctttgtt tatgtcagta ccacaaagag gtggaaaaaa acaccaaaaa    21420
aacaataagc aaactataca ctgagaagaa aaataaaaga gagctcaata gatgttttat    21480
actaacggta gattagatca aagatccaag ctttactcta catagagcag aacccagaat    21540
cccttcatat ctctttttatt ctagcaccga taatctactg aaaagaagac acttagagct   21600
ctgtctcttt gtcaaagaag tcccagccgt catccagaag ctccttacgt tcattaacag    21660
agaattcgac aaagcagcat tagtccgttg atcggtggaa gaccactcgt cagtgttgag    21720
ttgaatgttt gatcaataaa atacggcaat gctgtaaggg ttgttttta tgccattgat     21780 aatacactgt actgttcagt tgttgaactc tatttcttag ccatgccaag tgcttttctt    21840
attttgaata acattacagc aaaaagttga aagacaaaaa aaaaacccc cgaacagagt     21900 gctttgggtc ccaagcttct ttagactgtg ttcggcgttc cccctaaatt tctccccta    21960 tatctcactc acttgtcaca tcagcgttct ctttcccct atatctccac gctctacagc    22020
agttccacct atatcaaacc tctataccc accacaacaa tattatatac tttcatcttc    22080
```

```
aactaactca tgtaccttcc aattttttc tactaataat tatttacgtg cacagaaact    22140
tagcaaggag agagagagcg gggtgaccaa gcttggcgcg ccattctatc actagctagc    22200
tgctaattat tcccgggcac ccagctttct tgtacaaagt ggccgttaca gaatcactga    22260
ctagctaatc tagcggccgc tcaagcttcg gcatgcaatt cgcataccta cagtacaacg    22320
tggccaaagt catcatttaa tgagctctcg ggcgcgccgt ctcactagct agctgctaac    22380
gttcccgggc aactttatta tacaaagttg atagatccta caggccagaa tggcctctgg    22440
attcagcggc ctagaaggcc gaagtacttg gtcttcctaa tatcggaccg aggaccgatt    22500
aaactttaat tcggtccgtc aatattcacc gaagcgacta attaactagc tgtcccacgg    22560
cctaactagc acttaatccc ctagcctaac ctaagagcgc taatctaggc tagtggtcac    22620
ttagggcttt aaggctagcg tatacgaagt tcctattccg aagttcctat tcttcaaaaa    22680
gtataggaac ttctgtacac ctgagctgat tccgatgact tcgtaggttc ctagctcaag    22740
ccgctcgtgt ccaagcgtca cttacgatta gctaatgatt acggcatcta ggaccgacta    22800
gctaactaac tagggcgcgc catgaggagc aatcattgtt caagacatga tgcaaagcta    22860
gaaaactttg attgtggccg tcctaattgt gaagtttagg ccggggggaa cttcatgaac    22920
cctatcgaag cttaattagt tctttttgt tgttagccat gtttgtattg tagtttaggt    22980
gaacaacatg acgccgcacc cgcgatctca gggctcgtcc ccacacagga gggcacgtcg    23040
tcgtcttcgc cgccgagcat cagagattca gagcacgtac acgcacatct caagcaaacg    23100
gagtagtacg tcctactcct acgtacatac ctagccgacg acctttatgt gcacaccacc    23160
actgctctgc tgcccggcct ctccgtcgtc cgttcatcac cagctggtct ggtccttcaa    23220
tttccatgcg tcggtccgaa gtcaacattt tccgtcaatt catggccaaa ggctacaact    23280
aacattgttt aatgtcgact gttttttttt tgttaatgtg acgccgtgtt tttttgtta    23340
ttgctagaac actgtttaat gtcaaactgt tttaagtcca tgggacgcct cagcaatagt    23400
agccttttgt taatgtgacg ccgcatcaat caactaatta aagcccttaa ccatctgtgt    23460
ctcattgtta ccggcatcac ctaaacaaca gatcacggct ctacgagcaa cgtacataac    23520
agtaaactaa tggcctgatc tgctgggcta gtagggccac agcaacacta gctgaacgta    23580
tgcagcggcg gcggcggcac catccaagta actcaagcga gcacggttga acaatacttg    23640
aaccttttg tcccaatcca ctttagaaaa ctaagaaatt catatcggag aaaggtcgaa    23700
gaatggtttg agaaaagact cggtagcttc cccaccaagt ctcacaatag aaacattatg    23760
aaaatattta cccttcataa ccctaatatg acccttcttc gcagtcgact tctcaaagac    23820
gacgtggctt ggtttctagg gtcgttcttc ggcatcaccc tcaaaatcaa agtcctcgct    23880
atcctcagaa tcgttgacat tccgaccaat attttataag taatcttcgg aatattactc    23940
ttctccatag cctcctggaa cccagcaagc gcaaactctt cactcttgct cccctcgacc    24000
atcatagcca aaccaaata accaatgaat ctaaaacggt cacaattgat aataataacc    24060
ttcggttta aagcgctagc tattctagca acaaaatagg tgaatggtgt gataattgcg    24120
catacgattt tcattctatt tataataaaa gccaggccag ggtcgaataa aaaatataaa    24180
actaccactg caaaatgggc ctcgcatttc aagtatctcg atgattagct taaggaaggt    24240
gttttttcaa ccttcgacat aaggccttcg ttcatttctc agtttgagtt cgttgcaaga    24300
aaacaaacta atactgggag gggctagttt tggggccttc atcatttgaa ggttctcaaa    24360
acactaatta accattgttt catgatacat ctctaaaagt gttacaggtg cttcagtaaa    24420
aaccaccttc gaaataaatc gagcaacgac gaaggtacat ttctactagc ggataaaact    24480
```

```
ggtcttgggc cgaggcagca tacaaagaag cttcgcctgt gcgcgcaagt ggcagaggtg  24540
ttagccgaag tcgataactt tggcaacaac agaagaggat ggagaaaata cattattatc  24600
ctgatggtat ttgtaaacaa tgtttgtaaa accttggggc atgattataa ttctatataa  24660
agacagttca ttttcctata aataggtgag cagtaccctg cataaggcat cttttttgagg 24720 ggtgatcact tcgtttaact tagcttacag agaacctttg taccatcttg tgtgtggagc  24780
tgaaggtatg cttgtacacc tttatcaaga gagatagagt aaattgctaa ggcatataag  24840
atgagttgaa tatgaagtta cactttg                                      24867
```

MAIZE EVENT DP-915635-4 AND METHODS FOR DETECTION THEREOF

REFERENCE TO SEQUENCE LISTING SUBMITTED ELECTRONICALLY

The official copy of the sequence listing is submitted electronically via EFS-Web as an ASCII formatted sequence listing with a file named "8425_SeqList.txt" created on Nov. 13, 2020 and having a size of 202 kilobytes and is filed concurrently with the specification. The sequence listing contained in this ASCII formatted document is part of the specification and is herein incorporated by reference in its entirety.

FIELD

Embodiments disclosed herein relate to the field of plant molecular biology, including to DNA constructs for conferring insect resistance to a plant. Embodiments disclosed herein also include insect resistant corn plant containing event DP-915635-4 and assays for detecting the presence of event DP-915635-4 in a sample and compositions thereof.

BACKGROUND

Corn is an important crop and is a primary food source in many areas of the world. Damage caused by insect pests is a major factor in the loss of the world's corn crops, despite the use of protective measures such as chemical pesticides. In view of this, insect resistance has been genetically engineered into crops such as corn in order to control insect damage and to reduce the need for traditional chemical pesticides. One group of genes which have been utilized for the production of transgenic insect resistant crops is the delta-endotoxin group from *Bacillus thuringiensis* (Bt). Delta-endotoxins have been successfully expressed in crop plants such as cotton, potatoes, rice, sunflower, as well as corn, and in certain circumstances have proven to provide excellent control over insect pests. (Perlak, F. J et al. (1990) *Bio/Technology* 8:939-943; Perlak, F. J. et al. (1993) *Plant Mol. Biol.* 22:313-321; Fujimoto, H. et al. (1993) *Bio/Technology* 11:1151-1155; Tu et al. (2000) *Nature Biotechnology* 18:1101-1104; PCT publication WO 01/13731; and Bing, J. W. et al. (2000) Efficacy of Cry1F Transgenic Maize, 14$^{th}$ Biennial International Plant Resistance to Insects Workshop, Fort Collins, CO).

The expression of transgenes in plants is known to be influenced by many different factors, including the orientation and composition of the cassettes driving expression of the individual genes of interest, and the location in the plant genome, perhaps due to chromatin structure (e.g., heterochromatin) or the proximity of transcriptional regulatory elements (e.g., enhancers) close to the integration site (Weising et al. (1988) *Ann. Rev. Genet.* 22:421-477).

It would be advantageous to be able to detect the presence of a particular event in order to determine whether progeny of a sexual cross contain a transgene of interest.

It is possible to detect the presence of a transgene by a nucleic acid detection method by, e.g., a polymerase chain reaction (PCR) or DNA hybridization using nucleic acid probes. These detection methods generally focus on frequently used genetic elements, such as promoters, terminators, marker genes, etc., because for many DNA constructs, the coding region is interchangeable. As a result, such methods may not be useful for discriminating between different events, particularly those produced using the same DNA construct or very similar constructs unless the DNA sequence of the flanking DNA adjacent to the inserted heterologous DNA is known

SUMMARY

The embodiments relate to the insect resistant corn (*Zea mays*) plant event DP-915635-4, also referred to as "maize line DP-915635-4," "maize event DP-915635-4," and "DP-915635-4 maize," to the DNA plant expression construct of corn plant event DP-915635-4, and to methods and compositions for the detection of the transgene construct, flanking, and insertion (the target locus) regions in corn plant event DP-915635-4 and progeny thereof.

In one aspect compositions and methods relate to methods for producing and selecting an insect resistant monocot crop plant. Compositions include a DNA construct that when expressed in plant cells and plants confers resistance to insects. In one aspect, a DNA construct, capable of introduction into and replication in a host cell, is provided that when expressed in plant cells and plants confers insect resistance to the plant cells and plants. Maize event DP-915635-4 was produced by *Agrobacterium*-mediated transformation with plasmid PHP83175. As described herein, these events include the IPD079Ea (polynucleotide SEQ ID NO: 4 and amino acid SEQ ID NO: 5) cassette (Table 1), which confers resistance to certain *Coleopteran* plant pests. The insect control components have demonstrated efficacy against *Coleopteran* insect species, particularly western corn rootworm (WCR). In some embodiments, a polynucleotide encoding an IPD079Ea polypeptide comprises a sequence having at least 95%, 96%, 97%, 98%, or 99% sequence identity to SEQ ID NO: 4. In some embodiments, an IPD079EA polypeptide comprises a sequence having 95%, 96%, 97%, 98%, or 99% sequence identity to SEQ ID NO: 5.

According to some embodiments, compositions and methods are provided for identifying a novel corn plant designated DP-915635-4 (ATCC Deposit Number PTA-126746). The methods are based on primers or probes which specifically recognize 5' and/or 3' flanking sequence of DP-915635-4. DNA molecules are provided that comprise primer sequences that when utilized in a PCR reaction will produce amplicons unique to the transgenic event DP-915635-4. In one embodiment, the corn plant and seed comprising these molecules is contemplated. Further, kits utilizing these primer sequences for the identification of the DP-915635-4 event are provided.

Some embodiments relate to specific flanking sequences of DP-915635-4 as described herein, which can be used to develop identification methods for DP-915635-4 in biological samples. More particularly, the disclosure relates to 5' and/or 3' flanking regions of DP-915635-4, which can be used for the development of specific primers and probes. Further embodiments relate to identification methods for the presence of DP-915635-4 in biological samples based on the use of such specific primers or probes.

According to some embodiments, methods of detecting the presence of DNA corresponding to the corn event DP-915635-4 in a sample are provided. Such methods comprise: (a) contacting the sample comprising DNA with a DNA primer set, that when used in a nucleic acid amplification reaction with genomic DNA extracted from corn comprising event DP-915635-4 produces an amplicon that is diagnostic for corn event DP-915635-4, respectively; (b) performing a nucleic acid amplification reaction, thereby producing the amplicon; and (c) detecting the amplicon. In some aspects, the primer set comprises SEQ ID NOs: 6 and 7, and optionally a probe comprising SEQ ID NO: 8.

According to some embodiments, methods of detecting the presence of a DNA molecule corresponding to the DP-915635-4 event in a sample comprise: (a) contacting the sample comprising DNA extracted from a corn plant with a DNA probe molecule that hybridizes under stringent hybridization conditions with DNA extracted from corn event DP-915635-4 and does not hybridize under the stringent hybridization conditions with a control corn plant DNA; (b) subjecting the sample and probe to stringent hybridization conditions; and (c) detecting hybridization of the probe to the DNA extracted from corn event DP-915635-4. More specifically, a method for detecting the presence of a DNA molecule corresponding to the DP-915635-4 event in a sample consist of (a) contacting the sample comprising DNA extracted from a corn plant with a DNA probe molecule that comprises sequences that are unique to the event, e.g. junction sequences, wherein said DNA probe molecule hybridizes under stringent hybridization conditions with DNA extracted from corn event DP-915635-4 and does not hybridize under the stringent hybridization conditions with a control corn plant DNA; (b) subjecting the sample and probe to stringent hybridization conditions; and (c) detecting hybridization of the probe to the DNA.

In addition, a kit and methods for identifying event DP-915635-4 in a biological sample which detects a DP-915635-4 specific region are provided.

DNA molecules are provided that comprise at least one junction sequence of DP-915635-4; wherein a junction sequence spans the junction located between heterologous DNA inserted into the genome and the DNA from the maize cell flanking the insertion site and may be diagnostic for the DP-915635-4 event.

According to some embodiments, methods of producing an insect resistant corn plant comprise the steps of: (a) sexually crossing a first parental corn line comprising the expression cassettes disclosed herein, which confer resistance to insects, and a second parental corn line that lacks such expression cassettes, thereby producing a plurality of progeny plants; and (b) selecting a progeny plant that is insect resistant. Such methods may optionally comprise the further step of back-crossing the progeny plant to the second parental corn line to produce a true-breeding corn plant that is insect resistant.

Some embodiments provide a method of producing a corn plant that is resistant to insects comprising transforming a corn cell with the DNA construct PHP74643, growing the transformed corn cell into a corn plant, selecting the corn plant that shows resistance to insects, and further growing the corn plant into a fertile corn plant. The fertile corn plant can be self-pollinated or crossed with compatible corn varieties to produce insect resistant progeny.

Some embodiments further relate to a DNA detection kit for identifying maize event DP-915635-4 in biological samples. The kit comprises a first primer which specifically recognizes the 5' or 3' flanking region of DP-915635-4, and a second primer which specifically recognizes a sequence within the non-native target locus DNA of DP-915635-4, respectively, or within the flanking DNA, for use in a PCR identification protocol. A further embodiment relates to a kit for identifying event DP-915635-4 in biological samples, which kit comprises a specific probe having a sequence which corresponds or is complementary to, a sequence having between about 80% and 100% sequence identity with a specific region of event DP-915635-4. The sequence of the probe corresponds to a specific region comprising part of the 5' or 3' flanking region of event DP-915635-4. In some embodiments, the first or second primer comprises any one of SEQ ID NOs: 6-7, 9-10, 12-13, 15-16, or 18-19.

The methods and kits encompassed by the embodiments disclosed herein can be used for different purposes such as, but not limited to the following: to identify event DP-915635-4 in plants, plant material or in products such as, but not limited to, food or feed products (fresh or processed) comprising, or derived from plant material; additionally or alternatively, the methods and kits can be used to identify transgenic plant material for purposes of segregation between transgenic and non-transgenic material; additionally or alternatively, the methods and kits can be used to determine the quality of plant material comprising maize event DP-915635-4. The kits may also contain the reagents and materials necessary for the performance of the detection method.

A further embodiment relates to the DP-915635-4 maize plant or its parts, including, but not limited to, pollen, ovules, vegetative cells, the nuclei of pollen cells, and the nuclei of egg cells of the corn plant DP-915635-4 and the progeny derived thereof. In another embodiment, the DNA primer molecules targeting the maize plant and seed of DP-915635-4 provide a specific amplicon product

DESCRIPTION OF THE DRAWINGS

FIG. 5 is a table showing hybrid performance of event DP-915635-4 compared to a base entry for non-yield agronomic traits.

FIG. 6 is a table showing inbred performance of event DP-915635-4 compared to a base entry for all agronomic traits.

DETAILED DESCRIPTION

Figure 1:
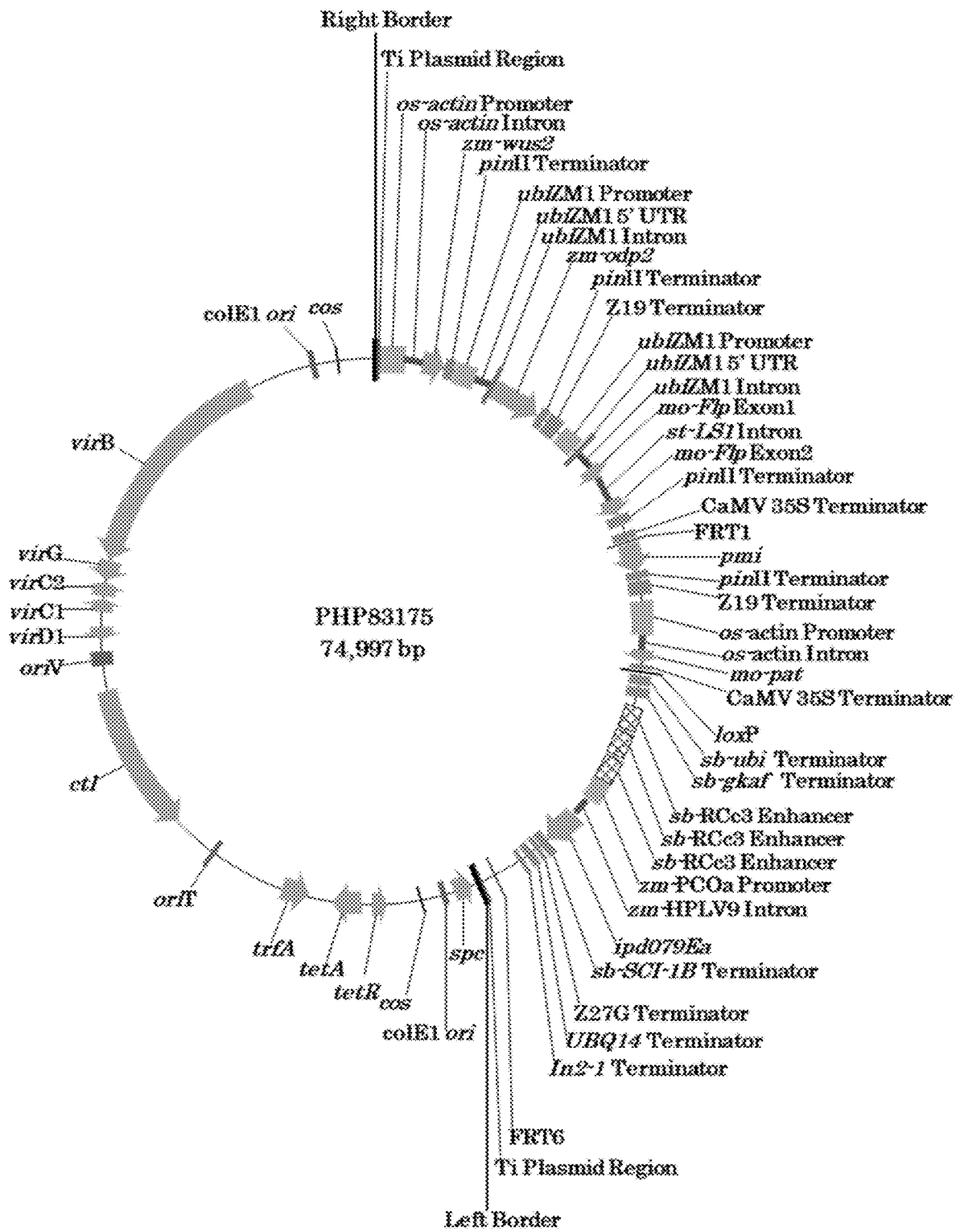
FIG. 1. shows a schematic diagram of plasmid PHP83175 with genetic elements indicated. Plasmid size is 74,997 bp (SEQ ID NO: 1).

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof, and so forth. All technical and scientific terms used herein have the same meaning as commonly understood to one of ordinary skill in the art to which this disclosure belongs unless clearly indicated otherwise.

Compositions of this disclosure include seed deposited as ATCC Patent Deposit No. PTA-126746 and plants, plant cells, and seed derived therefrom. Applicant(s) deposited at least 2500 seeds of maize event DP-915635-4 (Patent Deposit No. PTA-126746) with the American Type Culture Collection (ATCC), Manassas, VA 20110-2209 USA, on Mar. 27, 2020. These deposits will be maintained under the terms of the Budapest Treaty on the International Recognition of the Deposit of Microorganisms for the Purposes of Patent Procedure. The seeds deposited with the ATCC on Mar. 27, 2020 were taken from the deposit maintained by Pioneer Hi-Bred International, Inc., 7250 NW 62$^{nd}$ Avenue, Johnston, Iowa 50131-1000. Access to this deposit will be available during the pendency of the application to the Commissioner of Patents and Trademarks and persons determined by the Commissioner to be entitled thereto upon request. Upon allowance of any claims in the application, the Applicant(s) will make available to the public, pursuant to 37 C.F.R. § 1.808, sample(s) of the deposit of at least 625 seeds of hybrid maize with the American Type Culture Collection (ATCC), 10801 University Boulevard, Manassas, VA 20110-2209. This deposit of seed of maize event DP-915635-4 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant(s) have satisfied all the requirements of 37 C.F.R. §§ 1.801-1.809, including providing an indication of the viability of the sample upon deposit. Applicant(s) have no authority to waive any restrictions imposed by law on the transfer of biological material or its transportation in commerce. Applicant(s) do not waive any infringement of their rights granted under this patent or rights applicable to event DP-915635-4 under the Plant Variety Protection Act (7 USC 2321 et seq.). Unauthorized seed multiplication is prohibited. The seed may be regulated.

A first cassette contains the insecticidal protein gene, IPD079Ea, from *Ophioglossum pendulum* (international patent application publication number WO 2017023486). The expressed IPD079Ea protein in plants is effective against certain coleopteran pests. The IPD079Ea protein is 479 amino acids in length and has a molecular weight of approximately 52 kDa. Expression of the IPD079Ea gene is controlled by three copies of the enhancer region, showing root-specific activity, from the sorghum (*Sorghum bicolor*) root cortical RCc3 (sb-RCc3) gene (international patent application publication number WO 2012112411) followed by the promoter region upstream of a *Zea mays* PCO118362 mRNA sequence (zm PCOa) identified as having root-specific activity (international patent application publication number WO 2017222821) and the intron region from the *Zea mays* ortholog of a rice (*Oryza sativa*) hypothetical protein (zm-HPLV9) gene, a predicted *Zea mays* calmodulin 5 gene (Phytozome gene ID Zm00008a029682; international patent application publication number WO 2016109157). The terminator for the IPD079Ea gene is the terminator region from the sorghum (*Sorghum bicolor*) subtilisin-chymotrypsin inhibitor 1B (sb-SCI-1B) gene (international patent application publication number WO 2018102131). Three additional terminators are present to prevent transcriptional interference: the terminator region from the maize W64 line 27-kDa gamma zein (Z27G) gene (Das et al., 1991; Liu et al., 2016), the terminator region from the *Arabidopsis thaliana* ubiquitin 14 (UBQ14) gene (Callis et al., 1995), and the terminator region from the maize In2-1 gene (Hershey and Stoner, 1991).

A second gene cassette (mo pat gene cassette) contains the phosphinothricin acetyl transferase gene (mo-pat) from *Streptomyces viridochromogenes* (Wohlleben et al., 1988). The mo pat gene expresses the phosphinothricin acetyl transferase (PAT) enzyme that confers tolerance to phosphinothricin. The PAT protein is 183 amino acids in length and has a molecular weight of approximately 21 kDa. Expression of the mo-pat gene is controlled by the promoter and intron region of the *Oryza sativa* (rice) actin (os-actin) gene (GenBank accession CP018159), in conjunction with a third copy of the CaMV35S terminator. Two additional terminators are present to prevent transcriptional interference: the terminator regions from the *Sorghum bicolor* (sorghum) ubiquitin (sb-ubi) gene (Phytozome gene ID Sobic.004G049900.1) and γ-kafarin (sb-gkaf) gene (de Freitas et al., 1994), respectively.

A third gene cassette (pmi gene cassette) contains the phosphomannose isomerase (pmi) gene from *Escherichia coli* (Negrotto et al., 2000). Expression of the PMI protein in plants serves as a selectable marker which allows plant tissue growth with mannose as the carbon source. The PMI protein is 391 amino acids in length and has a molecular weight of approximately 43 kDa. As present in the T-DNA region of PHP74643, the pmi gene lacks a promoter, but its location next to the flippase recombination target site, FRT1, allows post-recombination expression by an appropriately-placed promoter. The terminator for the pmi gene is a fourth copy of the pinII terminator. An additional Z19 terminator present is intended to prevent transcriptional interference between cassettes.

As used herein, the term "corn" means *Zea mays* or maize and includes all plant varieties that can be bred with corn, including wild maize species.

As used herein, the terms "insect resistant" and "impacting insect pests" refers to effecting changes in insect feeding, growth, and/or behavior at any stage of development, including but not limited to: killing the insect; retarding growth; reducing reproductive capability; inhibiting feeding; and the like.

As used herein, the terms "pesticidal activity" and "insecticidal activity" are used synonymously to refer to activity of an organism or a substance (such as, for example, a protein) that can be measured by numerous parameters including, but not limited to, pest mortality, pest weight loss, pest attraction, pest repellency, and other behavioral and physical changes of a pest after feeding on and/or exposure to the organism or substance for an appropriate length of time. For example, "pesticidal proteins" are proteins that display pesticidal activity by themselves or in combination with other proteins.

As used herein, "insert DNA" refers to the heterologous DNA within the expression cassettes used to transform the plant material while "flanking DNA" can exist of either genomic DNA naturally present in an organism such as a plant, or foreign (heterologous) DNA introduced via the transformation process which is extraneous to the original insert DNA molecule, e.g. fragments associated with the transformation event. A "flanking region" or "flanking sequence" as used herein refers to a sequence of at least 10 bp (in some narrower embodiments, at least 20 bp, at least 50 bp, and up to at least 5000 bp), which is located either immediately upstream of and contiguous with and/or immediately downstream of and contiguous with the original non-native insert DNA molecule. Transformation procedures of the foreign DNA may result in transformants containing different flanking regions characteristic and unique for each transformant. When recombinant DNA is introduced into a plant through traditional crossing, its flanking regions will generally not be changed. It may be possible for single nucleotide changes to occur in the flanking regions through generations of plant breeding and traditional crossing. Transformants will also contain unique junctions between a piece of heterologous insert DNA and genomic DNA, or two (2) pieces of genomic DNA, or two (2) pieces of heterologous DNA. A "junction" is a point where two (2) specific DNA fragments join. For example, a junction exists where insert DNA joins flanking DNA. A junction point also exists in a transformed organism where two (2) DNA fragments join together in a manner that is modified from that found in the native organism. "Junction DNA" refers to DNA that comprises a junction point. Junction sequences set forth in this disclosure include a junction point located between the maize genomic DNA and the 5' end of the insert, which range from at least −5 to +5 nucleotides of the junction point (SEQ ID NO: 26), from at least −10 to +10 nucleotides of the junction point (SEQ ID NO: 27), and from at least −25 to +25 nucleotides of the junction point (SEQ ID NO: 28); and a junction point located between the 3' end of the insert and maize genomic DNA, which range from at least −5 to +5 nucleotides of the junction point (SEQ ID NO: 29), from at least −10 to +10 nucleotides of the junction point (SEQ ID NO: 30), and from at least −25 to +25 nucleotides of the junction point (SEQ ID NO: 31). Junction sequences set forth in this disclosure also include a junction point located between the target locus and the 5' end of the insert. In some embodiments, SEQ ID NOs: 8 or 21 for DP-915635-4 represent the junction point located between the target locus and the 5' end of the insert. The complete insert with flanking regions is represented in SEQ ID NO: 3. In some embodiments, the insert and flanking regions comprise a polynucleotide having at least 95%, 96%, 97%, 98%, or 99% sequence identity compared to SEQ ID NO: 3.

As used herein, "heterologous" in reference to a nucleic acid sequence is a nucleic acid sequence that originates from a different non-sexually compatible species, or, if from the same species, is substantially modified from its native form in composition and/or genomic locus by deliberate human intervention. For example, a promoter operably linked to a heterologous nucleotide sequence can be from a species different from that from which the nucleotide sequence was derived, or, if from the same species, the promoter is not naturally found operably linked to the nucleotide sequence. A heterologous protein may originate from a foreign species, or, if from the same species, is substantially modified from its original form by deliberate human intervention.

The term "regulatory element" refers to a nucleic acid molecule having gene regulatory activity, i.e. one that has the ability to affect the transcriptional and/or translational expression pattern of an operably linked transcribable polynucleotide. The term "gene regulatory activity" thus refers to the ability to affect the expression of an operably linked transcribable polynucleotide molecule by affecting the transcription and/or translation of that operably linked transcribable polynucleotide molecule. Gene regulatory activity may be positive and/or negative and the effect may be characterized by its temporal, spatial, developmental, tissue, environmental, physiological, pathological, cell cycle, and/or chemically responsive qualities as well as by quantitative or qualitative indications.

"Promoter" refers to a nucleotide sequence capable of controlling the expression of a coding sequence or functional RNA. In general, a coding sequence is located 3' to a promoter sequence. The promoter sequence comprises proximal and more distal upstream elements, the latter elements are often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene or be composed of different elements derived from different promoters found in nature, or even comprise synthetic nucleotide segments. It is understood by those skilled in the art that different regulatory elements may direct the expression of a gene in different tissues or cell types, or at different stages of development, or in response to different environmental conditions. Promoters that cause a nucleic acid fragment to be expressed in most cell types at most times are commonly referred to as "constitutive promoters". It is further recognized that since in most cases the exact boundaries of regulatory sequences have not been completely defined, nucleic acid fragments of different lengths may have identical or similar promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect numerous parameters including, processing of the primary transcript to mRNA, mRNA stability and/or translation efficiency.

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

A DNA construct is an assembly of DNA molecules linked together that provide one or more expression cassettes. The DNA construct may be a plasmid that is enabled for self-replication in a bacterial cell and contains various endonuclease enzyme restriction sites that are useful for introducing DNA molecules that provide functional genetic elements, i.e., promoters, introns, leaders, coding sequences, 3' termination regions, among others; or a DNA construct may be a linear assembly of DNA molecules, such as an expression cassette. The expression cassette contained within a DNA construct comprises the necessary genetic elements to provide transcription of a messenger RNA. The expression cassette can be designed to express in prokaryotic cells or eukaryotic cells. Expression cassettes of the embodiments are designed to express in plant cells.

The DNA molecules disclosed herein are provided in expression cassettes for expression in an organism of interest. The cassette includes 5' and 3' regulatory sequences operably linked to a coding sequence. "Operably linked" means that the nucleic acid sequences being linked are contiguous and, where necessary to join two protein coding regions, contiguous and in the same reading frame. Operably linked is intended to indicate a functional linkage between a promoter and a second sequence, wherein the promoter sequence initiates and mediates transcription of the DNA sequence corresponding to the second sequence. The cassette may additionally contain at least one additional gene to be co-transformed into the organism. Alternatively, the additional gene(s) can be provided on multiple expression cassettes or multiple DNA constructs.

The expression cassette may include in the 5' to 3' direction of transcription: a transcriptional and translational initiation region, a coding region, and a transcriptional and translational termination region functional in the organism serving as a host. The transcriptional initiation region (e.g., the promoter) may be native or analogous, or foreign or heterologous to the host organism. Additionally, the promoter may be the natural sequence or alternatively a synthetic sequence. The expression cassettes may additionally contain 5' leader sequences in the expression cassette construct. Such leader sequences can act to enhance translation.

It is to be understood that as used herein the term "transgenic" generally includes any cell, cell line, callus, tissue, plant part, or plant, the genotype of which has been altered by the presence of a heterologous nucleic acid including those initially so altered as well as those created by sexual crosses or asexual propagation from the initial transgenic and retains such heterologous nucleic acids.

A transgenic "event" is produced by transformation of plant cells with a heterologous DNA construct(s), including a nucleic acid expression cassette that comprises a transgene of interest, the regeneration of a population of plants resulting from the insertion of the transgene into the genome of the plant, and selection of a particular plant characterized by insertion into a particular genome location. An event is characterized phenotypically by the expression of the transgene. At the genetic level, an event is part of the genetic makeup of a plant. The term "event" also refers to progeny produced by a sexual outcross between the transformant and another variety, wherein the progeny includes the heterologous DNA. After back-crossing to a recurrent parent, the inserted DNA and the linked flanking genomic DNA from the transformed parent is present in the progeny of the cross at the same chromosomal location. A progeny plant may contain sequence changes to the insert arising as a result of conventional breeding techniques. The term "event" also refers to DNA from the original transformant comprising the inserted DNA and flanking sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

An insect resistant DP-915635-4 corn plant may be bred by first sexually crossing a first parental corn plant having the transgenic DP-915635-4 event plant and progeny thereof derived from transformation with the expression cassettes of the embodiments that confers insect resistance, and a second parental corn plant that lacks such expression cassettes, thereby producing a plurality of first progeny plants; and then selecting a first progeny plant that is resistant to insects; and selfing the first progeny plant, thereby producing a plurality of second progeny plants; and then selecting from the second progeny plants an insect resistant plant. These steps can further include the back-crossing of the first insect resistant progeny plant or the second insect resistant progeny plant to the second parental corn plant or a third parental corn plant, thereby producing a corn plant that is resistant to insects. The term "selfing" refers to self-pollination, including the union of gametes and/or nuclei from the same organism.

As used herein, the term "plant" includes reference to whole plants, parts of plants, plant organs (e.g., leaves, stems, roots, etc.), seeds, plant cells, and progeny of same. In some embodiments, parts of transgenic plants comprise, for example, plant cells, protoplasts, tissues, callus, embryos as well as flowers, stems, fruits, leaves, and roots originating in transgenic plants or their progeny previously transformed with a DNA molecule disclosed herein, and therefore consisting at least in part of transgenic cells.

As used herein, the term "plant cell" includes, without limitation, seeds, suspension cultures, embryos, meristematic regions, callus tissue, leaves, roots, shoots, gametophytes, sporophytes, pollen, and microspores. The class of plants that may be used is generally as broad as the class of higher plants amenable to transformation techniques, including both monocotyledonous and dicotyledonous plants.

"Transformation" refers to the transfer of a nucleic acid fragment into the genome of a host organism, resulting in genetically stable inheritance. Host plants containing the transformed nucleic acid fragments are referred to as "transgenic" plants.

As used herein, the term "progeny," in the context of event DP-915635-4, denotes an offspring of any generation of a parent plant which comprises corn event DP-915635-4.

Isolated polynucleotides disclosed herein may be incorporated into recombinant constructs, typically DNA constructs, which are capable of introduction into and replication in a host cell. Such a construct may be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., (1985; Supp. 1987) *Cloning Vectors: A Laboratory Manual*, Weissbach and Weissbach (1989) *Methods for Plant Molecular Biology*, (Academic Press, New York); and Flevin et al., (1990) *Plant Molecular Biology Manual*, (Kluwer Academic Publishers). Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

During the process of introducing an insert into the genome of plant cells, it is not uncommon for some deletions or other alterations of the insert and/or genomic flanking sequences to occur. Thus, the relevant segment of the plasmid sequence provided herein might comprise some minor variations. The same is possible for the flanking sequences provided herein. Thus, a plant comprising a polynucleotide having some range of identity with the subject flanking and/or insert sequences is within the scope of the subject disclosure. Identity to the sequence of the present disclosure may be a polynucleotide sequence having at least 65% sequence identity, at least 70% sequence identity, at least 75% sequence identity at least 80% identity, or at least 85% 86%, 87%, 88%, 89%, 90%, 91%, 92%, 93%, 94%, 95%, 96%, 97%, 98%, 99% sequence identity with a sequence exemplified or described herein. Hybridization and hybridization conditions as provided herein can also be used to define such plants and polynucleotide sequences of the subject disclosure. A sequence comprising the flanking sequences plus the full insert sequence can be confirmed with reference to the deposited seed.

In some embodiments, two different transgenic plants can also be crossed to produce offspring that contain two independently segregating added, exogenous genes. Selfing of appropriate progeny can produce plants that are homozygous for both added, exogenous genes. Back-crossing to a parental plant and out-crossing with a non-transgenic plant are also contemplated, as is vegetative propagation.

A "probe" is an isolated nucleic acid to which is attached a conventional, synthetic detectable label or reporter molecule, e.g., a radioactive isotope, ligand, chemiluminescent agent, or enzyme. Such a probe is complementary to a strand of a target nucleic acid, for example, to a strand of isolated DNA from corn event DP-915635-4 whether from a corn plant or from a sample that includes DNA from the event. Probes may include not only deoxyribonucleic or ribonucleic acids but also polyamides and other modified nucleotides that bind specifically to a target DNA sequence and can be used to detect the presence of that target DNA sequence.

"Primers" are isolated nucleic acids that anneal to a complementary target DNA strand by nucleic acid hybridization to form a hybrid between the primer and the target DNA strand, then extended along the target DNA strand by a polymerase, e.g., a DNA polymerase. Primer pairs refer to their use for amplification of a target nucleic acid sequence, e.g., by PCR or other conventional nucleic-acid amplification methods. "PCR" or "polymerase chain reaction" is a technique used for the amplification of specific DNA segments (see, U.S. Pat. Nos. 4,683,195 and 4,800,159; herein incorporated by reference).

Probes and primers are of sufficient nucleotide length to bind to the target DNA sequence specifically in the hybridization conditions or reaction conditions determined by the operator. This length may be of any length that is of sufficient length to be useful in a detection method of choice. Generally, 11 nucleotides or more in length, 18 nucleotides or more, and 22 nucleotides or more, are used. Such probes and primers hybridize specifically to a target sequence under high stringency hybridization conditions. Probes and primers according to embodiments may have complete DNA sequence similarity of contiguous nucleotides with the target sequence, although probes differing from the target DNA sequence and that retain the ability to hybridize to target DNA sequences may be designed by conventional methods. Probes can be used as primers, but are generally designed to bind to the target DNA or RNA and are not used in an amplification process.

Specific primers may be used to amplify an integration fragment to produce an amplicon that can be used as a "specific probe" for identifying event DP-915635-4 in biological samples. When the probe is hybridized with the nucleic acids of a biological sample under conditions which allow for the binding of the probe to the sample, this binding can be detected and thus allow for an indication of the presence of event DP-915635-4 in the biological sample. In an embodiment of the disclosure, the specific probe is a sequence which, under appropriate conditions, hybridizes specifically to a region within the 5' or 3' flanking region of the event and also comprises a part of the foreign DNA contiguous therewith. The specific probe may comprise a sequence of at least 80%, from 80 and 85%, from 85 and 90%, from 90 and 95%, and from 95 and 100% identical (or complementary) to a specific region of the event.

Methods for preparing and using probes and primers are described, for example, in Sambrook et al., *Molecular Cloning: A Laboratory Manual*, $2^{nd}$ ed., vol. 1-3, Cold Spring Harbor Laboratory Press, Cold Spring Harbor, N.Y. 1989 (hereinafter, "Sambrook et al., 1989"); Ausubel et al. eds., *Current Protocols in Molecular Biology*, Greene Publishing and Wiley-Interscience, New York, 1995 (with periodic updates) (hereinafter, "Ausubel et al., 1995"); and Innis et al., *PCR Protocols: A Guide to Methods and Applications*, Academic Press: San Diego, 1990. PCR primer pairs can be derived from a known sequence, for example, by using computer programs intended for that purpose such as the PCR primer analysis tool in Vector NTI version 6 (Informax Inc., Bethesda MD); PrimerSelect (DNASTAR Inc., Madison, WI); and Primer (Version 0.5®, 1991, Whitehead Institute for Biomedical Research, Cambridge, Mass.). Additionally, the sequence can be visually scanned and primers manually identified using guidelines known to one of skill in the art.

A "kit" as used herein refers to a set of reagents, and optionally instructions, for the purpose of performing method embodiments of the disclosure, more particularly, the identification of event DP-915635-4 in biological samples. A kit may be used, and its components can be specifically adjusted, for purposes of quality control (e.g. purity of seed lots), detection of event DP-915635-4 in plant material, or material comprising or derived from plant material, such as but not limited to food or feed products. "Plant material" as used herein refers to material which is obtained or derived from a plant.

Primers and probes based on the flanking DNA and insert sequences disclosed herein can be used to confirm (and, if necessary, to correct) the disclosed sequences by conventional methods, e.g., by re-cloning and sequencing such sequences. The nucleic acid probes and primers hybridize under stringent conditions to a target DNA sequence. Any conventional nucleic acid hybridization or amplification method may be used to identify the presence of DNA from a transgenic event in a sample.

A nucleic acid molecule is said to be the "complement" of another nucleic acid molecule if they exhibit complete complementarity or minimal complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Haymes et al., In: *Nucleic Acid Hybridization, a Practical Approach*, IRL Press, Washington, D.C. (1985), departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

In hybridization reactions, specificity is typically the function of post-hybridization washes, the critical factors being the ionic strength and temperature of the final wash solution. The thermal melting point ($T_m$) is the temperature (under defined ionic strength and pH) at which 50% of a complementary target sequence hybridizes to a perfectly matched probe. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, in some embodiments, other stringency conditions can be applied, including severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$.

Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), a user may choose to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) and Sambrook et al. (1989).

In some embodiments, a complementary sequence has the same length as the nucleic acid molecule to which it hybridizes. In some embodiments, the complementary sequence is 1, 2, 3, 4, 5, 6, 7, 8, 9, or 10 nucleotides longer or shorter than the nucleic acid molecule to which it hybridizes. In some embodiments, the complementary sequence is 1%, 2%, 3%, 4%, or 5% longer or shorter than the nucleic acid molecule to which it hybridizes. In some embodiments, a complementary sequence is complementary on a nucleotide-for-nucleotide basis, meaning that there are no mismatched nucleotides (each A pairs with a T and each G pairs with a C). In some embodiments, a complementary sequence comprises 1, 2, 3, 4, 5, 6, 7, 8, 9, 10 or less mismatches. In some embodiments, the complementary sequence comprises 1%, 2%, 3%, 4%, 5%, 6%, 7%, 8%, 9%, or 10% or less mismatches.

"Percent (%) sequence identity" with respect to a reference sequence (subject) is determined as the percentage of amino acid residues or nucleotides in a candidate sequence (query) that are identical with the respective amino acid residues or nucleotides in the reference sequence, after aligning the sequences and introducing gaps, if necessary, to achieve the maximum percent sequence identity, and not considering any amino acid conservative substitutions as part of the sequence identity. Alignment for purposes of determining percent sequence identity can be achieved in various ways that are within the skill in the art, for instance, using publicly available computer software such as BLAST, BLAST-2. Those skilled in the art can determine appropriate parameters for aligning sequences, including any algorithms needed to achieve maximal alignment over the full length of the sequences being compared. The percent identity between the two sequences is a function of the number of identical positions shared by the sequences (e.g., percent identity of query sequence=number of identical positions between query and subject sequences/total number of positions of query sequence×100).

Regarding the amplification of a target nucleic acid sequence (e.g., by PCR) using a particular amplification primer pair, stringent conditions permit the primer pair to hybridize only to the target nucleic-acid sequence to which a primer having the corresponding wild-type sequence (or its complement) would bind and optionally to produce a unique amplification product, the amplicon, in a DNA thermal amplification reaction.

As used herein, "amplified DNA" or "amplicon" refers to the product of nucleic acid amplification of a target nucleic acid sequence that is part of a nucleic acid template. For example, to determine whether a corn plant resulting from a sexual cross contains transgenic event genomic DNA from the corn plant disclosed herein, DNA extracted from a tissue sample of a corn plant may be subjected to a nucleic acid amplification method using a DNA primer pair that includes a first primer derived from flanking sequence adjacent to the insertion site of inserted heterologous DNA, and a second primer derived from the inserted heterologous DNA to produce an amplicon that is diagnostic for the presence of the event DNA. Alternatively, the second primer may be derived from the flanking sequence. The amplicon is of a length and has a sequence that is also diagnostic for the event. The amplicon may range in length from the combined length of the primer pairs plus one nucleotide base pair to any length of amplicon producible by a DNA amplification protocol. Alternatively, primer pairs can be derived from flanking sequence on both sides of the inserted DNA so as to produce an amplicon that includes the entire insert nucleotide sequence of the PHP74643 expression construct as well as a portion of the sequence flanking the transgenic insert. A member of a primer pair derived from the flanking sequence may be located a distance from the inserted DNA sequence, this distance can range from one nucleotide base pair up to the limits of the amplification reaction. The use of the term "amplicon" specifically excludes primer dimers that may be formed in the DNA thermal amplification reaction.

Nucleic acid amplification can be accomplished by any of the various nucleic acid amplification methods known in the art, including PCR. A variety of amplification methods are known in the art and are described, inter alia, in U.S. Pat. Nos. 4,683,195 and 4,683,202 and in Innis et al., (1990) supra. PCR amplification methods have been developed to amplify up to 22 Kb of genomic DNA and up to 42 Kb of bacteriophage DNA (Cheng et al., *Proc. Natl. Acad. Sci. USA* 91:5695-5699, 1994). These methods as well as other methods known in the art of DNA amplification may be used in the practice of the embodiments of the present disclosure. It is understood that a number of parameters in a specific PCR protocol may need to be adjusted to specific laboratory conditions and may be slightly modified and yet allow for the collection of similar results. These adjustments will be apparent to a person skilled in the art.

The amplicon produced by these methods may be detected by a plurality of techniques, including, but not limited to, Genetic Bit Analysis (Nikiforov, et al. *Nucleic Acid Res.* 22:4167-4175, 1994) where a DNA oligonucleotide is designed which overlaps both the adjacent flanking DNA sequence and the inserted DNA sequence. The oligonucleotide is immobilized in wells of a microwell plate.

Following PCR of the region of interest (for example, using one primer in the inserted sequence and one in the adjacent flanking sequence) a single-stranded PCR product can be hybridized to the immobilized oligonucleotide and serve as a template for a single base extension reaction using a DNA polymerase and labeled ddNTPs specific for the expected next base. Readout may be fluorescent or ELISA-based. A signal indicates presence of the insert/flanking sequence due to successful amplification, hybridization, and single base extension.

Another detection method is the pyrosequencing technique as described by Winge (2000) *Innov. Pharma. Tech.* 00:18-24. In this method an oligonucleotide is designed that overlaps the adjacent DNA and insert DNA junction. The oligonucleotide is hybridized to a single-stranded PCR product from the region of interest (for example, one primer in the inserted sequence and one in the flanking sequence) and incubated in the presence of a DNA polymerase, ATP, sulfurylase, luciferase, apyrase, adenosine 5' phosphosulfate and luciferin. dNTPs are added individually and the incorporation results in a light signal which is measured. A light signal indicates the presence of the transgene insert/flanking sequence due to successful amplification, hybridization, and single or multi-base extension.

Fluorescence polarization as described by Chen et al., (1999) *Genome Res.* 9:492-498 is also a method that can be used to detect an amplicon. Using this method an oligonucleotide is designed which overlaps the flanking and inserted DNA junction. The oligonucleotide is hybridized to a single-stranded PCR product from the region of interest (for example, one primer in the inserted DNA and one in the flanking DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

Quantitative PCR (qPCR) is described as a method of detecting and quantifying the presence of a DNA sequence and is fully understood in the instructions provided by commercially available manufacturers. Briefly, in one such qPCR method, a FRET oligonucleotide probe is designed which overlaps the flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Molecular beacons have been described for use in sequence detection as described in Tyangi et al. (1996) *Nature Biotech.* 14:303-308. Briefly, a FRET oligonucleotide probe is designed that overlaps the flanking and insert DNA junction. The unique structure of the FRET probe results in it containing secondary structure that keeps the fluorescent and quenching moieties in close proximity. The FRET probe and PCR primers (for example, one primer in the insert DNA sequence and one in the flanking sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking/transgene insert sequence due to successful amplification and hybridization.

A hybridization reaction using a probe specific to a sequence found within the amplicon is yet another method used to detect the amplicon produced by a PCR reaction.

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera.

Of interest are larvae and adults of the order Coleoptera including weevils from the families Anthribidae, Bruchidae, and Curculionidae including, but not limited to: *Anthonomus grandis* Boheman (boll weevil); *Cylindrocopturus adspersus* LeConte (sunflower stem weevil); *Diaprepes abbreviatus* Linnaeus (*Diaprepes* root weevil); *Hypera punctata* Fabricius (clover leaf weevil); *Lissorhoptrus oryzophilus* Kuschel (rice water weevil); *Metamasius hemipterus hemipterus* Linnaeus (West Indian cane weevil); *M. hemipterus sericeus* Olivier (silky cane weevil); *Sitophilus granarius* Linnaeus (granary weevil); *S. oryzae* Linnaeus (rice weevil); *Smicronyx fulvus* LeConte (red sunflower seed weevil); *S. sordidus* LeConte (gray sunflower seed weevil); *Sphenophorus maidis* Chittenden (maize billbug); *S. livis* Vaurie (sugarcane weevil); *Rhabdoscelus obscurus* Boisduval (New Guinea sugarcane weevil); flea beetles, cucumber beetles, rootworms, leaf beetles, potato beetles, and leafminers in the family Chrysomelidae including, but not limited to: *Chaetocnema ectypa* Horn (desert corn flea beetle); *C. pulicaria* Melsheimer (corn flea beetle); *Colaspis brunnea* Fabricius (grape *colaspis*); *Diabrotica barberi* Smith & Lawrence (northern corn rootworm); *D. undecimpunctata howardi* Barber (southern corn rootworm); *D. virgifera virgifera* LeConte (western corn rootworm); *Leptinotarsa decemlineata* Say (Colorado potato beetle); *Oulema melanopus* Linnaeus (cereal leaf beetle); *Phyllotreta cruciferae* Goeze (corn flea beetle); *Zygogramma exclamationis* Fabricius (sunflower beetle); beetles from the family Coccinellidae including, but not limited to: *Epilachna varivestis* Mulsant (Mexican bean beetle); chafers and other beetles from the family Scarabaeidae including, but not limited to: *Antitrogus parvulus* Britton (Childers cane grub); *Cyclocephala borealis* Arrow (northern masked chafer, white grub); *C. immaculata* Olivier (southern masked chafer, white grub); *Dermolepida albohirtum* Waterhouse (Greyback cane beetle); *Euetheola humilis rugiceps* LeConte (sugarcane beetle); *Lepidiota frenchi* Blackburn (French's cane grub); *Tomarus gibbosus* De Geer (carrot beetle); *T. subtropicus* Blatchley (sugarcane grub); *Phyllophaga crinita* Burmeister (white grub); *P. latifrons* LeConte (June beetle); *Popillia japonica* Newman (Japanese beetle); *Rhizotrogus majalis* Razoumowsky (European chafer); carpet beetles from the family Dermestidae; wireworms from the family Elateridae, *Eleodes* spp., *Melanotus* spp. including *M. communis* Gyllenhal (wireworm); *Conoderus* spp.; *Limonius* spp.; *Agriotes* spp.; *Ctenicera* spp.; *Aeolus* spp.; bark beetles from the family Scolytidae; beetles from the family Tenebrionidae; beetles from the family Cerambycidae such as, but not limited to, *Migdolus fryanus* Westwood (longhorn beetle); and beetles from the Buprestidae family including, but not limited to, *Aphanisticus cochinchinae seminulum* Obenberger (leaf-mining buprestid beetle).

In some embodiments the DP-915635-4 maize event may further comprise a stack of additional traits. Plants comprising stacks of polynucleotide sequences can be obtained by either or both of traditional breeding methods or through genetic engineering methods. These methods include, but are not limited to, breeding individual lines each comprising a polynucleotide of interest, transforming a transgenic plant comprising a gene disclosed herein with a subsequent gene and co-transformation of genes into a single plant cell. As used herein, the term "stacked" includes having the multiple traits present in the same plant (i.e., both traits are incorporated into the nuclear genome, one trait is incorporated into the nuclear genome and one trait is incorporated into the genome of a plastid or both traits are incorporated into the genome of a plastid).

In some embodiments the DP-915635-4 maize event disclosed herein, alone or stacked with one or more additional insect resistance traits can be stacked with one or more additional input traits (e.g., herbicide resistance, fungal resistance, virus resistance, stress tolerance, disease resistance, male sterility, stalk strength, and the like) or output traits (e.g., increased yield, modified starches, improved oil profile, balanced amino acids, high lysine or methionine, increased digestibility, improved fiber quality, drought resistance, and the like). Thus, the embodiments can be used to provide a complete agronomic package of improved crop quality with the ability to flexibly and cost effectively control any number of agronomic pests.

In a further embodiment, the DP-915635-4 maize event may be stacked with one or more additional Bt insecticidal toxins, including, but not limited to, a Cry3B toxin disclosed in U.S. Pat. Nos. 8,101,826, 6,551,962, 6,586,365, 6,593,273, and PCT Publication WO 2000/011185; a mCry3B toxin disclosed in U.S. Pat. Nos. 8,269,069, and 8,513,492; a mCry3A toxin disclosed in U.S. Pat. Nos. 8,269,069, 7,276,583 and 8,759,620; or a Cry34/35 toxin disclosed in U.S. Pat. Nos. 7,309,785, 7,524,810, 7,985,893, 7,939,651 and 6,548,291. In a further embodiment, the DP-915635-4 maize event may be stacked with one or more additional transgenic events containing these Bt insecticidal toxins and other *Coleopteran* active Bt insecticidal traits for example, event MON863 disclosed in U.S. Pat. No. 7,705,216; event MIR604 disclosed in U.S. Pat. No. 8,884,102; event 5307 disclosed in U.S. Pat. No. 9,133,474; event DAS-59122 disclosed in U.S. Pat. No. 7,875,429; event DP-4114 disclosed in U.S. Pat. No. 8,575,434; event MON 87411 disclosed in U.S. Pat. No. 9,441,240; event DP-23211 disclosed in International Patent Application Publication Number WO 2019/209700; and event MON88017 disclosed in U.S. Pat. No. 8,686,230 all of which are incorporated herein by reference. In some embodiments, the DP-915635-4 maize event may be stacked with MON-87429-9 (MON87429 Event); MON87403; MON95379; MON87427; MON87419; MON-00603-6 (NK603); MON-87460-4; LY038; DAS-06275-8; BT176; BT11; MIR162; GA21; MZDT09Y; SYN-05307-1; and DAS-40278-9.

In some embodiments, the disclosed compositions can be introduced into the genome of a plant using genome editing technologies, or previously introduced polynucleotides in the genome of a plant may be edited using genome editing technologies. For example, the disclosed polynucleotides can be introduced into a desired location in the genome of a plant through the use of double-stranded break technologies such as TALENs, meganucleases, zinc finger nucleases, CRISPR-Cas, and the like. For example, the disclosed polynucleotides can be introduced into a desired location in a genome using a CRISPR-Cas system, for the purpose of site-specific insertion. The desired location in a plant genome can be any desired target site for insertion, such as a genomic region amenable for breeding or may be a target site located in a genomic window with an existing trait of interest. Existing traits of interest could be either an endogenous trait or a previously introduced trait.

In some embodiments, where the disclosed polynucleotide has previously been introduced into a genome, genome editing technologies may be used to alter or modify the introduced polynucleotide sequence. Site specific modifications that can be introduced into the disclosed compositions include those produced using any method for introducing site specific modification, including, but not limited to, through the use of gene repair oligonucleotides (e.g. US Publication 2013/0019349), or through the use of double-stranded break technologies such as TALENs, meganucleases, zinc finger nucleases, CRISPR-Cas, and the like. Such technologies can be used to modify the previously introduced polynucleotide through the insertion, deletion or substitution of nucleotides within the introduced polynucleotide. Alternatively, double-stranded break technologies can be used to add additional nucleotide sequences to the introduced polynucleotide. Additional sequences that may be added include, additional expression elements, such as enhancer and promoter sequences. In another embodiment, genome editing technologies may be used to position additional insecticidally-active proteins in close proximity to the disclosed compositions disclosed herein within the genome of a plant, in order to generate molecular stacks of insecticidally-active proteins.

An "altered target site," "altered target sequence." "modified target site," and "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

In some embodiments, a corn plant comprising a DP-915635-4 event may be treated with a seed treatment. In some embodiments, the seed treatment may be a fungicide, an insecticide, or a herbicide.

The following examples are offered by way of illustration and not by way of limitation.

EXAMPLES

Example 1. Cassette Design for Transgenic Plants Containing Constructs Encoding IPD079Ea Cassette designs for IPD079Ea expression used in the molecular stacks to generate commercial track events was chosen based upon efficacy and expression in gene testing transformation experiments. A large number of different regulatory (promoters, introns) and other elements (terminators) were evaluated in gene testing experiments. The large number of different regulatory elements were used to evaluate expression patterns for yield and trait efficacy.

The genetic elements contained in the IPD079Ea gene cassette of T-DNA Region of the selected event construct, Plasmid PHP83175, are described in Table 1.

TABLE 1

Description of Genetic Elements in the T-DNA Region of Plasmid PHP83175

| | Location on T-DNA (Base Pair Position) | Genetic Element | Size (bp) | Description |
|---|---|---|---|---|
| ipd079Ea gene cassette | 20,120-20,157 | Intervening Sequence | 38 | DNA sequence used for cloning |
| | 20,158-21,738 | sb-RCc3 Enhancer | 1581 | Enhancer region, showing root-specific activity, from the *Sorghum bicolor* (sorghum) root cortical RCc3 (sb-RCc3) gene |
| | 21,739-21,744 | Intervening Sequence | 6 | DNA sequence used for cloning |
| | 21,745-23,325 | sb-RCc3 Enhancer | 1581 | Enhancer region, showing root-specific activity, from the *Sorghum bicolor* (sorghum) root corticol RCc3 (sb-RCc3) gene (WO Patent 2012112411) |
| | 23,326-23,338 | Intervening Sequence | 13 | DNA sequence used for cloning |
| | 23,339-24,922 | sb-RCc3 Enhancer | 1584 | Enhancer region, showing root-specific activity, from the *Sorghum bicolor* (sorghum) root cortical RCc3 (sb-RCc3) gene (WO Patent 2012112411) |
| | 24,923-25,833 | zm-PCOa Promoter | 911 | Promoter region upstream of a *Zea mays* PCO118362 mRNA sequence identified as having root-specific activity (WO Patent 2017222821) |
| | 25,834-25,851 | Intervening Sequence | 18 | DNA sequence used for cloning |
| | 25,852-26,707 | zm-HPLV9 Intron | 856 | Intron region from the *Zea mays* ortholog of an *Oryza sativa* (rice) hypothetical protein (zm-HPLV9) gene, a predicted *Zea mays* calmodulin 5 gene (Phytozome gene ID Zm00008a029682, WO Patent 2016109157) |
| | 26,708-26,716 | Intervening Sequence | 9 | DNA sequence used for cloning |
| | 26,717-28,156 | ipd079Ea | 1440 | Insecticidal protein gene from *Ophioglossum pendulum* (WO Patent 2017023486) |
| | 28,157-28,173 | Intervening Sequence | 17 | DNA sequence used for cloning |
| | 28,174-29,126 | sb-SCI-1B Terminator | 953 | Terminator region of the *Sorghum bicolor* (sorghum) subtilisin-chymotrypsin inhibitor 1B gene (WO Patent 2018102131) |
| | 29,127-29,172 | Intervening Sequence | 46 | DNA sequence used for cloning |
| | 29,173-29,632 | Z27G Terminator | 460 | Terminator region from the *Zea mays* W64 line 27-kDa gamma zein gene (Das et al., 1991; Liu et al., 2016) |

Example 2. Transformation of Maize by *Agrobacterium* Transformation and Regeneration of Transgenic Plants Containing the IPD079, PAT, and PMI Genes DP-915635-4 maize event was produced by *Agrobacterium*-mediated SSI transformation with plasmid PHP83175. *Agrobacterium*-mediated SSI was essentially performed as described in U.S. patent application publication number 2017/0240911, herein incorporated by reference.

Figure 4:
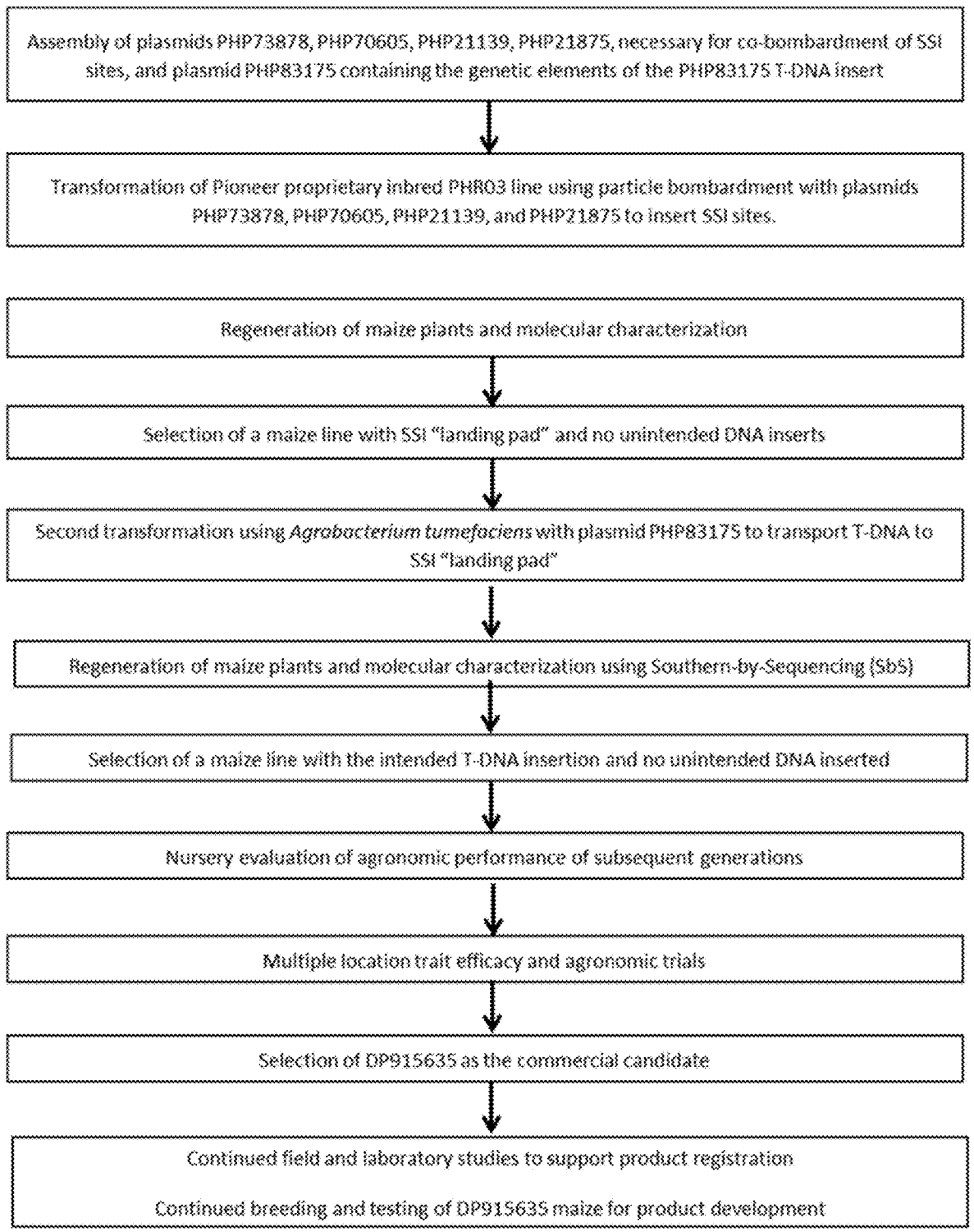
FIG. 4. shows a schematic Diagram of the Transformation and Development of DP-915635-4.

Over 2700 immature embryos were infected with PHP83175. After the 105-day selection and regeneration process, a total of 46 TO plantlets were regenerated. Samples were taken from all TO plantlets for PCR analysis to verify the presence and copy number of the inserted IPD079, PMI, and mo-PAT. In addition to this analysis, the TO plantlets were analyzed by PCR for the presence of certain *Agrobacterium* binary vector backbone sequences and for the developmental genes, zm-odp2 and zm-wus2 disclosed in U.S. Pat. Nos. 7,579,529 and 7,256,322, herein incorporated by reference in their entireties. Plants that were determined to contain single copy of the inserted genes, no *Agrobacterium* backbone sequences, and no developmental genes were selected for further greenhouse propagation. Samples from those PCR selected TO quality events were collected for further analysis using Southern-by-Sequencing to confirm that the inserted genes were in the correct target locus without any gene disruptions. Maize events DP-915635-4 were confirmed to contain a single copy of the T-DNA (See Examples 3 and 4). These selected TO plants were assayed for trait efficacy and protein expression. TO plants meeting all criteria were advanced and crossed to inbred lines to produce seed for further testing. A schematic overview of the transformation and event development is presented in FIG. 4.

Example 3. Identification of Maize Events DP-915635-4

Genomic DNA from leaf tissue representing multiple generations of maize event DP-915635-4, known copy number calibrator controls, a negative control source (DNA from a non-genetically modified maize) and no template controls (NTC) were isolated and subjected to quantitative real-time PCR (qPCR) amplification using event-specific and construct-specific primer and probes. Real-time PCR analyses of DP-915635-4 maize DNA using event-specific and construct-specific assays confirm the stable integration and segregation of a single copy of the T-DNA of plasmid PHP83175 in leaf samples tested, as demonstrated by the quantified detection of event DP-915635-4, and ipd079Ea, pmi, and mo-PAT transgenes in DP-915635-4 maize. The reliability of each event-specific and construct-specific PCR method was assessed by repeating the experiment in quadruplicate. The sensitivity, or Limit of Detection (LOD) of the PCR amplification was evaluated by testing of various dilutions of the genomic DNA from DP-915635-4.

Two generations of maize containing event DP-915635-4 were grown in cell-divided flats under typical greenhouse production conditions. Approximately 100 seed were planted for each generation.

Leaf samples were collected from each healthy plant, when plants were between the V5 and V9 growth stages. The samples were taken from the youngest leaf that was emerged from the whorl of each plant. Three leaf punches per plant were analyzed for the copy number of each event's genomic junction and the PHP83175 T-DNA through copy number PCR (qPCR) for the DP-915635-4event as well as ipd079Ea, pmi, and mo-PAT transgenes from seed grown at Pioneer Hi-Bred International, Inc. (Johnston, IA). Genomic DNA extractions from the leaf samples were performed using a high alkaline extraction protocol. Validated laboratory controls (copy number calibrators and negative) were prepared from leaf tissue using a standard cetyl trimethyl-ammonium bromide (CTAB) extraction protocol.

Genomic DNA supporting laboratory controls were quantified using Quant-iT PicoGreen® reagent (Invitrogen, Carlsbad, CA). Quantification of genomic test and control samples were estimated using the NanoDrop 2000c Spectrophotometer using NanoDrop 2000/2000c V1.6.198 Software (ThermoScientific, Wilmington, DE).

Genomic DNA samples isolated from leaf tissue of DP-915635-4 as well as control samples were subjected to real-time PCR amplification utilizing event-specific and construct specific primers and probes which span specific regions of the PHP83175 T-DNA as well as the genomic junctions that span each insertion site for events DP-915635-4. An endogenous reference gene, High Mobility Group A (hmg-A) (Krech, et al. (1999). *Gene* 234: (1) 45-50) was used in duplex with each assay for both qualitative and quantitative assessment of each assay and to demonstrate the presence of sufficient quality and quantity of DNA within the PCR reaction. The PCR target sites and size of expected PCR products for each primer/probe set are shown in Table 2. Primer and probe sequence information supporting each targeted region are shown in Table 3. PCR reagents and reaction conditions are shown in Table 4. In this study approximately 3-ng of maize genomic DNA was used for all PCR reactions.

TABLE 2

PCR Genomic DNA Target Site and Expected Size of PCR Products

| Primer and Probe Set | Targeted Regions | Expected Size of PCR Product (bp) | Amplicon SEQ ID NO: |
|---|---|---|---|
| SEQ ID NOs: 6-8 | DP-915635-4 insertion | 72 | 21 |
| SEQ ID NOs: 9-11 | ipd079Ea | 57 | 22 |
| SEQ ID NOs: 12-14 | pmi | 113 | 23 |
| SEQ ID NOs: 15-17 | mo-PAT | 76 | 24 |
| SEQ ID NOs: 18-20 | hmg-A | 79 | 25 |

TABLE 3

Primers and Probe Sequence and Amplicon for PCR Genomic DNA Targeted Regions

| Reagent | Sequence (5' to 3') | Length (base) |
|---|---|---|
| SEQ ID NO: 6 forward primer | GCATCTAGGACCGACTAGCTAACTAAC | 27 |
| SEQ ID NO: 7 reverse primer | CTTTGCATCATGTCTTGAACAATG | 24 |
| SEQ ID NO: 8 probe | 6-FAM-CGCCATGAGGAGCAA-MGB | 15 |
| SEQ ID NO: 9 forward primer | GCTGGCCGTGAAGGTGAA | 18 |
| SEQ ID NO: 10 reverse primer | TCCACGCTAGCGCTGAAGTA | 20 |
| SEQ ID NO: 11 probe | 6-FAM-CTCAGCGGAAGCTA-MGB | 14 |
| SEQ ID NO: 12 forward primer | TGACTGTCAAAGGCCACGG | 19 |
| SEQ ID NO: 13 reverse primer | AGATGGACAAGTCTAGGTTCCACC | 24 |
| SEQ ID NO: 14 probe | 6-FAM-CCGTTTAGCGCGTGTTTACAACAAGCTG-BHQ | 28 |
| SEQ ID NO: 15 forward primer | CATCGTGAACCACTACATCGAGAC | 24 |
| SEQ ID NO: 16 reverse primer | GTCGATCCACTCCTGCGG | 18 |
| SEQ ID NO: 17 probe | 6'FAM-ACCGTGAACTTCCGCACCGAGC-BHQ1 | 22 |

TABLE 3-continued

Primers and Probe Sequence and Amplicon for
PCR Genomic DNA Targeted Regions

| Reagent | Sequence (5' to 3') | Length (base) |
|---|---|---|
| SEQ ID NO: 18 forward primer | TTGGACTAGAAATCTCGTGCTGA | 23 |
| SEQ ID NO: 19 reverse primer | GCTACATAGGGAGCCTTGTCCT | 22 |
| SEQ ID NO: 20 probe | VIC-GCGTTTGTGTGGATTG-MGB | 16 |

SEQ ID NO: 21: DP-915635-4 assay amplicon sequence (72-bp; primer
and probe binding sites are in bold and underlined)
GCATCTAGGACCGACTAGCTAACTAACTAGGGCGCCATGAGGAGCAATCATTGTTCAAGACATGATGC
AAG SEQ ID NO: 22: ipd079Ea assay amplicon sequence (57-bp; primer and
probe binding sites are in bold and underlined)
GCTGGCCGTGAAGGTGAAGCTCAGCGGAAGCTACGGCTACTTCAGCGCTAGCGTGGA SEQ ID NO: 23: pmi assay amplicon sequence (113-bp; primer and probe
binding sites are in bold and underlined
TGACTGTCAAAGGCCACGGCCGTTTAGCGCGTGTTTACAACAAGCTGTAAGAGCTTACTGAAAAAATT
AACATCTCTTGCTAAGCTGGGGGTGGAACCTAGACTTGTCCATCT SEQ ID NO: 24: mo-pat assay amplicon sequence (76-bp; primer and
probe binding sites are in bold and underlined)
CATCGTGAACCACTACATCGAGACCTCCACCGTGAACTTCCGCACCGAGCCGCAGACCCCGCAGGAGT
GGATCGAC SEQ ID NO: 25: hmg-A assay amplicon sequence (79-bp; primer and
probe binding sites are in bold and underlined)
TTGGACTAGAAATCTCGTGCTGATTAATTGTTTTACGCGTGCGTTTGTGTGGATTGTAGGACAAGGCT
CCCTATGTAGC

TABLE 4

PCR Reagents and Reaction Conditions

| Step | Description | | Temperature (° C.) | Time (seconds) | Cycles |
|---|---|---|---|---|---|
| 1 | Initial Denaturation | | 95 | 120 | 1 |
| 2a | Amplif- | Denaturation | 95 | 1 | 40$^a$ |
| 2b | ication | Anneal/Extend | 60 | 20 | |

$^a$If thermal cycling is completed using a Roche LightCycler® 480, initial denaturation was 300 seconds for step 1 with 45 cycles for steps 2a and 2b.

PCR products ranging in size from 57-bp to 113-bp, representing the insertion sites for event DP-915635-4 as well as the transgenes within the T-DNA from plasmid PHP83175, were amplified and observed in 100 individual leaf samples from event DP-915635-4 as well as eight copy number calibrator genomic controls, but were absent in each of the eight negative genomic controls and eight NTC controls. Each assay was performed a total of four times with the same results observed. $C_T$ values were calculated for each sample and all positive controls.

Using the maize endogenous reference gene hmg-A, a PCR product of 79-bp was amplified and observed in 100 individual leaf samples each from event DP-915635-4 as well as eight copy number calibrator and eight negative genomic controls. Amplification of the endogenous gene was not observed in the eight No Template (NTC) controls tested with no generation of $C_T$ values. For each sample, each assay was performed in duplex with both insertion sites and all transgenes a total of four times with the same results observed each time. $C_T$ values were calculated for each sample and all positive and negative controls.

To assess the sensitivity of the construct-specific PCR assays, DP-915635-4 maize DNA was diluted in control maize genomic DNA, resulting in test samples containing various amounts of event DP-915635-4 DNA (5-ng, 1-ng, 500-pg, 250 pg, 100-pg, 50-pg, 20-pg, 10-pg, 5-pg) in a total of 5-ng maize DNA. These various amounts of DP-915635-4 maize DNA correspond to 100%, 20%, 10%, 5%, 2%, 1%, 0.4%, 0.2%, and 0.1% of DP-915635-4 maize DNA in total maize genomic DNA, respectively. The various amounts of DP-915635-4 DNA were subjected to real-time PCR amplification for transgenes ipd079Ea, PMI, and mo-PAT. Based on these analyses, the limit of detection (LOD) in 5-ng of total DNA for event DP-915635-4 was determined to be approximately 20-pg for ipd079Ea, or 0.4%, 250-pg for pmi, or 5%, and 5-pg for mo-pat, or 0.1% (DP-915635-4). The determined sensitivity of each assay described is sufficient for many screening applications. Each concentration was tested a total of four times with the same results observed each time.

Real-time PCR analyses of event DP-915635-4 utilizing event-specific and construct-specific primer/probe sets for event DP-915635-4 confirm the stable integration and segregation of a single copy of the T-DNA of plasmid PHP83175 of the event in leaf samples tested, as demonstrated by the quantified detection of ipd079Ea, pmi, and mo-PAT transgenes in DP-915635-4 maize. These results were reproducible among all the replicate qPCR analyses conducted. The maize endogenous reference gene assay for detection of hmg-A amplified as expected in all the test samples, negative controls and was not detected in the NTC samples. The sensitivity of each assay under the conditions described ranges from 5-pg to 250-pg DNA, all sufficient for many screening applications by PCR.

Example 4. Southern-by-Sequencing (SbS) Analysis of DP-915635-4 Maize for Integrity and Copy Number Southern-by-Sequencing (SbS) utilizes probe-based sequence capture, Next Generation Sequencing (NGS) techniques, and bioinformatics procedures to isolate, sequence, and identify inserted DNA within the maize genome. By compiling a large number of unique sequencing reads and comparing them to the transformation plasmid, unique junctions due to inserted DNA are identified in the bioinformatics analysis and can be used to determine the number of insertions within the plant genome. The T0 plant of DP-915635-4 maize was analyzed by SbS to determine the insertion copy number. In addition, samples of the control maize line were analyzed.

Genomic DNA was extracted from the T0 generation of DP-915635-4 maize and control plants.

Capture probes used to select PHP83175 plasmid sequences were designed and synthesized by Roche NimbleGen, Inc. (Madison, WI). A series of unique sequences encompassing the plasmid sequence was used to design overlapping biotinylated oligonucleotides as capture probes. The probe set was designed to target most sequences within the PHP83175 transformation plasmid during the enrichment process. The probes were compared to the maize genome to determine the level of maize genomic sequence that would be captured and sequenced simultaneously with the PHP83175 plasmid sequence.

Next-generation sequencing libraries were constructed for the DP-915635-4 maize plants and the control maize lines. SbS was performed as described by Zastrow-Hayes, et al. *Plant Genome* (2015). The sequencing libraries were hybridized to the capture probes through two rounds of hybridization to enrich the targeted sequences. Following NGS on a HiSeq 2500 (Illumina, San Diego, CA), the sequencing reads were assessed for trimming and quality assurance. Reads were aligned against the maize genome and the transformation construct and reads that contain both genomic and plasmid sequence were identified as junction reads. Alignment of the junction reads to the transformation construct shows borders of the inserted DNA relative to the expected insertion.

To identify junctions that included endogenous maize sequences, control maize genomic DNA libraries were captured and sequenced in the same manner as the DP-915635-4 maize plants. These libraries were sequenced to an average depth approximately five times that of the depth for the DP-915635-4 maize plant samples. This increased the probability that the endogenous junctions captured by the PHP83175 probes would be detected in the control samples, so that they could be identified and removed in the DP-915635-4 maize samples.

Figure 2:
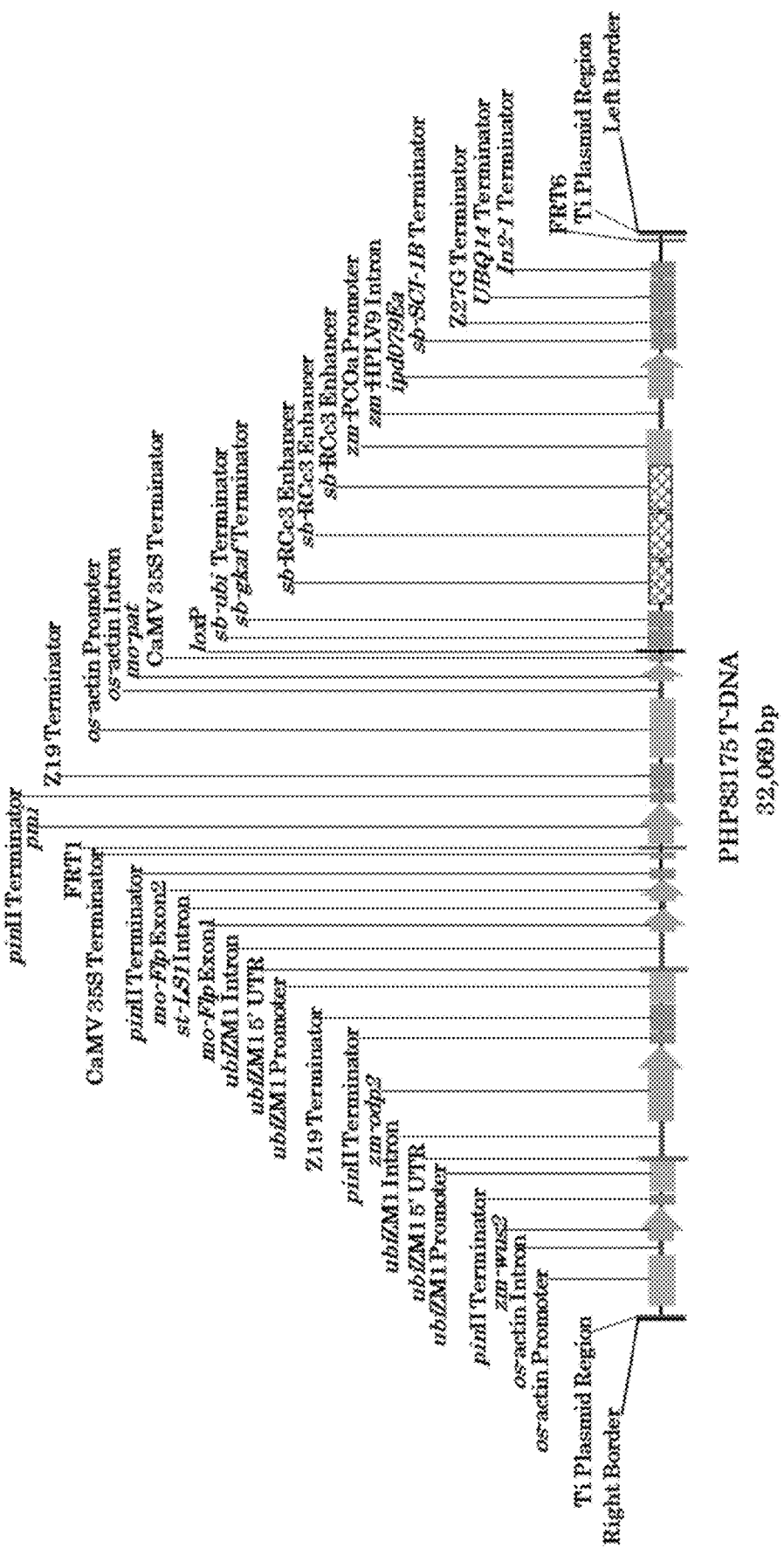
FIG. 2. shows a schematic diagram of the T-DNA indicating six gene cassettes. The T-DNA was used to transform a pre-characterized maize line containing FRT1 and FRT6 sites. The region containing the pmi gene, the mo-pat gene, and the ipd079Ea gene between the FRT1 and FRT6 sites in the T-DNA was integrated into the maize line in a site-specific manner. The zm-wus2 and zm-odp2 developmental genes were present to increase transformation efficiency. The zm-wus2, zm-odp2, and mo-Flp genes were not incorporated in the final product.

Integration and copy number of the insertion were determined in DP-915635-4 maize derived from construct PHP83175. Schematic maps of the PHP83175 plasmid and the T-DNA from PHP83175 used in transformation are provided in FIGS. 1 and 2.

Figure 3:
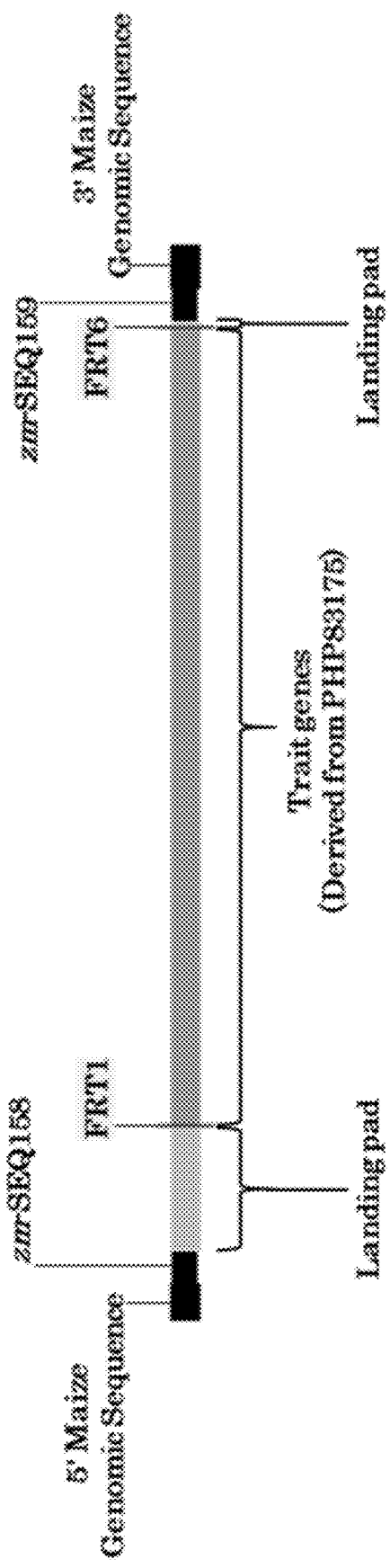
FIG. 3. shows a schematic map of the insertion in DP915635 maize based on the SbS analysis described. The flanking maize genome (including the zm-SEQ158 and zm-SEQ159 regions) is represented by the horizontal black bars. A single copy of the intended insertion, derived from PHP83175 and PHP73878, is integrated into the maize genome (SEQ ID NO: 2 is the insert T-DNA sequence). Within the insertion, the landing pad sequences from PHP73878 and the trait genes derived from PHP83175 are highlighted. SEQ ID NO: 3 is the complete insert sequence and flanking regions. The FRT1 and FRT6 sites that are the targets of recombination during the SSI process are highlighted.

SbS was conducted on the T0 plant of DP-915635-4 maize to determine the insertion copy number in the genome. Alignment of the SbS reads to the expected insertion region (including the landing pad elements zm-SEQ158 and zm-SEQ159; FIG. 3) resulted in two unique junctions between the genomic flanking sequence and the landing pad. The FRT1 and FRT6 sites are the two locations where the target trait genes from PHP83175 were integrated into the site-specific integration (SSI) landing pad. There were no other junctions between the PHP83175 sequences and the maize genome detected in the plant, indicating that there are no additional plasmid-derived insertions present in DP-915635-4 maize. Additionally, there were no junctions between non-contiguous regions of the PHP83175 T-DNA identified, indicating that there are no detectable rearrangements or truncations in the inserted DNA. Furthermore, there were no junctions between maize genome sequences and the backbone sequence of PHP83175 in the plant analyzed, demonstrating that no plasmid backbone sequences were incorporated into DP-915635-4 maize.

SbS analysis of the T0 plant of DP-915635-4 maize demonstrated that there is a single insertion containing the desired genes from the PHP83175 T-DNA in DP-915635-4 maize and that no additional insertions are present in the respective genomes.

Southern-by-Sequencing (SbS) analysis was conducted on the T0 plant of DP-915635-4 maize to confirm insertion copy number. The results indicate a single PHP83175 T-DNA insertion in the plant. No junctions between the PHP83175 T-DNA sequences and the maize genome were detected in control plants, indicating that, as expected, these plants did not contain any insertions derived from PHP83175. Furthermore, no plasmid backbone sequences were detected in the plant analyzed. SbS analysis of the T0 plant of DP-915635-4 maize demonstrated that there is a single insertion of the PHP83175 T-DNA in DP-915635-4 maize and that no additional insertions are present in the respective genomes.

A single nucleotide change, A to C change at bp 2931 in the ubiZM1 promoter of the complete insert and flanking region sequence as shown in SEQ ID NO: 32, was identified in all five plants in the ubiZM1 promoter of the pmi cassette that differs from the expected insertion sequence. As this change is in all five positive plants, it was determined to be present in the initial transformed plant. An additional single nucleotide change of a G to an A at position 8199 in SEQ ID NO: 32 was identified in the os-actin promoter of one plant of five plants; as this is the only occurrence it is likely due to a spontaneous change during the breeding process. Alignments of the reads from the five positive plants to the five plasmid maps show coverage of the genetic elements found in the intended insertion, along with coverage of the endogenous elements in the plasmids that were not incorporated into the insertion (zm-SEQ158, zm-SEQ159, zm-U6 pol III CHR8 promoter and terminator, zm-45CR1 guide RNA, In2-2 promoter, zm-wus2, and zm-odp2). Reads also aligned to the pinII terminator elements located outside of the intended insertion regions in PHP83175, PHP73878, PHP70605, and PHP21875 although these elements were not incorporated into the insertion. The NGS reads that aligned to these copies of the pinII terminator are from fragments containing the pinII terminator in the pmi cassette of the intended insertion; however, the reads from this single copy align to all copies of the pinII terminator in the plasmid maps. Similarly, reads aligned to the CaMV 35S terminator elements in the mo-Flp cassette and to the os-actin promoter and intron region of the zm-wus2 cassette in PHP83175 due to the presence of identical elements in the mo pat cassette of the intended insertion.

Example 5. Insect Efficacy of Maize Events DP-915635-4

F1 hybrid maize lines containing the insect-active IPD079Ea protein were evaluated in the field for protection against corn rootworms (CRW) by testing multiple events including DP-915635-4 maize. Data were statistically analyzed using a linear mixed model.

Field testing was conducted in 13 locations located in commercial maize-growing regions of North America: Brookings, SD (BR); Mankato, MN (MK); Marion, IA (MR); Readlyn, IA (MR_RE); Johnston, IA (JH_D2); Johnston, IA (JH_D3); Gilbert, IA (JH_GB); Watertown, WI (JV); Shabonna, IL (JV_SH); Seymour, IL (CI_SE); Fowler, IN (WN); York, NE (YK); and Lindsey, NE (YK_LI). No efficacy data were collected at six of the 13 locations (sites JH_GB, JV, JV_SH, CI_SE, YK, & YK_LI) due to a low nodal injury score (CRWNIS) below 0.75 on negative control roots.

Single-row plots (10 feet in length) were planted in a randomized complete block experimental design with two replications. Prior to planting, 168 kernels from each seed lot were characterized by PCR analysis to confirm the presence of the traits. A four-foot length of each row was manually infested utilizing a tractor-mounted CRW egg infester at a targeted infestation rate of approximately 750 eggs/plant or 1500 eggs/plant, depending on the location, when plants reached the V2-V4 growth stages. Eggs were injected into the soil approximately 4 inches deep and approximately 2-3 inches on both sides of each plant. Injury from larval feeding on roots was evaluated between 56 and 71 days after planting. Two corn roots were tagged, manually dug from the ground, washed clean of soil with pressurized water, and evaluated for the amount of larval feeding at approximately the R2 growth stage. Root injury was evaluated by visually rating and recording the amount of larval feeding contained on each root using the Iowa State 0-3 node-injury scale.

The mean node-injury root rating results from CRW for both DP-915635-4 maize and control maize are provided in Table 5. These results indicate that maize lines containing the insect-active IPD079Ea protein are efficacious against CRW.

TABLE 5

Efficacy Results Against Corn Rootworm

| Maize Line | Number of Plots | Mean Node-Injury Root Rating ± SD | Range | P-Value |
|---|---|---|---|---|
| DP915635 | 14 | 0.16 ± 0.17 | 0.02-0.71 | <0.0001[a] |
| Control | 14 | 2.02 ± 0.80 | 0.70-3.00 | |

[a]Statistically significant difference; (P-value < 0.05)

TABLE 6

Efficacy Results Against Corn Rootworm

| Maize Line | Number of Plots | Mean Node-Injury Root Rate ± SD | Range | P-Value |
|---|---|---|---|---|
| DP-915635-4 | 27 | 0.13 + 0.08 | 0.02-0.70 | <0.0001[a] |
| Control | 27 | 1.79 + 0.74 | 0.50-3.00 | |

[a]Statistically significant difference; (P-value < 0.05)

Example 6. Agronomic and Yield Field Evaluations of Maize Events DP-915635-4

Agronomic field trials containing DP-915635-4 were to generate yield data and to evaluate other agronomic characteristics. All inbred and hybrid materials tested for an event were generated from a single T0 plant.

Hybrid Trials

Hybrid trials were planted at 16 locations with a single replicate of the entry list at each location. Grain was harvested from 12 of the 16 locations. Each entry in a common background was crossed to three testers to generate hybrid seed for testing. Experiments were nested by testers, with the entries randomized within each nest. Various observations and data were collected at each planted location throughout the growing season. The following agronomic characteristics were analyzed for comparison to a wild type entry (WT), or an entry with the same genetics but without IPD079Ea, also referred to as base comparator (Table 7 and FIG. 5):

1.) Ear height (EARHT): Measurement from the ground to the attachment point of the highest developed ear on the plant. Ear height is measured in inches.
2.) Plant height (PLTHT): Measurement by drones from the ground to the base of the flag leaf. Plant height is measured in inches.
3.) Moisture (MST): Measurement of the percent grain moisture at harvest.
4.) Yield: Recorded weight of grain harvested from each plot. Calculations of reported bu/acre yields were made by adjusting to measured moisture of each plot.

Inbred Trials

Inbred trials were planted at 8 locations with 2 replicates of the entry list at each location. Grain was harvested from 7 locations for analysis. One replicate at each location was nested by construct design; the other replicate was planted as a randomized complete block. Agronomic data and observations were collected for the inbred trials and analyzed for comparison to a wild type entry (WT), or untraited version of the same genotype. Data generated for the inbred trials included the following agronomic traits (Table 8 and FIG. 6):

1.) Growing degree units to shed (GDUSHD): Measurement records the total accumulated growing degree units when 50% of the plants in the plot have tassels that are shedding pollen. A single day equivalent is approximately 2.5 growing degrees units for this data set.
2.) Ear height (EARHT): Measurement from the ground to the attachment point of the highest developed ear on the plant. Ear height is measured in inches.
3.) Plant height (PLTHT): Measurement from the ground to the base of the flag leaf. Plant height is measured in inches.
4.) Ear photometry yield (PHTYLD): Calculated yield estimates from images of harvested ears from each plot. Units for the values shown are bu/acre.

Trial Results

To evaluate the hybrid data, a mixed model framework was used to perform multi location analysis. In the multi-location analysis, main effect construct design is considered as fixed effect. Factors for location, background, tester, event, background by construct design, tester by construct design, tester by event, location by background, location by construct design, location by tester, location by background by construct design, location by tester by construct design, location by event, location by tester by event are considered as random effects. The spatial effects including range and plot within locations were considered as random effects to remove the extraneous spatial noise. The heterogeneous residual was assumed with autoregressive correlation as AR1*AR1 for each location. The estimate of construct design and prediction of event for each background were generated. The T-tests were conducted to compare construct design/event with WT. A difference was considered statistically significant if the P-value of the difference was less than 0.05. Yield analysis was by ASREML (VSN International Ltd; Best Linear Unbiased Prediction; Cullis, B. R et al (1998) *Biometrics* 54: 1-18, Gilmour, A. R. et al (2009); ASReml User Guide 3.0, Gilmour, A. R., et al (1995) *Biometrics* 51: 1440-50).

To evaluate the inbred data, a mixed model framework was used to perform multi location analysis. In the multi-location analysis, main effect construct design is considered as fixed effect. Factors for location, background, event, background by construct design, location by background, location by construct design, location by background by construct design, location by event and rep within location are considered as random effects. The spatial effects including range and plot within locations were considered as random effects to remove the extraneous spatial noise. The heterogeneous residual was assumed with autoregressive correlation as AR1*AR1 for each location. The estimate of construct design and prediction of event for each background were generated. The T-tests were conducted to compare construct design/event with WT. A difference was considered statistically significant if the P-value of the difference was less than 0.05. Yield analysis was by ASREML (VSN International Ltd; Best Linear Unbiased Prediction; Cullis, B. R et al (1998) *Biometrics* 54: 1-18, Gilmour, A. R. et al (2009); ASReml User Guide 3.0, Gilmour, A. R., et al (1995) *Biometrics* 51: 1440-50).

TABLE 7

Hybrid performance of events DP-915635-4 compared to base entry-yield

| Event | Number of plots with yield data | Predicted value (bu/acre) | Standard Error | Predicted lower 95% CL | Predicted upper 95% CL |
|---|---|---|---|---|---|
| WT (base comparator) | 68 | 207.05 | 7.76 | 191.28 | 222.83 |
| DP-915635-4 | 19 | 212.01 | 7.93 | 195.87 | 228.15 |

TABLE 8

Inbred performance of events DP-915635-4 compared to base entry-yield

| Event | Number of plots with yield data | Predicted value (bu/acre) | Standard Error | Predicted lower 95% CL | Predicted upper 95% CL |
|---|---|---|---|---|---|
| DP-915635-4 | 14 | 112.32 | 8.00 | 96.04 | 128.59 |
| WT (base comparator) | 55 | 129.66 | 7.61 | 114.18 | 145.14 |

Example 7. Protein Expression and Concentration

Protein Extraction

For analysis of IPD079Ea protein concentrations, processed root tissue sub-samples were weighed at a target weight of 20 mg. For analysis of PAT and PMI protein concentrations, processed leaf tissue sub-samples were weighed at a target weight of 10 mg. Samples were extracted with 0.60 ml of chilled phosphate-buffered saline containing polysorbate 20 (PBST). Extracted samples were centrifuged, and then supernatants were removed and prepared for analysis.

Determination of IPD079Ea Protein Concentration

Prior to analysis, samples were diluted as applicable in PBST. Standards (typically analyzed in triplicate wells) and diluted samples (typically analyzed in duplicate wells) were incubated in a plate pre-coated with an IPD079Ea-specific antibody. Following incubation, unbound substances were washed from the plate and the bound IPD07Ea protein was incubated with a different IPD079Ea-specific antibody conjugated to the enzyme horseradish peroxidase (HRP). Unbound substances were washed from the plate. Detection of the bound IPD079Ea-antibody complex was accomplished by the addition of substrate, which generated a colored product in the presence of HRP. The reaction was stopped with an acid solution and the optical density (OD) of each well was determined using a plate reader.

Determination of PAT Protein Concentration

Prior to analysis, samples were diluted as applicable in PBST. Standards (typically analyzed in triplicate wells) and diluted samples (typically analyzed in duplicate wells) were co-incubated with a PAT-specific antibody conjugated to the enzyme HRP in a plate pre-coated with a different PAT-specific antibody. Following incubation, unbound substances were washed from the plate. Detection of the bound PAT-antibody complex was accomplished by the addition of substrate, which generated a colored product in the presence of HRP. The reaction was stopped with an acid solution and the OD of each well was determined using a plate reader.

Determination of PMI Protein Concentration

Prior to analysis, samples were diluted as applicable in PBST. Standards (typically analyzed in triplicate wells) and diluted samples (typically analyzed in duplicate wells) were incubated in a plate pre-coated with a PMI-specific antibody. Following incubation, unbound substances were washed from the plate and the bound PMI protein was incubated with a different PMI-specific antibody conjugated to the enzyme HRP. Unbound substances were washed from the plate. Detection of the bound PMI-antibody complex was accomplished by the addition of substrate, which generated a colored product in the presence of HRP. The reaction was stopped with an acid solution and the OD of each well was determined using a plate reader.

Calculations for Determining Protein Concentrations

SoftMax Pro GxP (Molecular Devices) microplate data software was used to perform the calculations required to convert the OD values obtained for each set of sample wells to a protein concentration value.

A standard curve was included on each ELISA plate. The equation for the standard curve was derived by the software, which used a quadratic fit to relate the OD values obtained for each set of standard wells to the respective standard concentration (ng/ml).

Adjusted Concentration=Interpolated Sample Concentration×Dilution Factor

Adjusted sample concentration values obtained from SoftMax Pro GxP software were converted from ng/ml to ng/mg sample weight as follows:

$$\text{Sample Concentration (ng protein/mg sample weight)} = \text{Sample Concentration (ng/ml)} \cdot \frac{\text{Extraction Buffer Volume (ml)}}{\text{Sample Target Weight (mg)}}$$

Results

Protein concentration results (means, standard deviations, and ranges) were determined for IPD079Ea protein in V9 root tissue and the PAT and PMI proteins in V9 leaf tissue from two generations of DP-915635-4 maize.

TABLE 9

Expressed Trait Protein Concentration Results

| Protein | Tissue (Growth Stage) | Generation | Protein Concentration (ng/mg Tissue Dry Weight) | | Sample LLOQ | Number of Samples <LLOQ/ Total Number of Samples Reported |
|---|---|---|---|---|---|---|
| | | | Mean ± SD | Range | | |
| IPD079Ea | Root (V9) | T3 | 22 ± 7.0 | 14-29 | 0.069 | 0/5 |
| | | F1 | 20 ± 3.1 | 15-23 | 0.069 | 0/5 |
| PAT | Leaf (V9) | T3 | 6.3 ± 0.64 | 5.6-7.2 | 0.11 | 0/5 |
| | | F1 | 5.1 ± 0.63 | 4.2-5.9 | 0.11 | 0/5 |
| PMI | Leaf (V9) | T3 | 11 ± 2.5 | 7.8-14 | 0.54 | 0/5 |
| | | F1 | 5.8 ± 0.86 | 4.9-7.2 | 0.54 | 0/5 |

The above description of various illustrated embodiments of the disclosure is not intended to be exhaustive or to limit the scope to the precise form disclosed. While specific embodiments of and examples are described herein for illustrative purposes, various equivalent modifications are possible within the scope of the disclosure, as those skilled in the relevant art will recognize. The teachings provided herein can be applied to other purposes, other than the examples described above. Numerous modifications and variations are possible in light of the above teachings and, therefore, are within the scope of the appended claims.

These and other changes may be made in light of the above detailed description. In general, in the following claims, the terms used should not be construed to limit the scope to the specific embodiments disclosed in the specification and the claims.

The entire disclosure of each document cited (including patents, patent applications, journal articles, abstracts, manuals, books or other disclosures) in the Background, Detailed Description, and Examples is herein incorporated by reference in their entireties.

Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight; temperature is in degrees celsius; and pressure is at or near atmospheric.

What is claimed is:

1. A corn plant comprising event DP-915635-4, wherein said event comprises a nucleotide sequence as set forth in SEQ ID NO: 26 and SEQ ID NO: 29, wherein a representative sample of seed of said corn event has been deposited with American Type Culture Collection (ATCC) with Accession No. PTA-126746.

2. The corn plant of claim 1, wherein said event comprises the nucleotide sequence set forth in SEQ ID NO: 27 and SEQ ID NO: 30.

3. The corn plant of claim 1, wherein said genotype comprises the nucleotide sequence set forth in SEQ ID NO: 28 and SEQ ID NO: 31.

4. A DNA construct comprising an operably linked first and second expression cassette, wherein said first expression cassette comprises:
   1) an sb-RCc3 Enhancer
   2) a zm-PCOa Promoter;
   3) a zm-HPLV9 Intron;
   4) an ipd079Ea; and
   5) an sb-SCI-1B Terminator.

5. A plant comprising the DNA construct of claim 4.

6. The plant of claim 5, wherein said plant is a corn plant.

7. A plant comprising the sequence set forth in SEQ ID NO: 21.

8. A corn event DP-915635-4, wherein a representative sample of seed of said corn event has been deposited with American Type Culture Collection (ATCC) with Accession No. PTA-126746.

9. Plant parts of the corn event of claim 8, wherein a representative sample of seed of said corn event has been deposited with American Type Culture Collection (ATCC) with Accession No. PTA-126746, wherein the plant parts comprise the corn event DP-915635-4.

10. A corn seed comprising corn event DP-915635-4, wherein said seed comprises a DNA molecule chosen from SEQ ID NO: 26 and SEQ ID NO: 29, wherein a representative sample of the corn event DP-915635-4 seed of has been deposited with American Type Culture Collection (ATCC) with Accession No. PTA-126746.

11. A corn plant, or part thereof, grown from the seed of claim 10.

12. A transgenic seed produced from the corn event of claim 8.

13. A transgenic corn plant, or part thereof, grown from the seed of claim 12.

14. An isolated nucleic acid molecule comprising a nucleotide sequence chosen from SEQ ID NOs: 21, 26-28, and 31, and full length complements thereof.

15. An amplicon comprising the nucleic acid sequence chosen from SEQ ID NOs: 22 and 23 and full length complements thereof.

16. A biological sample derived from corn event DP-915635-4 plant, tissue, or seed, wherein said sample comprises a nucleotide sequence which is or is complementary to a sequence chosen from SEQ ID NO: 26 and SEQ ID NO: 29, wherein said nucleotide sequence is detectable in said sample using a nucleic acid amplification or nucleic acid hybridization method, wherein a representative sample of said corn event DP-915635-4 seed has been deposited with American Type Culture Collection (ATCC) with Accession No. PTA-126746.

17. The biological sample of claim 16, wherein said biological sample comprises plant, plant tissue, or seed of transgenic corn event DP-915635-4.

18. The biological sample of claim 17, wherein said biological sample is a DNA sample extracted from the transgenic corn plant event DP-915635-4, and wherein said DNA sample comprises one or more of the nucleotide sequences chosen from SEQ ID NOs: 21-31, and the complement thereof.

19. The biological sample of claim 16, wherein said biological sample is chosen from corn flour, corn meal, corn syrup, corn oil, corn starch, and cereals manufactured in whole or in part to contain corn by-products.

20. An extract derived from corn event DP-915635-4 plant, tissue, or seed and comprising a nucleotide sequence which is or is complementary to a sequence chosen from SEQ ID NO: 26 and SEQ ID NO: 29, wherein a representative sample of said corn event DP-915635-4 seed has been deposited with American Type Culture Collection (ATCC) with Accession No. PTA-126746.

21. The extract of claim 20, wherein said nucleotide sequence is detectable in said extract using a nucleic acid amplification or nucleic acid hybridization method.

22. The extract of claim 21, wherein said extract comprises plant, plant tissue, or seed of transgenic corn plant event DP-915635-4.

23. The extract of claim 22, wherein the extract is a composition chosen from corn flour, corn meal, corn syrup, corn oil, corn starch, and cereals manufactured in whole or in part to contain corn by-products, wherein said composition comprises a detectable amount of said nucleotide sequence.

24. A method of producing hybrid corn seeds comprising:
   A) sexually crossing a first inbred corn line comprising a nucleotide chosen from SEQ ID NOs: 21, 22, 24, 26-31 and a second inbred line having a different genotype;
   B) growing progeny from said crossing; and
   C) harvesting the hybrid seed produced thereby.

25. The method according to claim 24, wherein the first inbred corn line is a female parent.

26. The method according to claim 24, wherein the first inbred corn line is a male parent.

27. A method for producing a corn plant resistant to coleopteran pests comprising:
A) sexually crossing a first parent corn plant with a second parent corn plant, wherein said first or second parent corn plant comprises event DP-915635-4, wherein a representative sample of seed of said corn event has been deposited with American Type Culture Collection (ATCC) with Accession No. PTA-126746, thereby producing a plurality of first generation progeny plants;
B) selfing the first generation progeny plant, thereby producing a plurality of second generation progeny plants; and
C) selecting from the second generation progeny plants that comprise the event DP-915635-4 and are resistant to a coleopteran pest.

28. A method of producing hybrid corn seeds comprising:
A) sexually crossing a first inbred corn line comprising the DNA construct of claim 1 with a second inbred line not comprising the DNA construct of claim 1; and
B) harvesting the hybrid seed produced thereby.

29. The method of claim 28, further comprising the step of backcrossing a second generation progeny plant that comprises corn event DP-915635-4 to the parent plant that lacks the corn event DP-915635-4 DNA, thereby producing a backcross progeny plant that is resistant to a coleopteran pest.

30. A method for producing a corn plant resistant to a corn rootworm, said method comprising:
A) crossing a first parent corn plant with a second parent corn plant, wherein said first or second parent corn plant comprises event DP-915635-4, wherein a representative sample of seed of said corn event has been deposited with American Type Culture Collection (ATCC) with Accession No. PTA-126746, thereby producing a plurality of first generation progeny plants;
B) selecting a first generation progeny plant that comprises the event DP-915635-4;
C) backcrossing the first generation progeny plant of step (b) with a parent plant that lacks the corn event DP-915635-4 DNA, thereby producing a plurality of backcross progeny plants; and
D) selecting from the backcross progeny plants, a plant that comprises the event DP-915635-4;
wherein the selected backcross progeny plant of step (d) comprises SEQ ID NO: 21, 26, or 29.

31. The method according to claim 30, wherein the plants of the first parent corn line are the female parents or male parents.

32. Hybrid seed produced by the method of claim 30.

33. A method of determining zygosity of a corn plant comprising event DP-915635-4 in a biological sample comprising:
A) contacting said sample with a first pair of DNA molecules and a second distinct pair of DNA molecules such that:
1) When used in a nucleic acid amplification reaction comprising corn event DP-915635-4 DNA, produces a first amplicon that is diagnostic for event DP-915635-4, and
2) When used in a nucleic acid amplification reaction comprising corn genomic DNA other than DP-915635-4 DNA, produces a second amplicon that is diagnostic for corn genomic DNA other than DP-915635-4 DNA;
B) performing a nucleic acid amplification reaction; and
C) detecting the amplicons so produced, wherein detection of the presence of both amplicons indicates that said sample is heterozygous for corn event DP-915635-4 DNA, wherein detection of only the first amplicon indicates that said sample is homozygous for corn event DP-915635-4 DNA;
wherein a representative sample of seed of said corn event has been deposited with American Type Culture Collection (ATCC) with Accession No. PTA-126746.

34. The method of claim 33, wherein the first pair of DNA molecules comprises primer pair SEQ ID NOs: 6 and 7.

35. The method of claim 33, wherein the first and second pair of DNA molecules comprise a detectable label.

36. The method of claim 35, wherein the detectable label is a fluorescent label.

37. The method of claim 35, wherein the detectable label is covalently associated with one or more of the primer molecules.

38. A method of detecting the presence of a nucleic acid molecule that is unique to event DP-915635-4 in a sample comprising corn nucleic acids, the method comprising:
A) contacting the sample with a pair of primers that, when used in a nucleic-acid amplification reaction with genomic DNA from event DP-915635-4 produces an amplicon that is diagnostic for event DP-915635-4;
B) performing a nucleic acid amplification reaction, thereby producing the amplicon that is diagnostic for event DP-915635-4; and
C) detecting the amplicon that is diagnostic for event DP-915635-4;
wherein a representative sample of seed of said corn event has been deposited with American Type Culture Collection (ATCC) with Accession No. PTA-126746.

39. The method of claim 38, wherein the nucleic acid molecule that is diagnostic for event DP-915635-4 is an amplicon produced by the nucleic acid amplification chain reaction.

40. The method of claim 38, wherein the probe comprises a detectable label.

41. The method of claim 40, wherein the detectable label is a fluorescent label.

42. The method of claim 40, wherein the detectable label is covalently associated with the probe.

43. A plurality of polynucleotide primers comprising one or more polynucleotides which target event DP-915635-4 DNA template in a sample to produce an amplicon diagnostic for event DP-915635-4 as a result of a polymerase chain reaction method.

44. A pair of polynucleotide primers targeting event DP-915635-4 DNA template in a sample to produce an amplicon diagnostic for event DP-915635-4 according to claim 43, wherein
A) the first polynucleotide primer comprises a nucleotide sequence as set forth in SEQ ID NO: 6, and the complements thereof; and
B) the second polynucleotide primer comprises a nucleotide sequence as set forth in SEQ ID NO: 7, and the complements thereof.

45. The primer pair of claim 44, wherein said first primer and said second primer are at least 18 nucleotides.

46. A method of detecting the presence of DNA corresponding to event DP-915635-4 in a sample, the method comprising:

A) contacting the sample comprising maize DNA with a polynucleotide probe that hybridizes under stringent hybridization conditions with DNA from maize event DP-915635-4 and does not hybridize under said stringent hybridization conditions with a non-DP-915635-4 maize plant DNA;

B) subjecting the sample and probe to stringent hybridization conditions; and

C) detecting hybridization of the probe to the DNA;

wherein detection of hybridization indicates the presence of event DP-915635-4, and wherein a representative sample of seed of said corn event has been deposited with American Type Culture Collection (ATCC) with Accession No. PTA-126746.

47. A kit for detecting nucleic acids that are unique to event DP-915635-4 comprising at least one nucleic acid molecule of sufficient length of contiguous polynucleotides to function as a primer or probe in a nucleic acid detection method, and which upon amplification of or hybridization to a target nucleic acid sequence in a sample followed by detection of the amplicon or hybridization to the target sequence, are diagnostic for the presence of nucleic acid sequences unique to event DP-915635-4 in the sample, wherein the nucleic acid molecule comprises a nucleotide sequence selected from the group consisting of SEQ ID NO: 6-28, 31, and complements thereof.

48. A corn plant comprising the genotype of the corn event DP-915635-4, wherein said genotype comprises a nucleotide sequence having at least 95% sequence identity to SEQ ID NO: 26 and SEQ ID NO: 29, wherein a representative sample of seed of said corn event has been deposited with American Type Culture Collection (ATCC) with Accession No. PTA-126746.

49. The corn plant of claim 48, wherein said genotype comprises a nucleotide sequence having at least 95% sequence identity to SEQ ID NO: 27 and SEQ ID NO: 30.

50. The corn plant of claim 48, wherein said genotype comprises a nucleotide sequence having at least 95% sequence identity to SEQ ID NO: 28 and SEQ ID NO: 31.

51. The corn plant of claim 48, wherein the genotype comprises a nucleotide sequence having 1, 2, 3, 4, or 5 nucleotide changes in one of SEQ ID NO: 26 or SEQ ID NO: 27.

* * * * *